United States Patent [19]
Lee et al.

[11] Patent Number: 5,978,497
[45] Date of Patent: Nov. 2, 1999

[54] APPARATUS FOR THE IDENTIFICATION OF FREE-LYING CELLS

[75] Inventors: Shih-Jong J. Lee, Bellevue; Paul S. Wilhelm, Kirkland; Wendy R. Bannister, Seattle; Chih-Chau L. Kuan, Redmond; Seho Oh, Mukilteo; Michael G. Meyer, Seattle, all of Wash.

[73] Assignee: NeoPath, Inc., Redmond, Wash.

[21] Appl. No.: 08/309,250

[22] Filed: Sep. 20, 1994

[51] Int. Cl.⁶ ........................................ G06K 9/00
[52] U.S. Cl. ........................ 382/133; 382/173; 382/190; 382/224
[58] Field of Search ...................... 382/128, 133, 382/134, 173, 190, 224; 364/413.1, 413.08

[56] References Cited

U.S. PATENT DOCUMENTS

| | | |
|---|---|---|
| 3,824,393 | 7/1974 | Brain . |
| 4,097,845 | 6/1978 | Bacus . |
| 4,122,518 | 10/1978 | Castleman et al. . |
| 4,175,860 | 11/1979 | Bacus . |
| 4,183,013 | 1/1980 | Agrawala et al. . |
| 4,199,748 | 4/1980 | Bacus . |
| 4,513,438 | 4/1985 | Graham et al. . |
| 4,523,278 | 6/1985 | Reinhardt et al. . |
| 4,538,299 | 8/1985 | DeForest . |
| 4,709,333 | 11/1987 | Crawford . |
| 4,724,543 | 2/1988 | Klevecz et al. . |
| 4,731,860 | 3/1988 | Wahl . |
| 4,965,725 | 10/1990 | Rutenberg . |
| 4,973,111 | 11/1990 | Haacke et al. . |
| 4,975,972 | 12/1990 | Bose et al. . |
| 5,016,283 | 5/1991 | Bacus et al. . |
| 5,086,476 | 2/1992 | Bacus . |
| 5,162,990 | 11/1992 | Odeyale et al. . |
| 5,231,005 | 7/1993 | Russell et al. . |
| 5,253,302 | 10/1993 | Massen . |
| 5,257,182 | 10/1993 | Luck et al. ........................... 364/413.1 |
| 5,268,967 | 12/1993 | Jang et al. . |
| 5,281,517 | 1/1994 | Bacus et al. . |
| 5,287,272 | 2/1994 | Rutenberg et al. . |
| 5,315,700 | 5/1994 | Johnston et al. . |
| 5,361,140 | 11/1994 | Hayenga et al. . |
| 5,528,703 | 6/1996 | Lee ........................................ 382/257 |

OTHER PUBLICATIONS

Lee, James S.J., et al., "A Processing Strategy for Automated Papanicolaou Smear Screening", *Analytical and Quantitative Cytology and HIstology*, vol. 14, No. 5, Oct. 1992, pp. 415–425.

Bacus, James W. and Les J. Grace, "Optical Microscope System For Standardized Cell Measurements and Analyses", *Applied Optics*, 26:16, pp. 3280–3293, Aug. 15, 1987.

Bartels, Peter H., et al., "A Self–Learning Computer Program for Cell Recognition", *ACTA Cytologica: The Journal of Clinical Cytology*, 14:8, pp. 486–494, Oct. 1970.

Duda, Richard O. and Peter E. Hart, "Fisher's Linear Discriminant", *Patent Classification and Scene Analysis*, Copyright ©1973, pp. 114–119.

(List continued on next page.)

*Primary Examiner*—Phuoc Tran
*Attorney, Agent, or Firm*—Hans I. Sun; Emil Moffa

[57] ABSTRACT

A free-lying cell classifier. An automated microscope system comprising a computer and high speed processing field of view processors identifies free-lying cells. An image of a biological specimen is obtained and the image is segmented to create a set of binary masks. The binary masks are used by a feature calculator to compute the features that characterize objects of interest including free-lying cells, artifacts and other biological objects. The objects are classified to identify their type, their normality or abnormality or their identification as an artifact. The results are summarized and reported. A stain evaluation of the slide is performed as well as a typicality evaluation. The robustness of the measurement is also quantified as a classification confidence value. The free-lying cell evaluation is used by an automated cytology system to classify a biological specimen slide.

17 Claims, 19 Drawing Sheets

OTHER PUBLICATIONS

Mackin, Robert W., Badrinath Roysam, et al., "Automated Three–Dimensional Image Analysis of Thick and Overlapped Clusters in Cytologic Preparations: Application to Cytologic Smears", *Analytical and Quantitative Cytology and Histology*, 15:6, Dec. 1993, pp. 405–417.

Otsu, Nobuyuki, "A Thresold Selection Method from Gray–Level Histograms", *IEEE Transactions on Systems, Man, and Cybernetics*, vol. SMC–9, No. 1, Jan. 1979, pp. 62–66.

Dytch, Harvey E. et al., "An Interactive Microcomputer–Based System for the Quantitative Analysis of Stratified Tissue Sections", *Analytical and Quantitative Cytology and Histology*, vol. 9, No. 1, pp. 69–78, Mar. 1987.

Tanaka, Noboru, et al., "Automated Cytologic Screening System (CYBEST Model 4): an Integrated Image Cytometry System", Reprinted from *Applied Optics*, vol. 26, p. 3301, Aug. 15, 1987. Copyright © 1987 by the Optical Society of America and reprinted by permission of the copyright owner.

Enslein, Kurt and Peter W. Neurath, "Augmented Stepwise Discriminant Analysis Applied to Two Classification Problems in the Biomedical Field", *Computers and Biomedical Research*, 2,pp.568–581 (1969).

Kurman, Robert J. et al., "Part 1: Specimen Adequacy" and "Part 2: Descriptive Diagnoses", *The Bethesda System for Reporting Cervical/Vaginal Cytologic Diagnoses*, Springer–Verlag, 5 pages.

Weber, J.E. et al., "Fuzzy Reasoning, Possibility Theory and Probability Theory in Expert Systems for Histopathology", IEEE/Ninth Annual Conference of the Engineering in Medicine and Biology Society, pp. 1560–1562, ©1987.

Wied, G.L. et al., "Expert Systems as Classifiers in Diagnostic Cytopathology", IEEE/Ninth Annual Conference of the Engineering in Medicine and Biology Society, pp. 1915–1917, ©1987.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas–Stratex, an Expert Diagnostic System For Stratified Cervical Epithelium", IEEE/Ninth Annual Conference of the Engineering in Medical and Biology Society, pp. 1557–1559, ©1987.

Serra, J., *Image Analysis and Mathematical Morphology*, pp. 372–423, Academic Press, 1982.

Smith, Warren J., "Image Evaluation", *Modern Optical Engineering*, McGraw–Hill Book company, 1966, pp. 308–325.

Patten, Jr., Stanley, "Diagnostic Cytopathology of the Uterine Cervix", Basel, Switzerland, Publisher: S. Karger, 1969, 2nd Edition 1978, Third volume in *Monographs in Clinical Cytology*, edited by G.L. Wied, pp. 10–15.

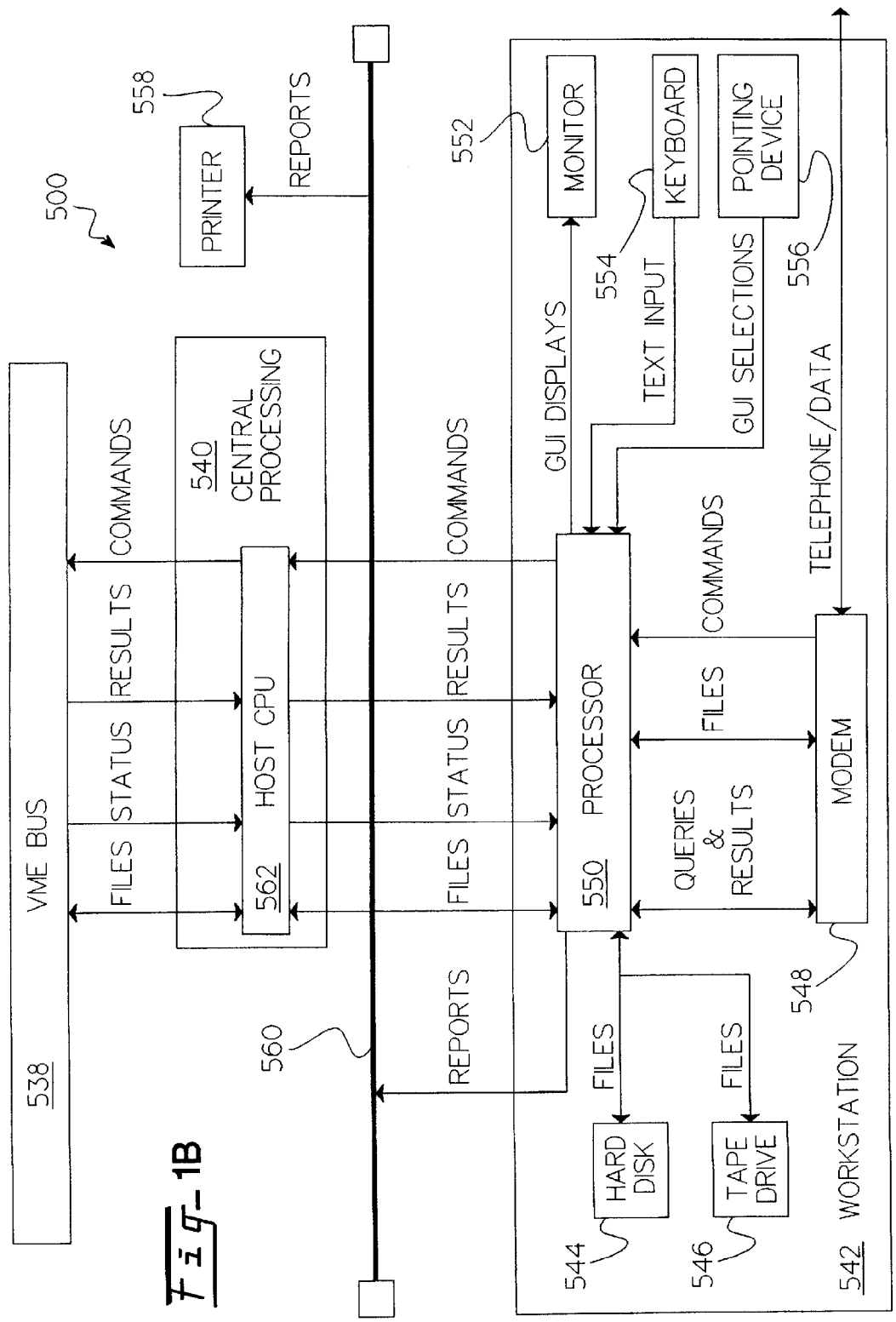

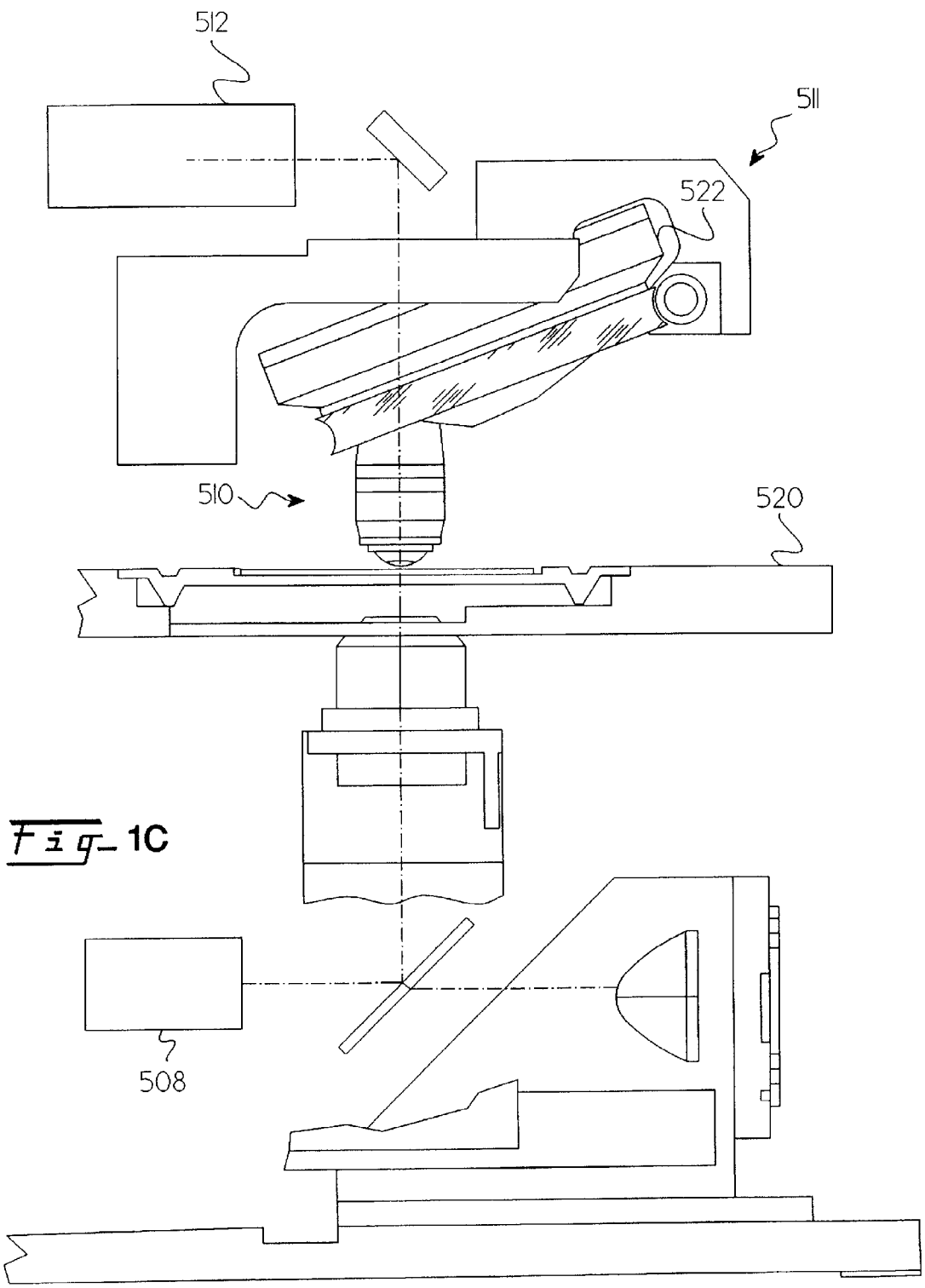

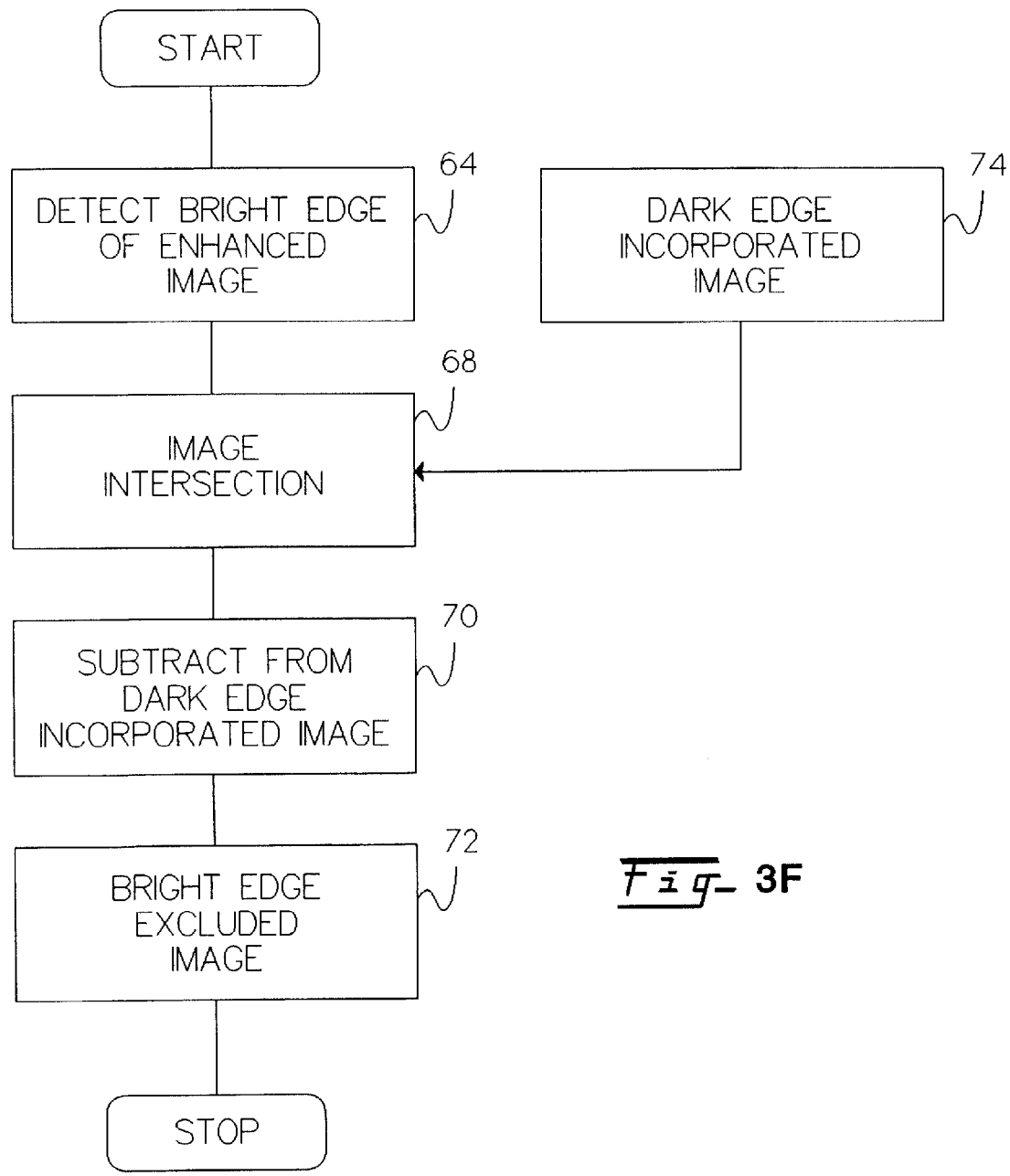

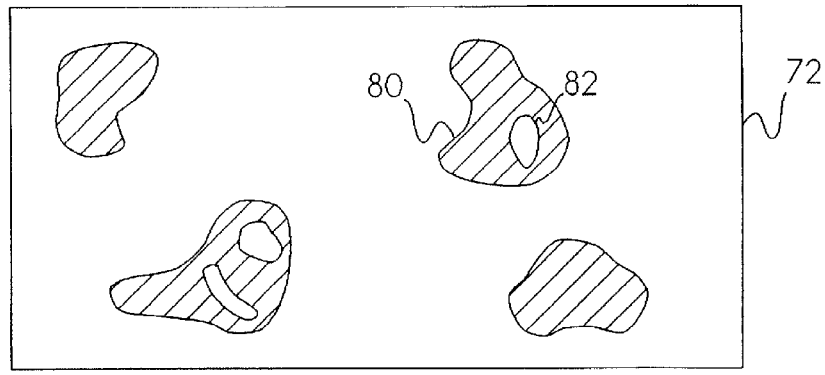
*Fig-* 3G
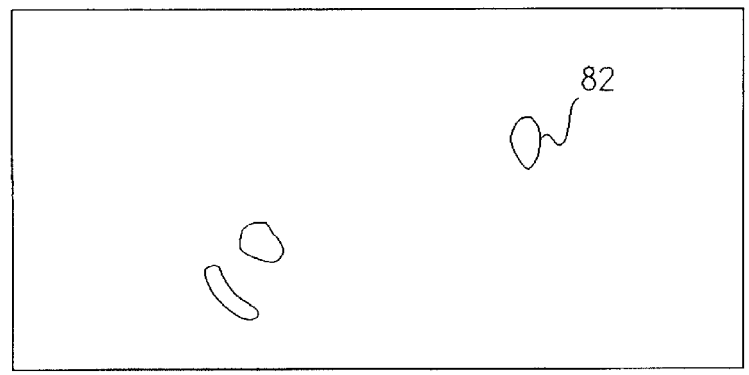
*Fig-* 3H
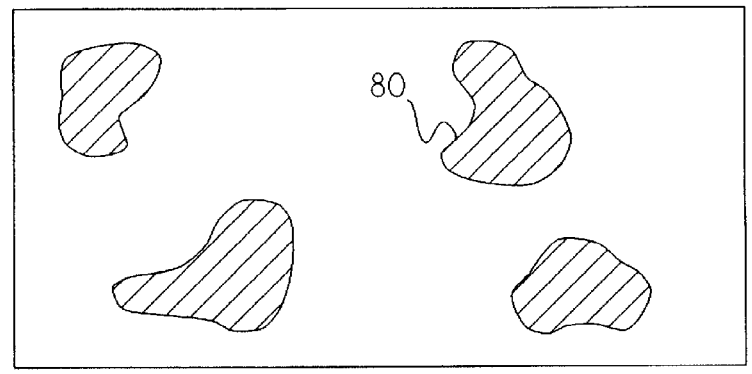
*Fig-* 3I

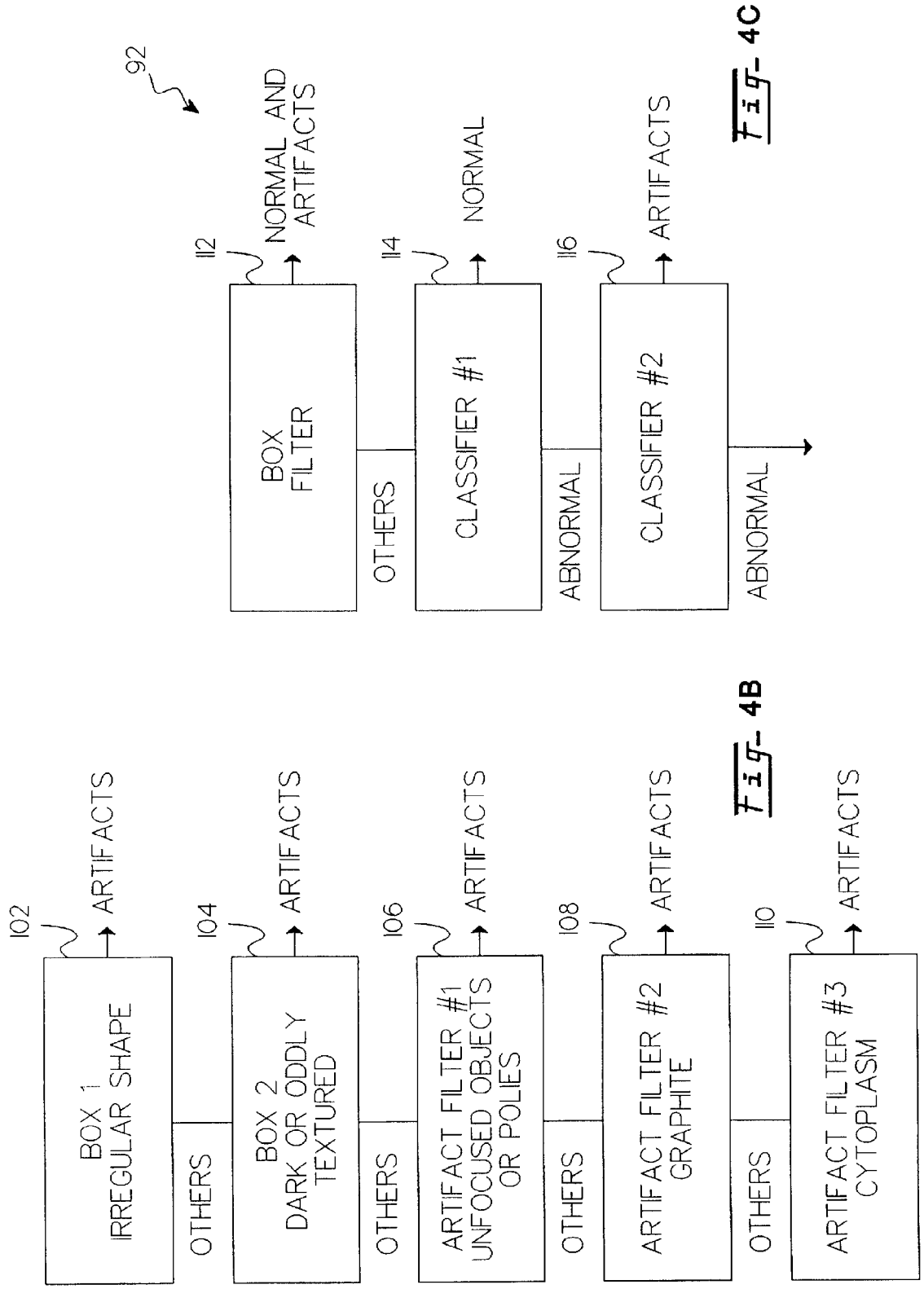

APPARATUS FOR THE IDENTIFICATION OF FREE-LYING CELLS

The invention relates to an automated cytology system and more particularly to an automated cytology that identifies and classifies free-lying cells and cells having isolated nuclei on a biological specimen slide.

BACKGROUND OF THE INVENTION

One goal of a Papanicolaou smear analysis system is to emulate the well established human review process which follows standards suggested by The Bethesda System. A trained cytologist views a slide at low magnification to identify areas of interest, then switches to higher magnification where it is possible to distinguish normal cells from potentially abnormal ones according to changes in their structure and context. In much the same way as a human reviews Papanicolaou smears, it would be desirable for an automated cytology analysis system to view slides at low magnification to detect possible areas of interest, and at high magnification to locate possible abnormal cells. As a cytologist compares size, shape, texture, context and density of cells against established criteria, so it would be desirable to analyze cells according to pattern recognition criteria established during a training period.

SUMMARY OF THE INVENTION

The invention identifies and classifies free-lying cells and cells having isolated nuclei on a biological specimen: single cells. Objects that appear as single cells bear the most significant diagnostic information in a pap smear. Objects that appear as single cells may be classified as being either normal cells, abnormal cells, or artifacts. The invention also provides a confidence level indicative of the likelihood that an object has been correctly identified and classified. The confidence level allows the rejection of slides having only a few very confident abnormal cells. The staining characteristics of the slide are also evaluated. The invention first acquires an image of the biological specimen at a predetermined magnification. Objects found in the image are identified and classified. This information is used for subsequent slide classification.

In one embodiment, the invention utilizes a set of statistical decision processes that identify potentially neoplastic cells in Papanicolaou-stained cervical/vaginal smears. The decisions made in accordance with the invention as to whether an individual cell is normal or potentially neoplastic are used to determine if a slide is clearly normal or requires human review. The apparatus of the invention uses nuclear and cytoplasm detection with classification techniques to detect and identify free-lying cells and cells having isolated nuclei. The apparatus of the invention can detect squamous intraepithelial lesion (SIL) or other cancer cells.

In addition to the detection and classification of single cells, the invention measures the specimen cell population to characterize the slide. Several measures of stain related features are measured for objects which are classified as intermediate squamous cells. Also, many measures are made of the confidence with which objects are classified at various stages in the single cell algorithm. All of this information is used in conjunction with the number of potentially neoplastic cells to determine a final slide score. The invention performs three levels of processing: image segmentation, feature extraction, and object classification.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIGS. 1A, 1B and 1C show the automated cytology screening apparatus of the invention.

FIG. 3F shows the bright edge removal method of the invention.

FIGS. 3G, 3H and 3I show refinement of an image by small hole removal.

FIG. 4B shows an initial box filter.

FIG. 4C shows a stage 1 classifier.

DETAILED DESCRIPTION OF THE PREFERRED EMBODIMENT

Figure 1A:
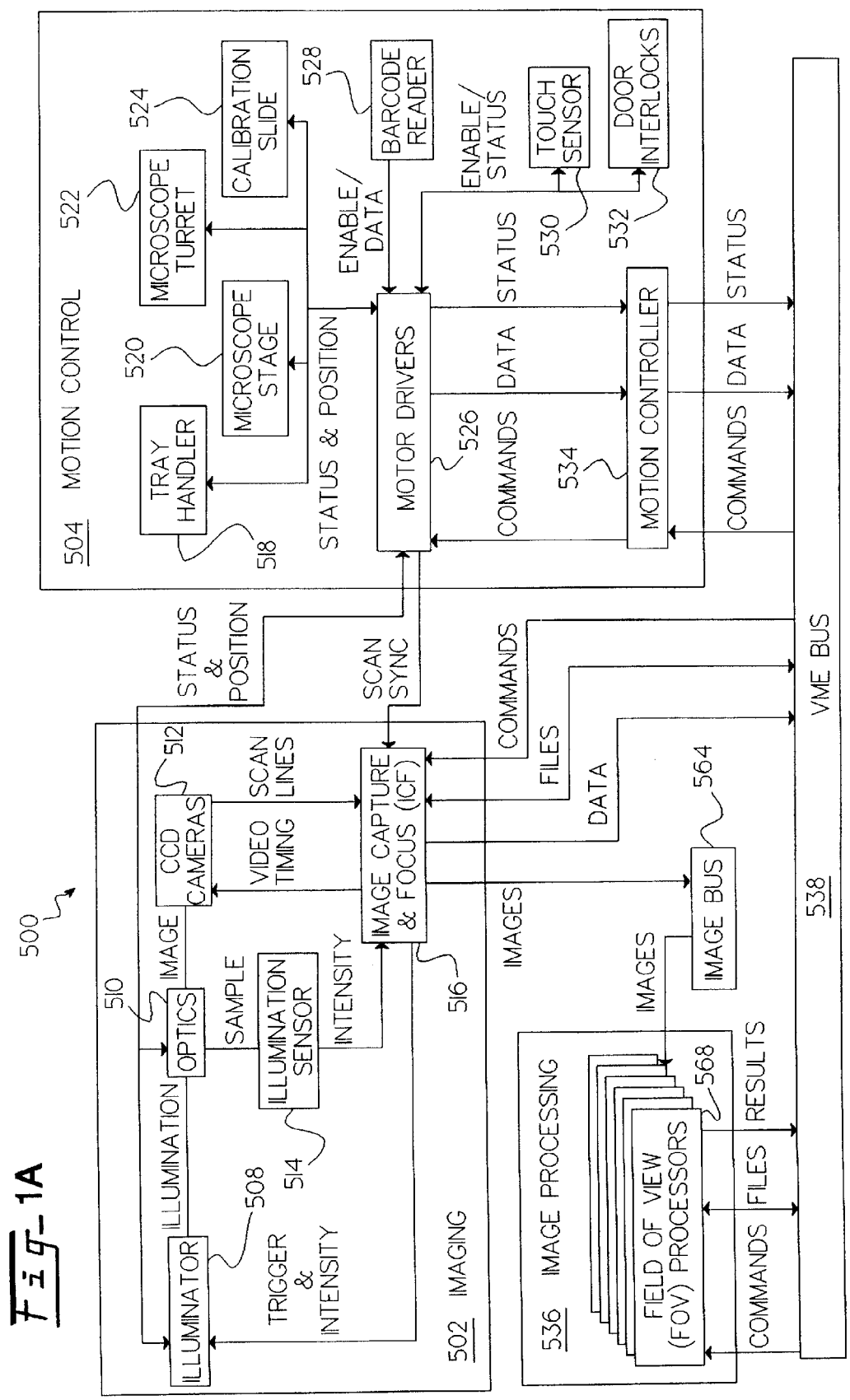

In a presently preferred embodiment of the invention, the system disclosed herein is used in a system for analyzing cervical pap smears, such as that shown and disclosed in pending U.S. patent application Ser. No. 08/571,686 which is a file wrapper continuation of abandoned U.S. patent application Ser. No. 07/838,064, entitled "Method For Identifying Normal Biomedical Specimens", by Alan C. Nelson et al., filed Feb. 18, 1992; U.S. Pat. No. 5,528,703 which is a continuation in part of abandoned U.S. patent application Ser. No. 07/838,395, entitled "Method For Identifying Objects Using Data Processing Techniques", by S. James Lee, filed Feb. 18, 1992; U.S. patent application Ser. No. 07/838,070, now U.S. Pat. No. 5,315,700, entitled "Method And Apparatus For Rapidly Processing Data Sequences", by Richard S. Johnston et al., filed Feb. 18, 1992; U.S. patent application Ser. No. 07/838,065, filed Feb. 18, 1992, now U.S. Pat. No. 5,361,140 entitled "Method and Apparatus for Dynamic Correction of Microscopic Image Signals" by Jon W. Hayenga et al.; and allowed U.S. patent application Ser. No. 08/302,355, for which the issue fee has been paid, filed Sep. 7, 1994 entitled "Method and Apparatus for Rapid Capture of Focused Microscopic Images" to Hayenga et al., which is a continuation-in-part of abandoned U.S. patent application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention and which are all hereby incorporated by reference including pending U.S. patent application Ser. No. 08/309,118 to Kuan et al. entitled, "Field Prioritization Apparatus and Method," pending U.S. patent application Ser. No. 08/309,061 to Wilhelm et al., entitled "Apparatus for Automated Identification of Cell Groupings on a Biological Specimen, " pending U.S. patent application Ser. No. 08/309,116 to Meyer et al. entitled "Apparatus for Automated Identification of Thick Cell Groupings on a Biological Specimen, " pending U.S. patent application Ser. No. 08/667,292, filed Jun. 20, 1996, which is a file wrapper continuation of abandoned U.S. patent application Ser. No. 08/309,115 to Lee et al. entitled "Biological Analysis System Self Calibration Apparatus," pending U.S. patent application Ser. No. 08/678,124, filed Jul. 11, 1996, which is a file wrapper continuation of abandoned U.S. patent application Ser. No. 08/309,992 to Lee et al. entitled "Apparatus for Identification and Integration of Multiple Cell Patterns," U.S. patent application Ser. No. 08/309,063, now U.S. Pat. No. 5,627,908 issued May 6, 1997, to Lee et al. entitled "A Method for Cytological System Dynamic Normalization," U.S. patent application Ser. No. 08/309,248, now U.S. Pat. No. 5,638,459 issued Jun. 10, 1997, to Rosenlof et al. entitled "Method and Apparatus for Detecting a Microscope Slide Coverslip," U.S. patent application Ser. No. 08/309, 077, now U.S. Pat. No. 5,566,249, issued Oct. 15, 1996 to Rosenlof et al., entitled "Apparatus for Detecting Bubbles in Coverslip Adhesive," pending U.S. patent application Ser. No. 08/309,931 to Lee et al. entitled "Cytological Slide Scoring Apparatus," allowed U.S. patent application Ser. No. 08/309,148, for which the issue fee has been paid, to Lee et al. entitled "Method and Apparatus for Image Plane Modulation Pattern Recognition", allowed U.S. patent application Ser. No. 08/309,209, for which the issue fee has been paid, to Oh et al. entitled "A Method and Apparatus for Robust Biological Specimen Classification," allowed U.S. patent application Ser. No. 08/309,117, for which the issue fee has been paid, to Wilhelm et al., entitled "Method and Apparatus for Detection of Unsuitable Conditions for Automated Cytology Scoring."

It is to be understood that the various processes described herein may be implemented in software suitable for running on a digital processor. The software may be embedded, for example, in the central processor 540.

Now refer to FIGS. 1A, 1B and 1C which show a schematic diagram of one embodiment of the apparatus of the invention for field of view prioritization. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a MOTOROLA 68030 CPU. The motion controller 504 is comprised of a tray handler 518, a microscope stage controller 520, a microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a SUN SPARC CLASSIC (™) workstation. A tape drive 546 is connected to the workstation 550 as well as a modem 548, a monitor 552, a keyboard 554, and a mouse pointing device 556. A printer 558 is connected to the ethernet 560.

During object identification and classification, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

The computer system 540 accumulates results from the 4× process and performs bubble edge detection, which ensures that all areas inside bubbles are excluded from processing by the invention. Imaging characteristics are degraded inside bubbles and tend to introduce false positive objects. Excluding these areas eliminates such false positives.

The apparatus of the invention checks that cover slip edges are detected and that all areas outside of the area bounded by cover slip edges are excluded from image processing by the 20× process. Since the apparatus of the invention was not trained to recognize artifacts outside of the cover slipped area, excluding these areas eliminates possible false positive results.

The computer system 540 accumulates slide level 20× results for the slide scoring process. The computer system 540 performs image acquisition and ensures that 20× images passed to the apparatus of the inventions for processing conform to image quality and focus specifications. This ensures that no unexpected imaging characteristics occur.

The invention performs three major steps, all of which are described in greater detail below:

Step 1 For each 20× FOV (20× objective magnification field of view), the algorithm segments potential cell nuclei and detects their cytoplasm boundaries. This step is called image segmentation.

Step 2 Next, the algorithm measures feature values—such as size, shape, density, and texture—for each potential cell nucleus detected during Step 1. This step is called feature extraction.

Step 3 The algorithm classifies each detected object in an FOV using the extracted feature values obtained in Step 2. This step is called object classification. Classification rules are defined and derived during algorithm training.

In addition to the object classification, other measures are made during the classification process which characterize the stain of the slide, and measure the confidence of classification.

The single cell identification and classification system of the invention was trained from a cell library of training slides.

The apparatus of the invention uses multiple layers of processing. As image data is processed by the apparatus of the invention, it passes through various stages, with each stage applying filters and classifiers which provide finer and finer discrimination. The result is that most of the clearly normal cells and artifacts are eliminated by the early stages of the classifier. The objects that are more difficult to classify are reserved for the later and more powerful stages of the classifier.

During classifier development, the computer system 540 provides the invention with an image and allocates space for storing the features calculated on each object and the results of the apparatus of the invention. The apparatus of the invention identifies the potential nuclei in the image, computes features for each object, creates results, and stores the results in the appropriate location.

During classifier development, the apparatus of the invention calculates and stores over 100 features associate with each object to be entered into the object classifier training database. Additionally, the apparatus of the invention stores object truth information provided by expert cytologists for each object in the training database. Developers use statistical feature analysis methods to select features of utility for classifier design. Once classifiers have been designed and implemented, the apparatus of the invention calculates the selected features and uses them to generate classification results, confidence values, and stain measures.

Figure 2:
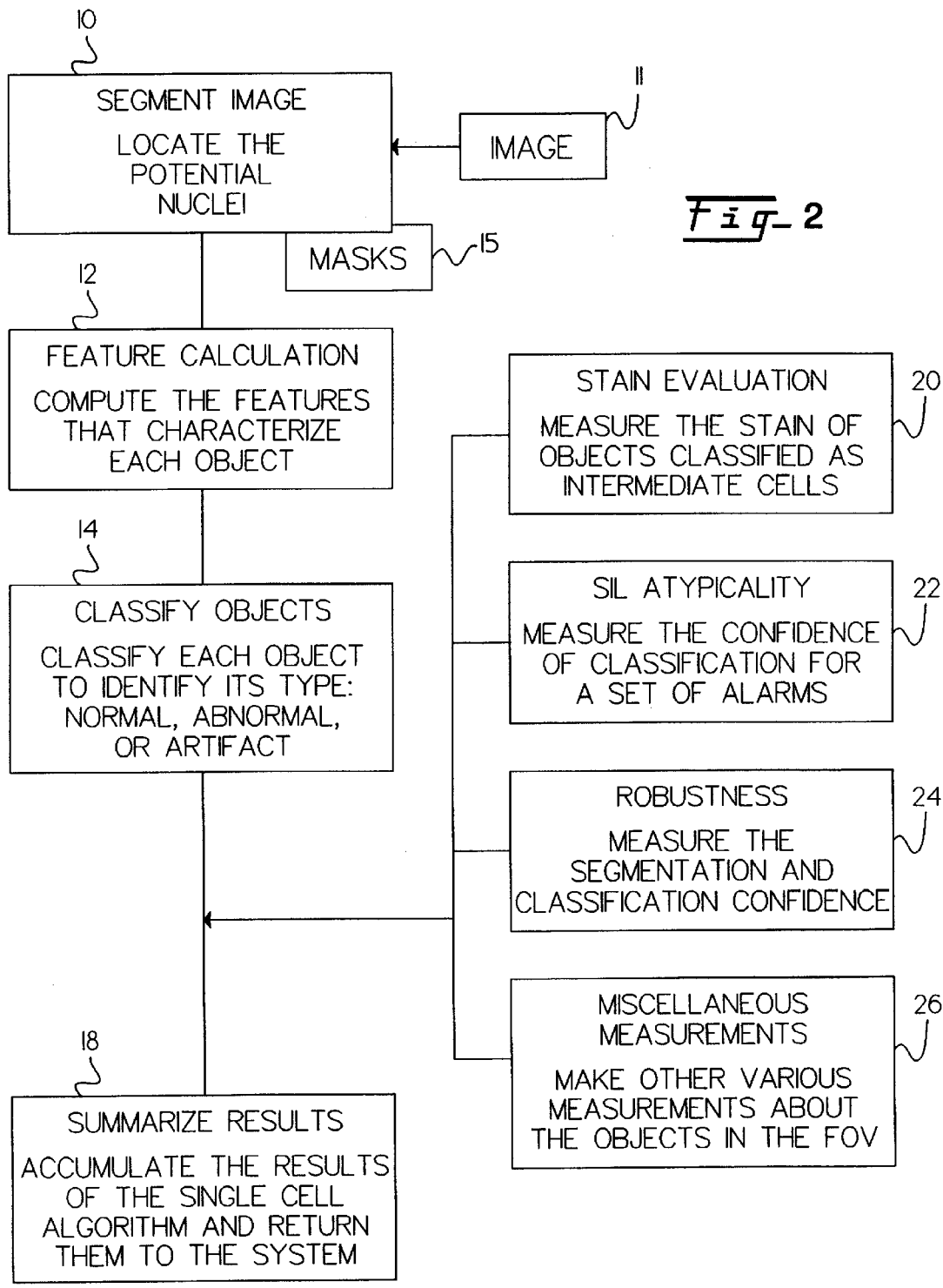
FIG. 2 shows the method of the invention to arrive at a classification result from an image.

Refer now to FIG. 2 which shows the item decomposition steps of the invention. In one embodiment of the invention, the computer system 540 processes a 20× magnification field of view FOV. Steps 10, 12, 14 and 18 are functions that apply to all objects in the image. Steps 20, 22, 24 and 26 are performed only if certain conditions are met. For example, stain evaluation 20 takes place only on objects that are classified as intermediate cells.

The first processing step is image segmentation 10 that identifies objects of interest, or potential cell nuclei, and prepares a mask 15 to identify the nucleus and cytoplasm boundaries of the objects.

Features are then calculated 12 using the original image 11, and the mask 15. The features are calculated in feature calculation step 12 for each object as identified by image segmentation 10. Features are calculated only for objects that are at least ten pixels away from the edge of the image 11. The feature values computed for objects that are closer to the edge of the image 11 are corrupted because some of the morphological features need more object area to be calculated accurately.

Based on the feature calculation step 12, each object is classified in classification step 14 as a normal cell, an abnormal cell, or an artifact. At various stages throughout the classification process, several other measurements are made dependent on the classification results of the objects:

The stain evaluation Step 20 measures stain related features on any object that has been identified as an intermediate cell.

An SIL atypicality process 22 measures the confidence of objects that were classified as potentially abnormal.

A robustness process 24 refers to the segmentation and classification. The robustness process 24 measures identified objects that are susceptible to poor classification results because they are poorly segmented or their feature values lie close to a decision boundary in a classifier.

A miscellaneous measurements process 26 includes histograms of confidences from the classifiers, histograms of the stain density of objects classified as abnormal, or proximity measurements of multiple abnormal objects in one image.

The results of the above processes are summarized in step 18. The numbers of objects classified as normal, abnormal, or artifact at each classification stage are counted, and the results from each of the other measures are totaled. These results are returned to the system where they are added to the results of the other processed images. In total, these form the results of the entire slide.

The 20× magnification images are obtained at Pixel size of 0.55×0.55 microns. The computer 540 stores the address of the memory where the features computed for the objects in the FOV will be stored. The computer also stores the address of the memory location where the results structure resides. This memory will be filled with the results of the invention.

The computer system 540 outputs the following set of data for each field of view:

SEGMENTATION FEATURES

Four features are reported that characterize the segmentation of the image.

SEGMENTED OBJECT COUNT

The number of objects that were segmented in the FOV. This number may be different from the number classified since objects that are too close to the edge of the FOV are not classified.

OBJECT COUNTS OF INITIAL BOX FILTER

The number of objects rejected by each of the five stages of the initial box filter.

OBJECT COUNTS OF STAGE1 CLASSIFIER

The number of objects classified as normal, abnormal, or artifact by Stage1's box classifier, and the number classified as normal, abnormal, or artifact at the end of the Stage1 classifier. (Six numbers are recorded: three for the results of the Stage1 box classifier, and three for the results of the Stage1 classifier.)

OBJECT COUNTS OF STAGE2 CLASSIFIER

The number of objects classified as normal, abnormal, or artifact by Stage2's box classifier, and the number classified as normal, abnormal, or artifact at the end of the Stage2 classifier. (Six numbers are recorded: three for the results of the Stage2 box classifier and three for the results of the Stage2 classifier.)

OBJECT COUNTS OF STAGE3 CLASSIFIER

The number of objects classified as normal, abnormal, or artifact by Stage3's box classifier, and the number classified as normal, abnormal, or artifact at the end of the Stage3 classifier. (Six numbers are recorded: three for the results of the Stage3 box classifier and three for the results of the Stage3 classifier.)

OBJECT COUNT OF STAGE4 CLASSIFIER

The number of objects classified as abnormal by the Stage4 classifier.

OBJECT COUNTS OF PLOIDY CLASSIFIER

Two values are computed: the number of objects classified as abnormal by the first stage of the Ploidy classifier and the number of objects classified as highly abnormal by the second stage of the Ploidy classifier.

OBJECT COUNTS OF STAGE4+PLOIDY CLASSIFIER

Two values are computed: The number of objects classified as abnormal by the Stage4 classifier that were also classified as abnormal by the first stage of the Ploidy classifier, and the number of objects classified as abnormal by the Stage4 classifier that were also classified highly abnormal by the second stage of the Ploidy classifier.

STAGE2/STAGE3/STAGE4/PLOIDY ALARM CONFIDENCE HISTOGRAM

Histograms for the alarm confidence of the Stage2, Stage3, Stage4, and Ploidy alarms detected in an FOV.

STAGE2/STAGE3ALARM COUNT HISTOGRAM

Two histograms for the alarm count histogram of the Stage2 and stage3 alarms detected in an FOV.

STAGE2/STAGE3 ALARM IOD HISTOGRAM

Histograms for the Integrate Optical Density (IOD) of objects classified as abnormal by Stage2 and stage3 in an FOV.

INTERMEDIATE CELL IOD-SIZE SCATTERGRAMS

Two IOD vs. size scattergrams of the normal intermediate cells detected in the FOV.

INTERMEDIATE CELL STAIN FEATURES

Six features are accumulated for each object classified as an intermediate cell. These features are all stain related and are used as reference values in the slide level classification algorithms.

CONTEXTUAL STAGE1 ALARM

Number of Stage1 alarms within a 200 pixel radius of a Stage2 alarm in the same FOV.

CONTEXTUAL STAGE2 ALARM

Number of Stage2 alarms located within a 200 pixel radius of a Stage3 alarm in the same FOV.

ESTIMATED CELL COUNT

An estimate of the number of squamous cells present in the image.

ATYPICALITY INDEX

An 8×8 array of confidences for all objects sent to the atypicality classifier.

SEGMENTATION ROBUSTNESS AND CLASSIFICATION DECISIVENESS

A set of confidence measures that an object was correctly segmented and classified. This information is available for Stage2 and Stage3 alarms.

SINGLE CELL ADDON FEATURES

A set of eight features for each object classified as a Stage3 alarm. This information will be used in conjunction with slide reference features to gauge the confidence of the Stage3 alarms.

Prior to 20× magnification processing an FOV selection and integration process is performed at a 4× magnification scan of the slide to determine the likelihood that each FOV contains abnormal cells. Next, the computer system 540 acquires the FOVs in descending order: from higher likelihood of abnormal cells to lower likelihood.

Image segmentation 10 converts gray scale image data into a binary image of object masks. These masks represent a group of pixels associated with a potential cell nucleus. Using these masks, processing can be concentrated on regions of interest rather than on individual pixels, and the features that are computed characterize the potential nucleus.

The image segmentation process 10 is based on mathematical morphology functions and label propagation operations. It takes advantage of the power of nonlinear processing techniques based on set theoretic concepts of shape and size, which are directly related to the criteria used by humans to classify cells. In addition, constraints that are application specific are incorporated into the segmentation processes of the invention; these include object shape, size, dark and bright object boundaries, background density, and nuclear/cytoplasmic relationships. The incorporation of application-specific constraints into the image segmentation 10 process is a unique feature of the AutoPap® 300 System's processing strategy.

Figure 3A:
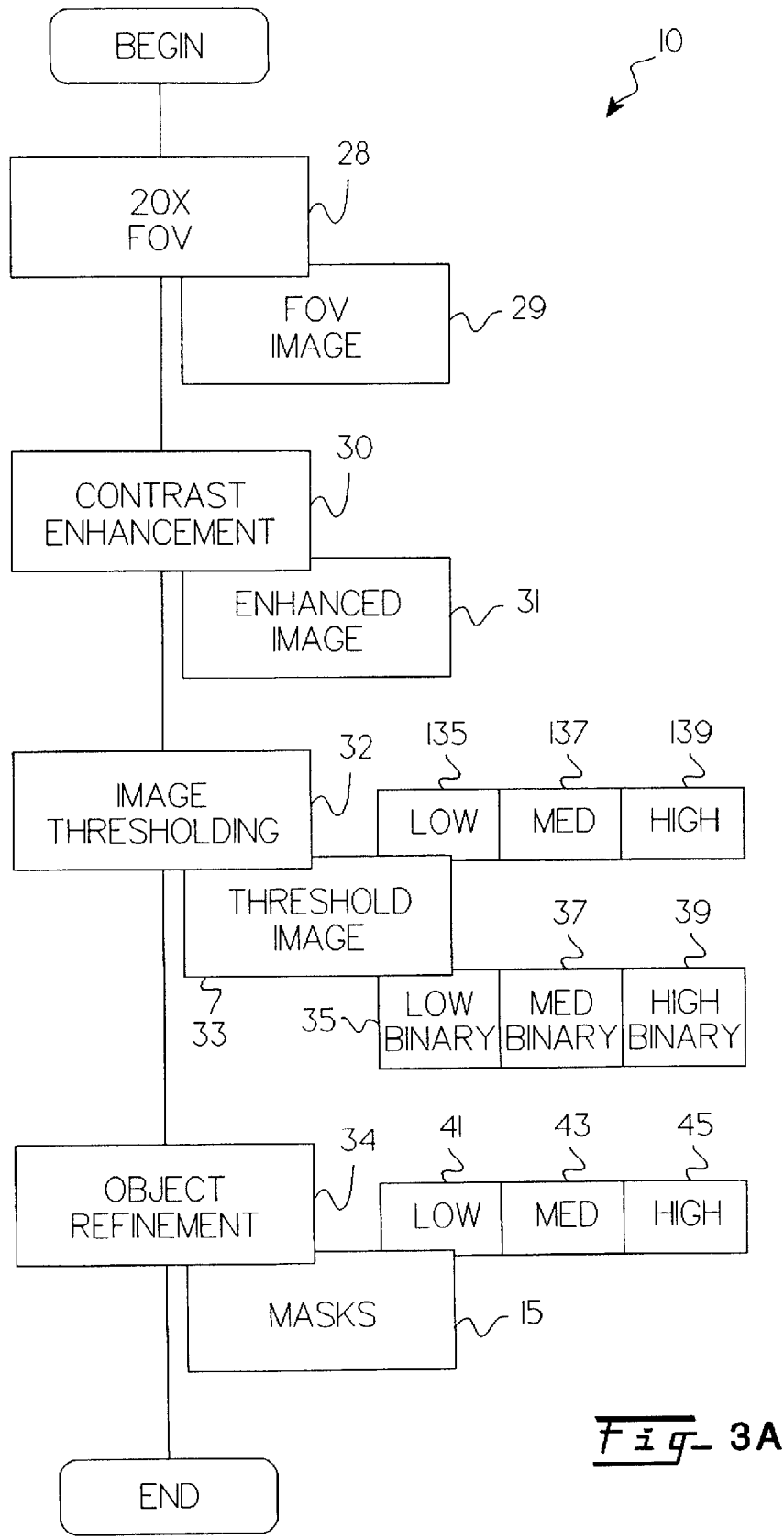
FIG. 3A shows the segmentation method of the invention.

Refer now to FIG. 3A which shows the image segmentation process 10 of the invention in more detail. The image segmentation process is described in U.S. Pat. No. 5,528,703, issued Jun. 18, 1996, which is a continuation in part of abandoned U.S. patent application Ser. No. 07/838,395, entitled "Method for Identifying Objects Using Data Processing Techniques" by Shih-Jong James Lee. For each image 29, the image segmentation process 10 creates a mask which uniquely identifies the size, shape and location of every object in an FOV. There are three steps involved in image segmentation 10 after the 20× image data 29 is received in 20× imaging step 28: contrast enhancement 30, image thresholding 32, and object refinement 34.

During contrast enhancement 30 the apparatus of the invention first enhances, or normalizes, the contrast between potential objects of interest and their backgrounds: bright areas become brighter and dark areas become darker. This phase of processing creates an enhanced image 31. During image thresholding 32 a threshold test identifies objects of interest and creates a threshold image 33. The threshold image 33 is applied to the enhanced image 31 to generate three binary mask images. These binary mask images are further refined and combined by an object refinement process 34 to identify the size, shape, and location of objects. The contrast enhancement process 30 increases the contrast between pixels that represent the object of interest and pixels that represent the background.

Figure 3B:
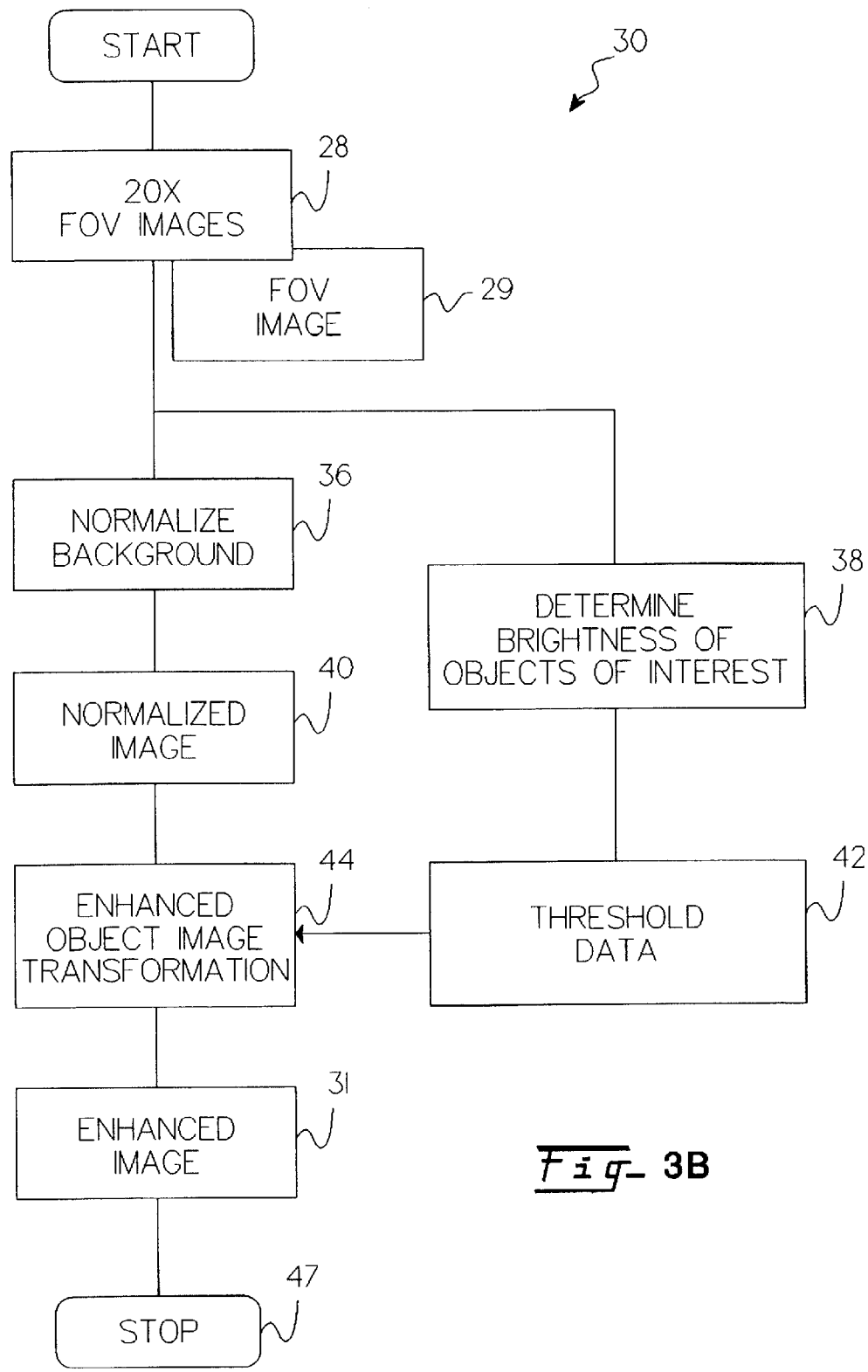
FIG. 3B shows the contrast enhancement method of the invention.

Refer now to FIG. 3B which shows the contrast enhancement process 30 first normalizes the image background 36 by pixel averaging. The contrast enhanced image 31 is derived from the difference between the original image 29 and the normalized background 40 computed in enhanced object image transformation step 44. As part of the image contrast enhancement process 30, each object in the field of view undergoes a threshold test 38 using threshold data 42 to determine whether the brightness of the object lies within a predetermined range. The contrast enhancement process stops at step 47.

At this point, the apparatus of the invention begins to differentiate artifacts from cells so that artifacts are eliminated from further analysis. The apparatus of the invention provides a range of predetermined values for several characteristics, including but not limited to brightness, size and shape of nucleus, cytoplasm and background, of the objects of interest. Objects whose characteristics do not lie within the range of these values are assumed to be artifacts and excluded from further classification.

Figure 3C:
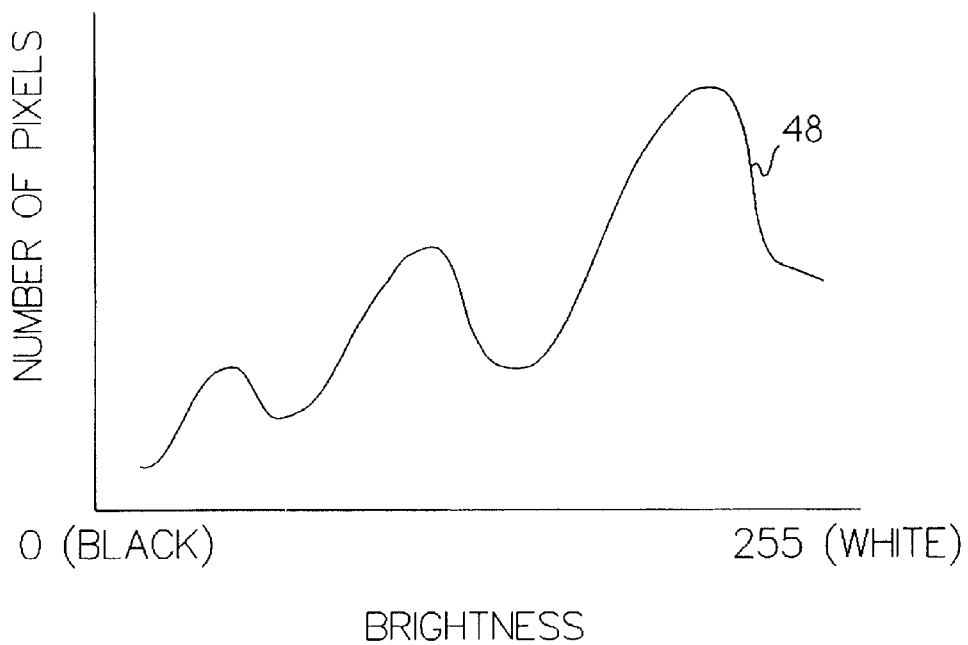
FIGS. 3C and 3D show a plot of pixels vs. brightness.
Figure 3D:
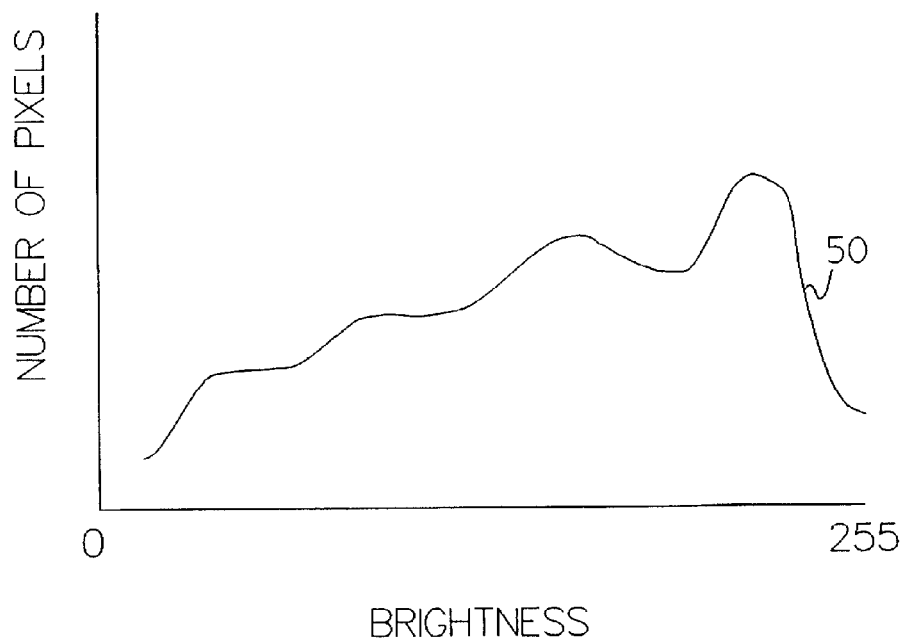

The brightness of an image is provided by histogram functions shown in FIGS. 3C and 3D respectively, which determines how many pixels within a gray scale FOV have a certain image intensity. Ideally, the histogram is a curve 48 having three peaks, as shown in the upper histogram in FIG. 3C. The three peaks correspond to three brightness levels usually found in the images: the background, the cytoplasm, and the nuclei. If the number of pixels of each brightness level were plotted as a histogram, the largest, brightest peak would be the background since this usually makes up the largest portion of the image 29. The medium brightness peak would correspond to the area of cytoplasm, and the darkest and shortest peak would correspond to the cell nuclei.

This ideal representation rarely occurs since overlapped cells and cytoplasm tend to distort the results of the histogram 50 as shown in the lower histogram in FIG. 3D. To reduce the impact of overlapping cells on brightness calculations, the apparatus of the invention applies morphological functions, such as repeated dilations and erosions, to remove overlapped objects from the image before the histogram is calculated.

Referring again to FIG. 3A, in addition to the contrast enhanced image 31, a threshold image 33 is generated by a morphological processing sequence. A threshold test 32 is then performed on the enhanced image using the threshold image 33 to produce a binary image. The threshold test compares each pixel's value to the threshold image pixel value. The apparatus of the invention then identifies as an object pixel any pixel in the enhanced image that has an intensity greater than the corresponding pixel of the threshold value.

The threshold image is combined with two predetermined offset values to generate three threshold images 135, 137 and 139. The first offset is subtracted from each gray scale pixel value of the original threshold image 33 to create a low threshold image. The second offset value is added to each gray scale pixel value of the threshold image to create a high threshold image. Each of these images—medium threshold, which is the original threshold image, low threshold, and high threshold—are separately combined with the enhanced image to provide three binary threshold images: a low threshold binary image 35; a medium threshold binary image 37; and a high threshold binary image 39.

Figure 3E:
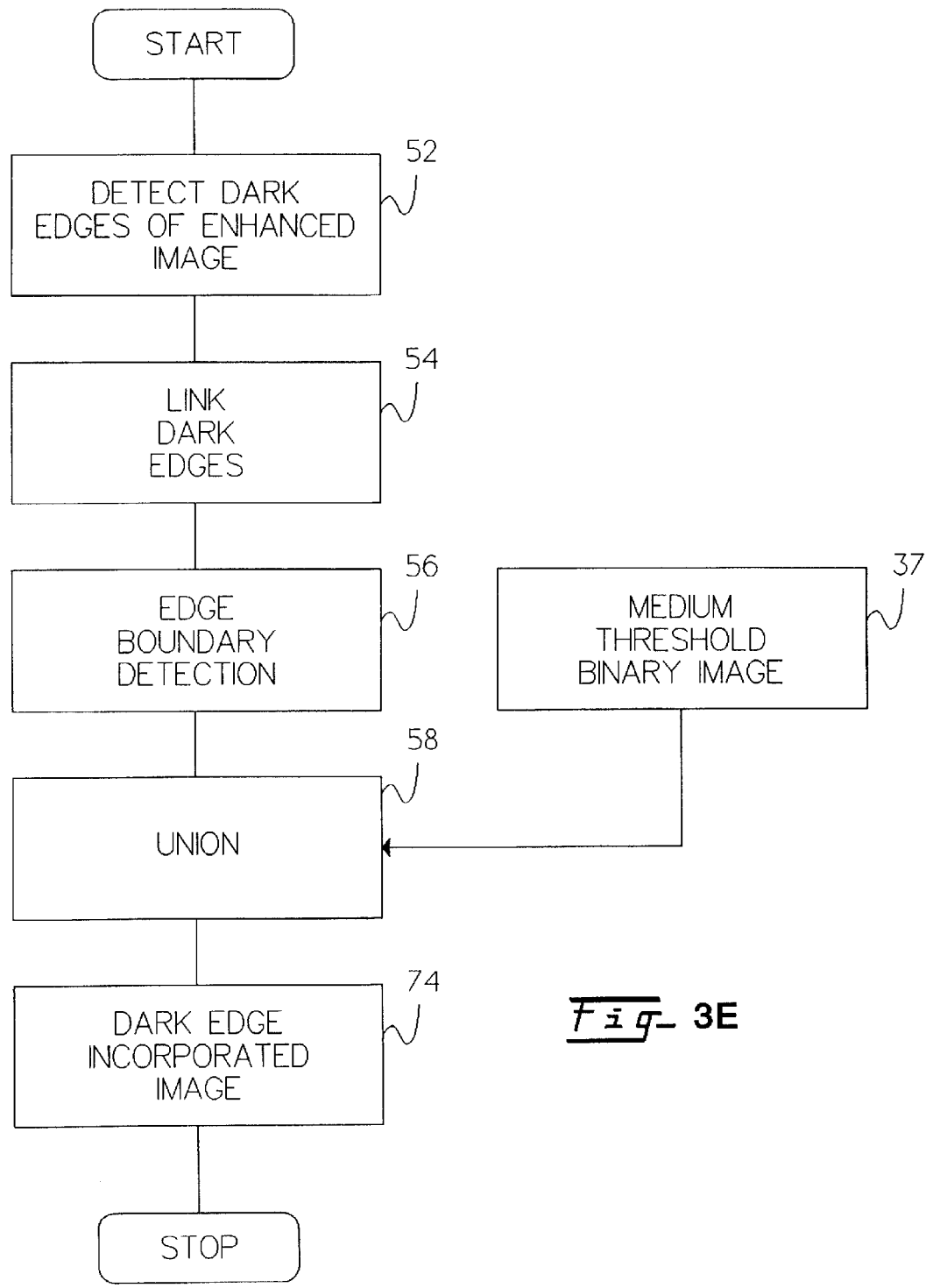
FIG. 3E shows the dark edge incorporated image method of the invention.

Refer now to FIG. 3E where the three binary threshold images are refined, beginning with the medium threshold binary image 37. The medium threshold binary image 37 is refined by eliminating holes and detecting the dark edges 52 of the objects of interest in the enhanced image. Dark edges 54 are linked using a small morphological closing and opening sequence to fill in holes. Dark edges are detected by determining where there is a variation in intensity between a pixel and its neighboring pixels. Thereafter, boundaries of an edge are detected 56 and identified as a true dark edge mask. The medium threshold binary image 37 is then combined in a set union 58 with the edge boundary detected image 56 to create a dark edge incorporated image 74.

As illustrated in FIG. 3F, bright edges 64 of the original image are then excluded from the medium threshold binary image 37. The bright edges of the enhanced image are detected in a manner similar to dark edge detection. The boundary of the dark edge incorporated image 74 is detected and combined with the bright edge enhanced image 64 in a set intersection operation 68. The results are subtracted 70 from the dark edge incorporated image 74 to create a bright edge excluded image 72. The medium threshold binary image 37 is now represented by the bright edge excluded image 72.

Refer to FIGS. 3G, 3H and 3I which show that Objects 80 from the bright edge excluded image 72 are completed by filling any holes 82 that remain. Holes 82 can be filled without the side effect of connecting nearby objects. Small holes 82 are detected and then added to the original objects 80. To further refine the medium threshold binary image 37, the bright edge excluded image 72 is inverted (black becomes white and vice versa). Objects that are larger than a predetermined size are identified and excluded from the image by a connected component analysis operation. The remaining image is then added to the original image, which provides the completed medium threshold binary mask that fills the holes 82.

To complete the medium threshold binary image 37, connected objects that may not have been separated using the bright edge detection process of FIG. 3F are separated. To do so, objects in the medium threshold binary mask 37 are eroded by a predetermined amount and then dilated by a second predetermined amount. The amount of erosion exceeds the amount of dilation so that objects after dilation are smaller than before erosion. This separates connected objects.

A morphological closing residue operation is applied to determine separation boundaries. A separation boundary is subtracted from the hole-filled image to create an overlap object separated binary image. To ensure that no objects have been lost in this process, the overlap object separated image is dilated to generate an object mask. Small objects not included in the object mask are combined in a set union with the object separation image to provide an object recovered image.

Referring again to FIG. 3A, in the last step, the high and low threshold binary images are combined with the object recovered image (the refined medium threshold binary image) to create final object masks 41, 43 and 45. All objects identified in the high threshold binary image 39 are added to the refined medium threshold binary image 37 using a set union operation. The resulting mask is eroded by a small amount and dilated by a large amount, so that all objects are connected to a single object. This mask is combined with the low threshold binary mask 35. Objects in the low threshold binary mask 35 that are not in close proximity to objects in the medium threshold binary mask 37 are added to the image. These objects are added to the refined medium threshold image 43 to create the finished mask. A connected components labeling procedure removes small or oddly shaped objects and assigns a unique label to each remaining connected object.

The segmented image 15 is used by the feature extraction process 12 to derive the features for each object. The features computed are characteristic measures of the object such as size, shape, density, and texture. These measurements are input to the classifiers 14 and allow the apparatus of the invention to discriminate among normal cells, potentially abnormal cells, and artifacts. The features are defined below.

The object classification process 14 consists of a series of classifiers that are grouped in stages. Each stage takes potentially abnormal objects from the previous stage and refines the classification result further using sets of new features to improve the accuracy of classification. At any stage, objects that are classified as normal or artifact are not classified further.

Figure 4A:
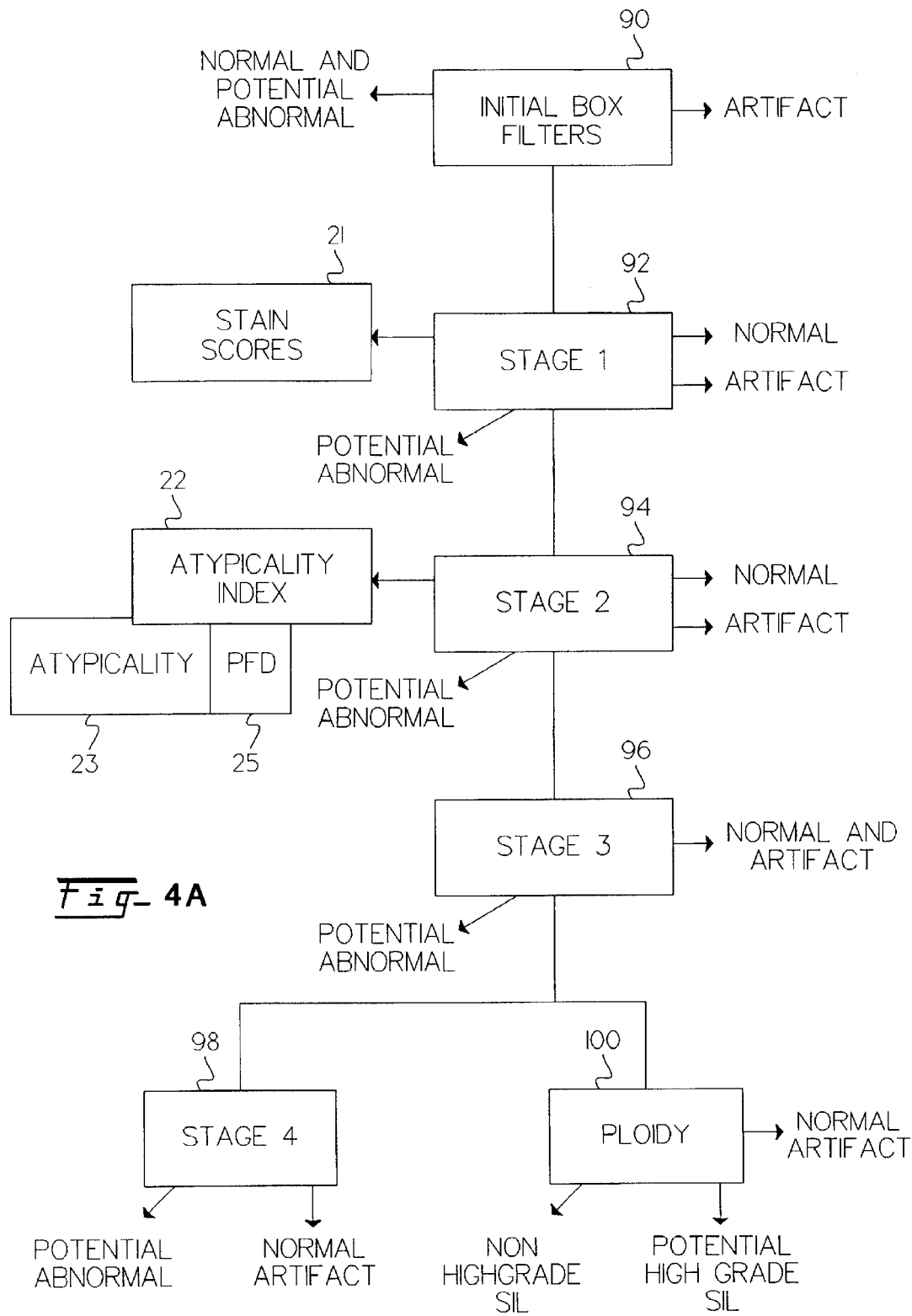
FIG. 4A shows the feature extraction and object classification of the invention.

Now refer to FIG. 4A which shows the classifier process of the invention. Initial Box Filter classifiers 90 discards obvious artifacts. The data then proceeds through classification stage1, stage2, and stage3, classifiers 92, 94, 96 and ends with the Stage4 and Ploidy classifiers 98, 100.

The purpose of the Initial Box Filter classifier 90 is to identify objects that are obviously not cell nuclei, using as few features as possible, features that preferably are not difficult to compute. Only the features required for classifications are computed at this point. This saves processing time over the whole slide. The initial box filter 90 comprises five separate classifiers designed to identify various types of artifacts. The classifiers operate in series as shown in FIG. 4B As an object passes through the initial box filter, it is tested by each classifier shown in FIG. 4B. If it is classified as an artifact, the object classification 14 is final and the object is not sent to the other classifiers. If it is not, the object goes to the next classifier in the series. If an object is not classified as an artifact by any of 5 classifiers 102, 104, 106, 108 and 110, it will go to the Stage1 classifier 92.

Input to the initial box filter 90 comprises a set of feature measurements for each object segmented. The output comprises the following:

The number of objects classified as artifact by each of the classifiers, which results in five numbers.

The Stage1, Stage2, and Stage3 classification codes for each object classified as an artifact.

An "active" flag that indicates whether the object has a final classification. If the object is classified as an artifact, it is not active anymore and will not be sent to other classifiers.

The initial box filter 90 uses 15 features, which are listed in the following table, for artifact rejection. Each classifier within the initial box filter 90 uses a subset of these 15 features. The features are grouped by their properties.

| Feature type | Feature name(s) |
| --- | --- |
| Condensed Feature | condensed_area_percent |
| Context Texture Feature | big_blur_ave |
| Contrast Feature | nc_contrast_orig |
| Density Features | mean_orig_2 |
|  | normalized_mean_od_r3 |
|  | integrated_density_orig |
|  | nuc_bright_sm |
| Nucleus/Cytoplasm Texture Contrast Feature | nuc_edge_5_5_sm |
| Shape Features | compactness |
|  | density_1_2 |
|  | density_2_3 |
| Size Feature | perimeter |
| Texture Features | sd_orig2 |
|  | nuc_blur_sd |
|  | nuc_edge_9_mag |

The initial box filter is divided into five decision rules. Each decision is based on multiple features. If the feature value of the object is outside the range allowed by the decision rule, the object is classified as an artifact. The decision rule for each of the initial box filter classifiers is defined as follows:

Box1 102

```
if (
    perimeter >= 125              OR
    compactness >= 13             OR
    density_2_3 >= 7.5            OR
    density_1_2 >= 10
)
then
    the object is an artifact.
```
Box2 104
```
else if (
    mean_orig2 < 20               OR
    sd_orig2 < 5.3                OR
    sd_orig2 > 22.3
)
then
    the object is an artifact:
```
Artifact Filter for Unfocused Objects and Polies#1 106
```
else if (
    nuc_blur_sd < 1.28            OR
    big_blur_ave < (-1.166 * nuc_blur_sd + 2.89)   OR
```

-continued
```
    big_blur_ave < (4.58 * condensed_area_percent + 0.8)
    OR
    compactness > (-0.136 * nuc_edge_9_mag + 18.05) OR
    nuc_edge_5_5_sm > (-1.57 * compactness + 28.59
    )
then
    the object is an artifact.
```
Artifact Filter for Graphite#2 108
```
else if
    nc_contrast_orig > (-4.162 * normalized_mean_od_r3 +
    615.96)
then
    the object is an artifact.
```
Artifact Filter for Cytoplasm#3 110
```
else if
    integrated_density_orig < (433933.2 * nuc_bright_sm -
    335429.8)
then
    the object is an artifact.
else
    continue the classification process with the Stage 1 Box
    Filter.
```

Up to 40% of objects that are artifacts are identified and eliminated from further processing during the initial box filter 90 processing. This step retains about 99% of cells, both normal and potentially abnormal, and passes them to Stage1 92 for further processing.

Objects that are not classified as artifacts by the classifiers of the initial box filter 90 are passed to Stage1 92, which comprises of a box filter classifier and two binary decision tree classifiers as show in FIG. 4C. The Stage1 box filter 92 is used to discard objects that are obviously artifacts or normal cells, using new features which were not available to the initial box filter 90. The binary decision trees then attempt to identify the abnormal cells using a more complex decision process.

The box filter 112 identifies normal cells and artifacts: the classification of these objects is final. Objects not classified as normal or artifact are sent to Classifier#1 114 which classifies the object as either normal or abnormal. If an object is classified as abnormal, it is sent to Classifier#2 116, where it is classified as either artifact or abnormal. Those objects classified as abnormal by Classifier#2 116 are sent to Stage2 92. Any objects classified as artifact by any of the classifiers in Stage1 92 are not sent to other classifiers.

The input to Stage1 92 comprises of a set of feature measurements for each object not classified as an artifact by the box filters 90.

The output comprises the following:

The numbers of objects classified as normal, abnormal, and artifact by the Stage1 box classifiers, 3 numbers.

The numbers of objects which were classified as normal, abnormal or artifact at the end of the Stage1 classifier 92.

An "active" flag that indicates whether the object has a final classification. If the object has been classified as an artifact, it is not active anymore and is not sent to other classifiers.

The features that are used by each of the Stage1 classifiers 92 are listed in the following tables. They are categorized by their properties.

| Feature type | Feature name(s) |
|---|---|
| Stage1 Box Filter 112 | |
| Condensed Features | condensed_count |
| | condensed_area_percent |
| | condensed_compactness |
| Context Density Feature | mean_background |
| Context Texture Features | small_blur_ave |
| | big_blur_sd |
| | sm_blur_sd |
| Contrast Feature | edge_contrast_orig |
| Density Feature | integrated_density_od |
| Nucleus/Cytoplasm Relation Feature | nc_score_r4 |
| Shape Feature | compactness |
| Texture Feature | texture_correlation3 |
| Stage1, Classifier#1 114 | |
| Condensed Feature | condensed_count |
| Context Texture Features | big_blur_ave |
| | small_edge_9_9 |
| | big_edge_5_mag |
| | big_edge_9_9 |
| | sm_blur_sd |
| Contrast Feature | edge_contrast_orig |
| Density Feature | autothresh_enh |
| Nucleus/Cytoplasm Relation Features | mod_N_C_ratio |
| | cell_nc_ratio |
| | nc_score_alt_r3 |
| Nucleus/Cytoplasm Texture Contrast Feature | nuc_edge_2_mag_big |
| Shape Features | compactness2 |
| | density_0_1 |
| | inertia_2_ratio |
| Texture Features | cooc_inertia_4_0 |
| | sd_orig |
| | nonuniform_run |
| | nuc_edge_2_mag |
| | nuc_blur_sk |
| | sd_enh2 |
| | edge_density_r3 |
| | cooc_homo_1_0 |
| Stage1, Classifier#2 116 | |
| Context Density Feature | big_bright |
| Context Texture Features | big_edge_2_dir |
| | big_edge_9_9 |
| Contrast Feature | edge_contrast_orig |
| Density Features | mod_nuc_IOD_sm |
| | integrated_density_orig2 |
| | mod_nuc_OD_sm |
| | normalized_integrated_od |
| | normalized_mean_od |
| Nucleus/Cytoplasm Relation Features | nc_score_r4 |
| | cell_semi_isolated |
| | mod_N_C_ratio |
| Nucleus/Cytoplasm Texture Contrast Features | nuc_edge_9_mag_sm, |
| | nuc_edge_9_9_big |
| Shape Feature | area_inner_edge |
| Size Feature | perimeter |
| Texture Features | edge_density_r3 |
| | nuc_blur_ave |
| | below_autothresh_enh2 |
| | cooc_energy_4_0 |
| | cooc_entropy_1_135 |
| | nuc_edge_2_dir |
| | cooc_corr_90 |
| | texture_inertia3 |

The decision rules used in each classifier are defined as follows:

Box Filter 112 if (
   integrated_density_od <= 17275.5 AND
   sm_blur_ave <= 4.98465   AND
   edge_contrast_orig <= −42.023
)
then
   the object is normal
else if (
   condensed_count <= 3.5   AND
   compactness <= 10.6828   AND
   sm_blur_ave <= 3.0453   AND
   integrated_density_od <= 19925   AND
   condensed_area_percent > 0.0884
)
then
   the object is an artifact
else if (
   condensed_count <= 3.5   AND
   compactness > 10.6828   AND
   condensed_compactness <= 19.5789
)
then
   the object is an artifact
else if (
   integrated_density_od <= 22374   AND
   big_blur_sd <= 3.92333   AND
   sm_blur_sd <= 1.89516
)
then
   the object is normal
else if (
   integrated_density_od <= 22374   AND
   big_blur_sd <= 3.92333   AND
   sm_blur_sd > 1.89516   AND
   nc_score_r4 <= 0.36755   AND
   texture_correlation3 <= 0.7534   AND
   mean_background > 226.66
)
then
   the object is normal
else if (
   integrated_density_od <= 22374   AND
   big_blur_sd <= 3.92333   AND
   sm_blur_sd > 1.89516   AND
   nc_score_r4 <= 0.36755   AND
   texture_correlation3 > 0.7534
)
then
   the object is normal
else if (
   integrated_density_od <= 10957.5 AND
   big_blur_sd _= 3.92333   AND
   sm_blur_sd > 1.89516   AND
   nc_score_r4 > 0.36755
)
then
   the object is normal
else
   the object continues the classification process in
   Stage1, Classifier1.

Stage1, Classifier#1 114

This classifier is a binary decision tree that uses a linear feature combination at each node to separate normal cells from abnormal cells. The features described in the previous tables make up the linear combination. The features are sent to each node of the tree. The importance of each feature at each of the nodes may be different and was determined during the training process.

Stage1, Classifier#2 116

This classifier is a binary decision tree that uses a linear feature combination at each node to separate artifacts from abnormal cells. The features that make up the tree are listed in a previous table.

A significant proportion of the objects classified as abnormal by Stage1 92 are normal cells and artifacts. Stage2 94 attempts to remove these, leaving a purer set of abnormal cells. Stage2 94 comprises a box filter 118, which discards objects that are obviously artifacts or normal cells, and two binary decision trees shown in FIG. 4D.

The objects classified as abnormal by Stage1 92 enter Stage2 94. The box filter 118 identifies normal cells and artifacts; the classification of these objects is final. Objects not classified as normal or artifact are sent to Classifier#1 120, which classifies the object as either normal or abnormal. If an object is classified as abnormal, it is sent to Classifier#2 122, where it is classified as either artifact or abnormal. Those objects classified as abnormal by Classifier#2 122 are sent to Stage3 96. Any objects classified as normal or artifact by one of the classifiers in Stage2 94 are not sent to other classifiers.

The input to Stage2 94 comprises of a set of feature measurements for each object classified as abnormal by Stage1. The output comprises the following:

- The numbers of objects classified as normal, abnormal, and artifact by the box filter (3 numbers)
- The numbers of objects which were classified as normal, abnormal or artifact at the end of the Stage2 94 classifier.
- An "active" flag, which indicates whether the object a final classification. (If it has been classified as artifact or normal it is not active anymore, and will not be sent to other classifiers.)

Features Required by the Stage2 94 Classifiers

The features that are used by each of the Stage2 94 classifiers are listed in the following tables. They are categorized by feature properties.

| Feature type | Feature name(s) |
| --- | --- |
| Stage2 94 Box Filter | |
| Condensed Features | condensed_avg_area |
| | condensed_compactness |
| Context Density Features | mean_background |
| Context Texture Features | sm_blur_sd |
| | big_blur_ave |
| | sm_blur_ave |
| Contrast Feature | nc_contrast_orig |
| Density Features | integrated_density_od |
| | integrated_density_od2 |
| | normalized_integrated_od_r3 |
| Shape Features | compactness |
| | shape_score |
| Texture Features | nuc_blur_sd |
| | texture_inertia4 |
| | texture_range4 |
| | edge_density_r3 |
| Stage2 94, Classifier 1 | |
| Context Texture Features | sm_blur_ave |
| | big_edge_2_dir |
| | big_edge_5_mag |
| | big_blur_ave |
| | big_edge_9_9 |
| | big_edge_3_3 |
| Density Feature | min_od |
| Shape Feature | sbx (secondary box test) |
| Size Features | area_inner_edge |
| | area |
| | nuclear_max |
| | perimeter2 |
| Texture Features | nuc_blur_ave |
| | nuc_blur_sk |
| Stage2 94, Classifier 2 | |
| Condensed Feature | condensed_count |
| Context Density Features | mean_background |
| | mean_outer_od |
| Contrast Features | edge_contrast_orig |
| | nc_contrast_orig |
| Density Features | nuc_bright_big |
| | mod_nuc_OD_big |

-continued

| Feature type | Feature name(s) |
| --- | --- |
| Shape Features | compactness2 |
| | density_0_1 |
| Texture Features | nuc_edge_9_mag |
| | nuc_blur_ave |
| | sd_orig2 |
| | nuc_blur_sd |
| | nuc_edge_2_mag |

Figure 4D:
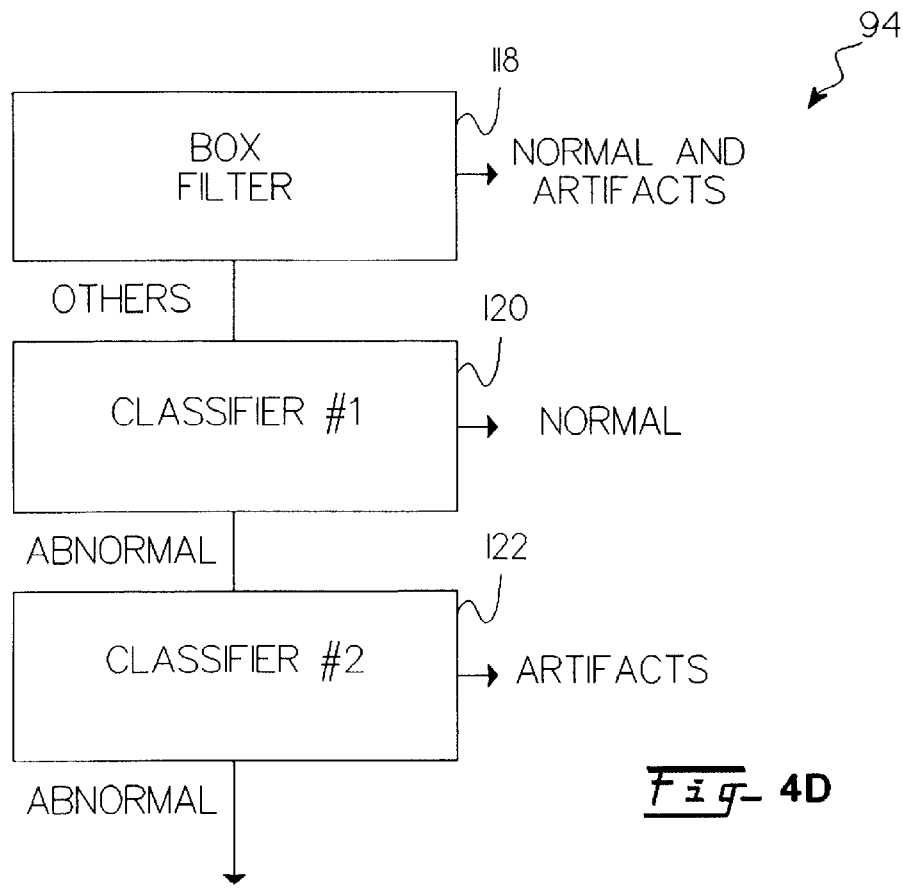
FIG. 4D shows a stage 2 classifier.

The Stage2 94 classifier comprises a box filter and two binary decision trees as shown in FIG. 4D. The decision rules used in each classifier are defined as follows:

Box Filter 118

```
if (
    condensed_avg_area <= 9.4722 AND
    mean_background > 235.182
)
then
    the object is normal
else if (
    condensed_avg_area > 9.4722 AND
    condensed_compactness <= 30.8997 AND
    nuc_blur_sd <= 5.96565 AND
    mean_background <= 233.45 AND
    compactness > 10.4627 AND
    texture_inertia4 <= 0.3763
)
then
    the object is normal
else if (
    integrated_density_od <= 30253 AND
    condensed_compactness <= 22.0611 AND
    sm_blur_sd <= 6.51617 AND
    shape_score <= 38.8071 AND
    texture_range4 <= 72.5 AND
    integrated_density_od > 15558.5
)
then
    the object is an artifact
else if (
    integrated_density_od <= 26781.5 AND
    edge_density_r3 <= 0.29495 AND
    mean_background > 233.526
)
then
    the object is an artifact
else if (
    integrated_density_od2 <= 23461 AND
    normalized_integrated_od_r3 <= 11176.7 AND
    big_blur_ave <= 5.0609 AND
    nc_contrast_orig > 37.1756 AND
    sm_blur_ave <= 3.0411
)
then
    the object is normal
else
    continue the classification process with Stage2 94,
    Classifier#1 120
```

Stage2 Classifier#1 120

This classifier is a binary decision tree that uses a linear feature combination at each node to separate normal cells from abnormal cells. The features used in the tree are listed in a previous table.

Stage2 Classifier#2 122

This classifier is a binary decision tree that uses a linear feature combination at each node to separate artifacts from abnormal cells. The features used in the tree are listed in a previous table.

Figure 4E:
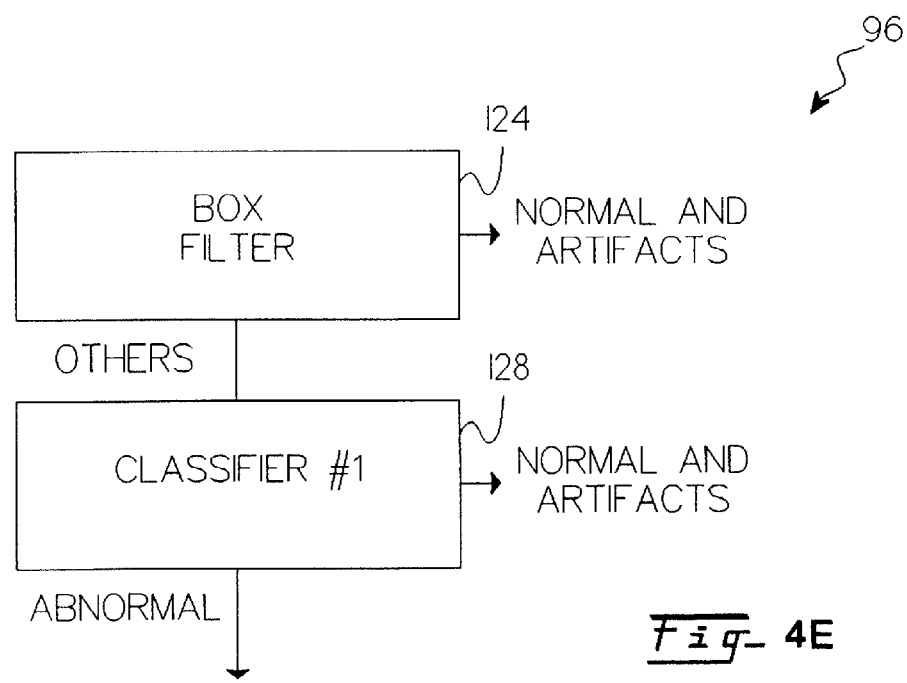
FIG. 4E shows a stage 3 classifier.

A portion of the objects classified as abnormal cells by the Stage2 94 classifier are normal cells and artifacts; therefore, the stage3 96 classifier tries to remove those, leaving a purer set of abnormal cells. A box filter discards objects that are obviously artifacts or normal cells. The box filter is followed by a binary decision tree shown in FIG. 4E.

The objects classified as abnormal by Stage2 94 enter stage3 96. The box filter 124 identifies normal cells and artifacts: the classification of these objects is final. Objects not classified as normal or artifact are sent to the classifier 128, which classifies the object as either normal/artifact or abnormal. If an object is classified as abnormal, it is sent to both stage4 98 and the Ploidy classifiers. Any objects classified as normal or artifact by one of the classifiers in stage3 96 are not sent to other classifiers.

Input to stage3 96 comprises of a set of feature measurements for each object classified as abnormal by Stage2 94. Outputs comprise the following:

The numbers of objects classified as normal, abnormal, and artifact by the box filter, 3 numbers.

The number of objects classified as normal, abnormal or artifact at the end of the stage3 96 classifier.

An "active" flag that indicates whether the object has a final classification. If an object has been classified as a normal or artifact, it is not active anymore and will not be sent to other classifiers.

The features that are used by each of the stage3 96 classifiers are listed in the following tables. They are categorized by feature properties.

| Stage3 Box Filter 124 | |
|---|---|
| Feature type | Feature name(s) |
| Condensed Feature | condensed_area_percent |
| Context Density Features | mean_background |
| | mean_outer_od |
| Context Distance Feature | cytoplasm_max |
| Context Texture Features | big_blur_sk |
| | big_blur_ave |
| | big_edge_2_dir |
| | small_blur_sd |
| Density Feature | integrated_density_od |
| Nucleus/Cytoplasm Relation Feature | cell_semi_isolated |
| Shape Features | shape_score |
| | density_0_1 |
| Size Features | perimeter |
| | area |
| Texture Features | nonuniform_gray |
| | sd_enh |
| | nuc_blur_sd |
| | texture_range |

| Stage3 Classifier 128 | |
|---|---|
| Feature type | Feature name(s) |
| Condensed Feature | condensed_compactness |
| Context Density Features | mean_outer_od |
| | mean_background |
| | mean_outer_od_r3 |
| Context Texture Features | big_blur_ave |
| | big_edge_5_mag |
| | sm_edge_9_9 |
| Density Feature | min_od |
| Shape Feature | sbx |
| Texture Features | nuc_edge_2_mag |
| | cooc_correlation_1_0 |
| | cooc_inertia_2_0 |
| | nonuniform_gray |

The stage3 96 classifier is composed of a box filter and a binary decision tree. The decision rules used in each classifier are as follows:

Box Filter 124

```
if (
    perimeter <= 54.5 AND
    mean_background <= 225.265 AND
    big_blur_sk > 1.33969 AND
    mean_background <= 214.015
    )
then
    the object is an artifact
else if (
    nonuniform_gray <= 44.5557 AND
    big_blur_ave > 2.91694 AND
    area <= 333.5 AND
    sd_enh > 11.7779 AND
    nuc_blur_sd > 3.53022 AND
    cytoplasm_max <= 11.5
    )
then
    the object is an artifact
else if (
    nonuniform_gray <= 35.9632 AND
    mean_background <= 225.199 AND
    integrated_density_od <= 31257.5 AND
    texture_range <= 76.5 AND
    condensed_area_percent <= 0.10055
    )
then
    the object is an artifact
else if (
    nonuniform_gray <= 44.4472 AND
    mean_background <= 226.63 AND
    integrated_density_od <= 32322.5 AND
    cell_semi_isolated > 0.5
    )
then
    the object is an artifact
else if (
    nonuniform_gray <= 44.4472 AND
    mean_background <= 226.63 AND
    integrated_density_od <= 32322.5 AND
    cell semi_isolated <= 0.5 AND
    shape_score <= 69.4799 AND
    texture_range > 75.5
    )
then
    the object is an artifact
if the object was just classified as an artifact:
(
    if
        big_edge_2_dir <= 0.3891
    then
        the object is abnormal
    else if (
        big_edge_2_dir <= 0.683815 AND
        cytoplasm_max <= 22.5 AND
        mean_background <= 223.051 AND
        sm_blur_sd <= 4.41098 AND
        mean_outer_od <= 38.6805
        )
    then
        the object is abnormal
    else if (
        big_edge_2 dir <= 0.683815 AND
        density_0_1 > 27.5
        )
    then
        the object is abnormal
    else if (
        area > 337.5 AND
        mean_background > 223.66
        )
    then
        the object is abnormal
)
if
    the object was classified as abnormal
```

-continued

| Box Filter 124 |
|---|
| then |
|    continue the classification process with the stage3 96 |
|    Classifier. |

Stage3 Classifier 128

This classifier is a binary decision tree that uses a linear feature combination at each node to separate normal cells and artifacts from abnormal cells. The features are listed in a previous table.

Figure 4F:
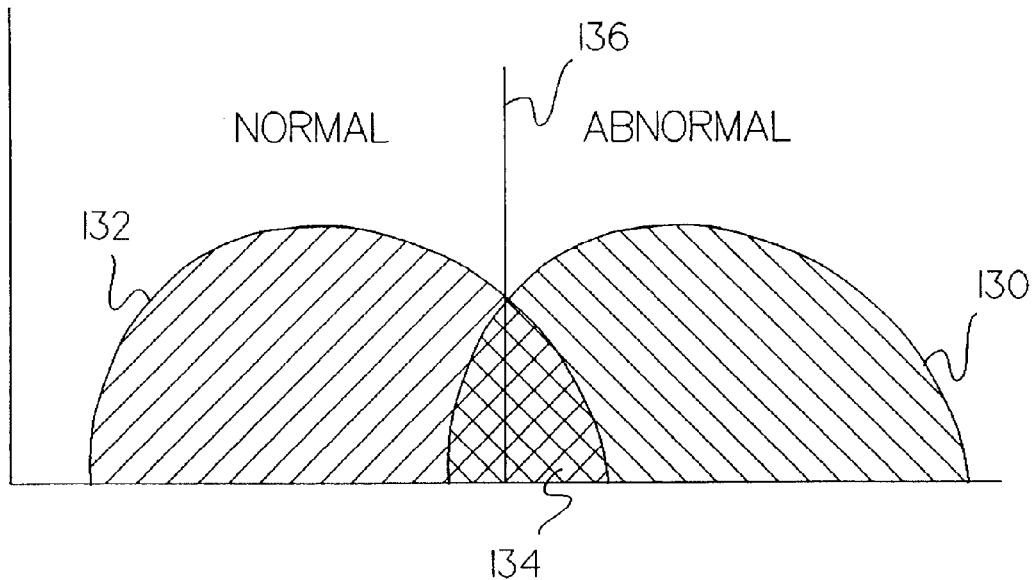
FIGS. 4F and 4G show an error graph.

The main purpose of Stage1–Stage3 is to separate the populations of normal cells and artifacts from the abnormal cells. To accomplish this, the decision boundaries 136 of the classifiers were chosen to minimize misclassification for both populations as shown, for example, in FIG. 4F.

The number of normal cells and artifacts on a given slide are far greater than the number of abnormal cells, and although the misclassification rate for those objects is far lower than it is for the abnormal cells, the population of objects classified as abnormal by the end of the stage3 96 classifier still contain some normal cells and artifacts For example: assume that the misclassification rate for normal cells is 0.1%, and 10% for abnormal cells. If a slide contains 20 abnormal cells and 10,000 normal/artifact objects, the number of objects classified as abnormal would be 0.001*10,000 or 10 normal/artifact objects, and 20*0.9 or 18 abnormal objects. The noise in the number of abnormal objects detected at the end of the stage3 96 classifier makes it difficult to recognize abnormal slides.

Figure 4G:
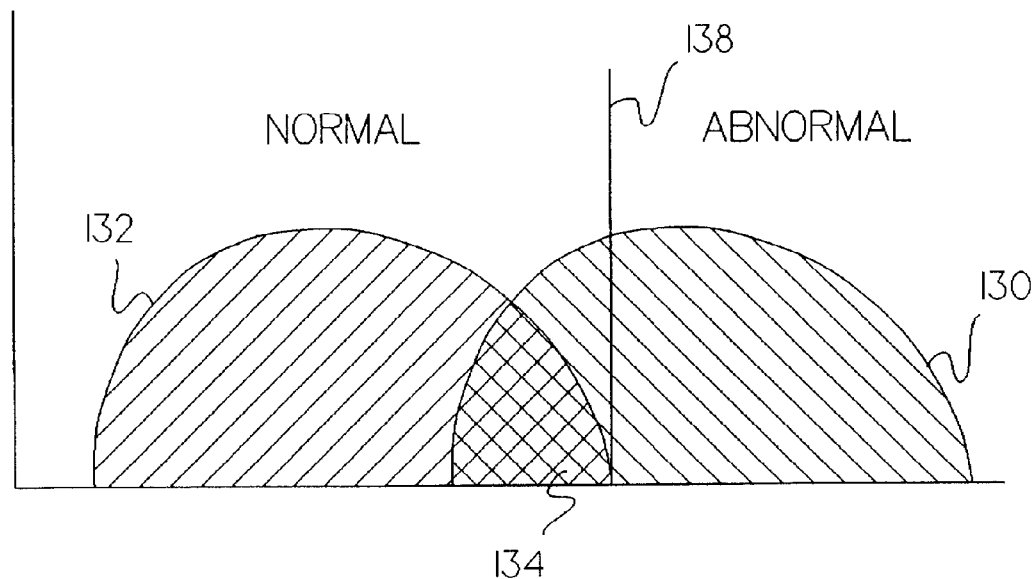

The stage4 98 classifier uses a different decision making process to remove the last remaining normal/artifact objects from the abnormal population. Stage4 98 takes the population existing after stage3 96 and identifies the clearly abnormal population with a minimum misclassification of the normal cells or artifacts. To do this, a higher number of the abnormal cells are missed than was acceptable in the earlier stages, but the objects that are classified as abnormal do not have normal cells and artifacts mixed in. The decision boundary 138 drawn for the stage4 98 classifier is shown in FIG. 4G.

Stage4 is made up of two classifiers. The first classifier was trained with data from stage3 96 alarms. A linear combination of features was developed that best separated the normal/artifact and abnormal classes. A threshold was set as shown in FIG. 4G that produced a class containing purely abnormal cells 130 and a class 134 containing a mix of abnormal, normal, and artifacts.

The second classifier was trained using the data that was not classified as abnormal by the first classifier. A linear combination of features was developed that best separated the normal/artifact and abnormal classes. This second classifier is used to recover some of the abnormal cells lost by the first classifier.

The input to stage4 98 comprises of a set of feature measurements for each object classified as abnormal by stage3 96.

The output comprises of the classification result of any object classified as abnormal by stage4 98.

The features that are used by each of the stage4 98 classifiers are listed in the following table. There are two decision rules that make up the stage4 98 classifier. Each uses a subset of the features listed.

| Feature type | Feature name(s) |
|---|---|
| Condensed Features | condensed_compactness |
| Context Texture Features | big_blur_ave |
| | nuc_blur_sd_sm |
| | big_edge_5_mag |
| Density Features | nuc_bright_big |
| | normalized_integrated_od_r3 |
| | normalized_integrated_od |
| Nucleus/Cytoplasm Texture Contrast Features | nuc_edge_9_9_big |
| Texture Features | nonuniform_gray |
| | texture_range4 |
| | below_autothresh_enh2 |

Decision Rules of Stage4 98
  The classifier follows these steps:
  1 Create the first linear combination of feature values.
  2 If the value of the combination is $\geq$ a threshold, the object is classified as abnormal, otherwise it is classified as normal.
  3 If the object was classified as normal, create the second linear combination.
  4 If the value of this second combination is greater than a threshold, the object is classified as abnormal, otherwise it is classified as normal.

| combination1 = | nonuniform_gray * 2.047321387e-02 + |
|---|---|
| | big_blur_ave * 6.059888005e-01 + |
| | nuc_edge_9_9_big * -8.407871425e-02 + |
| | big_edge_5_mag * -3.132035434e-01 + |
| | nuc_blur_sd_sm * 7.260803580e-01 | if combination1 $\geq$ 3.06, the object is abnormal.
if combination1 < 3.06, compute combination2:

| combination2 = | condensed_compactness * 2.957029501e-03 + |
|---|---|
| | nonuniform_gray * 7.682010997e-03 + |
| | below_autothresh_enh2 * 3.975555301e-01 + |
| | nuc_bright_big * -9.175372124e-01 + |
| | normalized_integrated_od_r3 * -4.740774966e-05 + |
| | normalized_integrated_od * 4.612372868e-05 + |
| | texture_range4 * -2.707793610e-03 | if combination2>=-0.13 the object is abnormal

High grade SIL and cancer cells are frequently aneuploid, meaning that they contain multiple copies of sets of chromosomes. As a result, the nuclei of these abnormal cells stain very dark, and therefore, should be easy to recognize. The ploidy classifier 100 uses this stain characteristic to identify aneuploid cells in the population of cells classified as abnormal by the stage3 96 classifier. The presence of these abnormal cells may contribute to the final decision as to whether the slide needs to be reviewed by a human or not.

The ploidy classifier 100 is constructed along the same lines as the stage4 98 classifier: it is trained on stage3 96 alarms. The difference is that this classifier is trained specifically to separate high grade SIL cells from all other cells; normal, other types of abnormals, or artifacts.

The ploidy classifier 100 is made up of two simple classifiers. The first classifier was trained with data from stage3 96 alarms. A linear combination of features was developed that best separated the normal/artifact and abnormal classes. A threshold was set that produced a class containing purely abnormal cells and a class containing a mix of abnormal, normal, and artifacts.

The second classifier was trained using the data classified as abnormal by the first classifier. A second linear combination was created to separate aneuploid cells from other types of abnormal cells.

The input to the ploidy classifier 100 comprises of a set of feature measurements for each object classified as abnormal by stage3 96.

The output comprises of the classification results of any object classified as abnormal by either classifier in the ploidy classifier 100.

The features used by each of the ploidy classifiers 100 are listed in the following table. There are two decision rules that make up the ploidy classifier 100. Each uses a subset of the features listed.

| Feature type | Feature name(s) |
| --- | --- |
| Context Texture Features | big_edge_5_mag |
|  | big_edge_9_9 |
|  | big_blur_ave |
| Density Features | normalized_integrated_od |
|  | nuc_bright_big |
|  | max_od |
| Density/Texture Features | auto_mean_diff_orig2 |
| Nucleus/Cytoplasm Relation Features | mod_N_C_ratio |
|  | nc_score_r4 |
| Texture Features | nonuniform_gray |
|  | texture_range4 |
|  | nuc_blur_sk |

Ploidy 100 Decision Rules

The classifier follows these steps:

1 Create a linear combination of feature values.

2 If the value of the combination is >= a threshold, the object is classified as abnormal.

3 If the object was classified as abnormal, create a second linear combination.

4 If the value of this second combination is greater than a threshold, the object is classified as aneuploid, or highly abnormal.

```
combination1 =  nonuniform_gray * 7.005183026e-03 +
                auto_mean_diff_orig2 * -1.776645705e-02 +
                mod_N_C_ratio * 2.493939400e-01 +
                nuc_bright_big * -9.405089021e-01 +
                normalized_integrated_od * -2.770500259e-06 +
                big_blur_ave * 1.802701652e-01 +
                big_edge_5_mag * -8.586113900e-02 +
                big_edge_9_9 * -1.906895824e-02 +
                nuc_blur_sk * -1.124482527e-01 +
                max_od * -1.787280198e-03;
``` if combination1≧-0.090, the object is classified as abnormal.

```
combination2 =  big_blur_ave * 2.055980563e-01 +
                texture_range4 * -1.174426544e-02 +
                nc_score_r4 *9.785660505e-01;
``` if combination2≧0.63, the object is classified as aneuploid.

The ploidy classifier 100 was trained on the same data set as the stage4 98 classifier: 861 normal cells or artifacts, and 1654 abnormal cells, composed of 725 low grade SIL, and 929 high grade SIL. All objects were classified as abnormal by the stage3 96 classifier.

The first classifier correctly identified 31.6% of the abnormal object, and mistakenly classified 9.4% of the normal cells and artifacts as abnormal.

The second classifier was trained on all objects which were classified as abnormal by the first classifier: 81 normal cells or artifacts, 124 low grade SIL cells, and 394 high grade SIL cells. The features were selected to discriminate between low grade and high grade cells, ignoring the normal cells and artifacts. The threshold was set using the low grade, high grade, normal cells and artifacts. It correctly classified 34.3% of the high grade SIL cells, and mistakenly classified 14.3% of the low grade, normal cells or artifacts as abnormal cells. Or, it classified 26.8% of the abnormal cells as high grade SIL, and 30.9% of the normal cells or artifacts as high grade SIL.

The purpose of stain evaluation 20 is to evaluate the quality of stain for a slide and to aid in the classification of the slide. The stain evaluation 20 for each FOV is accumulated during the 20× slide scan. This information is used at the end of the slide scan to do the following:

Judge the Quality of the Stain.

If the stain of a slide is too different from that of the slides the apparatus of the inventions were trained on, the performance of the classifier may be affected, causing objects to be misclassified.

Aid in the Classification of the Slide.

The stain features derived from the intermediate cells may be used to normalize other slide features, such as the density features measured on objects classified as abnormal. This will help verify whether the objects classified as abnormal are true abnormal cells or false alarms.

Refer again to FIGS. 2 and 4A, the stain evaluation process 20 is composed of a classifier to identify intermediate cells and a set of stain-related features measured for those cells. Intermediate cells were chosen for use in the stain evaluation 20 because they have high prevalence in most slides, they are easily recognized by the segmentation process, and their stain quality is fairly even over a slide.

The intermediate cell classifier is run early in the process of the invention, before the majority of the normal cells have been removed from consideration by the classifiers. For this reason, the classifier takes all of the cells classified as normal from the Stage1 box classifier 112 and determines whether the cell is an intermediate cell or not.

The intermediate cell classifier takes all objects identified as normal cells from the Stage1 Box classifier 112 and determines which are well segmented, isolated intermediate cells. The intermediate cells will be used to measure the quality of staining on the slide, so the classifier to detect them must recognize intermediate cells regardless of their density. The intermediate cell classifier contains no density features, so it is stain insensitive.

The features used by the intermediate cell classifier are listed in the following table.

| Feature type | Feature name(s) |
| --- | --- |
| Nucleus/Cytoplasm Relation Features | mod_N_C_ratio |
|  | nc_score_alt_r4 |
|  | cell_semi_isolated |
| Nuclear Texture Features | nuc_blur_ave |
| Context Texture Feature | big_blur_ave |
| Nuclear Size Feature | area2 |
| Shape Features | compactness |
|  | area_inner_edge |

The intermediate cell classifier is composed of two classifiers. The first classifier is designed to find intermediate cells with a very low rate of misclassification for other cell types. It is so stringent, it only classifies a tiny percentage of the intermediate cells on the slide as intermediate cells.

To expand the set of cells on which to base the stain measurements, a second classifier was added that accepts more cells such that some small number of cells other than those of intermediate type may be included in the set.

The following are the decision rules for the first and second classifiers:
if
(mod_N_C_ratio≦0.073325 and
nc_score_alt_r4≦0.15115 and
nuc_blur_ave>4.6846 and
big_blur_ave≦4.5655 and
area2>96.5 and
cell_semi_isolated>0.5 and
compactness≦10.2183)
the object is an intermediate cell according to the first classifier;
if
(mod_N_C_ratio≦0.073325 and
nc_score_alt_r4≦0.15115 and
nuc_blur_ave>4.6846 and
big_blur_ave≦4.5655 and
area2>96.5 and
cell_semi_isolated≦0.5 and
area_inner_edge≦138.5)
the object is an intermediate cell according to the second classifier.

The stain score generator 20 takes the objects identified as intermediate squamous cells by the Intermediate Cell classifier, fills in histograms according to cell size and integrated optical density, and records other stain related features of each cell.

The features used by the stain score generator 21 are listed in the following table.

| Feature type | Feature name(s) |
| --- | --- |
| Nuclear Optical Density Features | integrated_density_od |
| | mean_od |
| Nuclear Size Feature | area |
| Nucleus/Cytoplasm Relation Feature | nc_contrast_orig |
| | edge_contrast_orig |
| Nuclear Texture Features | sd_orig2 |
| | nuc_blur_ave |
| Cytoplasm Optical Density Features | mean_outer_od_r3 |

Figure 5:
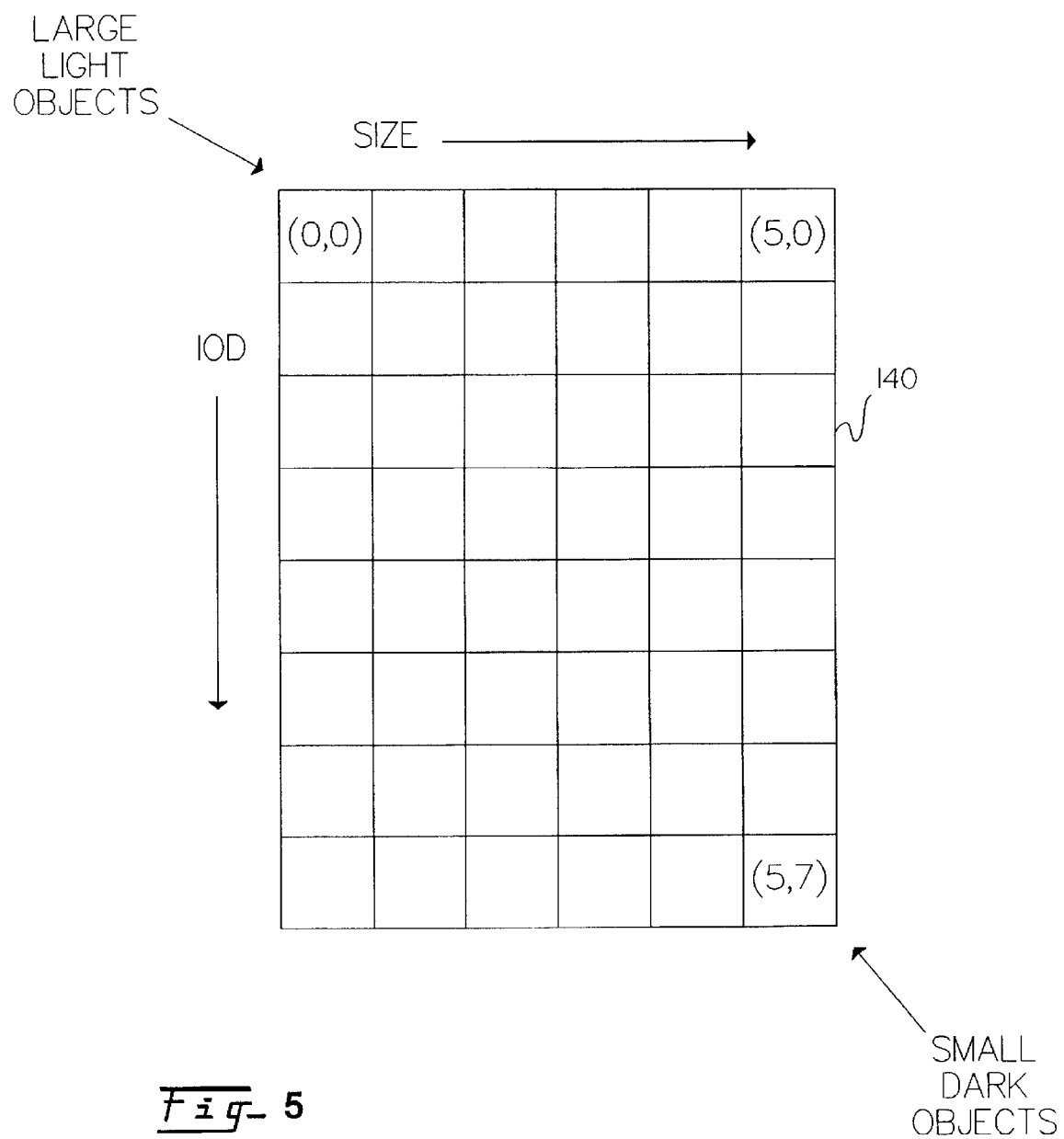
FIG. 5 shows a stain histogram.

Now refer to FIG. 5 which shows an example of a stain histogram 140. The stain histograms 140 are 2-dimensional, with the x-axis representing the size of the cell, and the y-axis representing the integrated optical density of the cell. The IOD bins range from 0 (light) to 7 or 9 (dark). The stain histogram for the first classifier has 10 IOD bins while the second has only 8. The size bins range from 0(large) to 5 (small).

There are six stain bins containing the following size cells:

| Size Bin | Size Range |
| --- | --- |
| 0 | 221+ |
| 1 | 191–220 |
| 2 | 161–190 |
| 3 | 131–160 |
| 4 | 101–130 |
| 5 | 0–100 |

The bin ranges for the integrated optical densities of the cells from the first classifier are shown in the following table:

| Density Bin | Density Range |
| --- | --- |
| 0 | 4,000–6,000 |
| 1 | 6,001–8,000 |
| 2 | 8,001–10,000 |
| 3 | 10,001–12,000 |
| 4 | 12,001–14,000 |
| 5 | 14,001–16,000 |
| 6 | 16,001–18,000 |
| 7 | 18,001–20,000 |
| 8 | 20,001–22,000 |
| 9 | 22,001+ |

The bin ranges for the integrated optical densities of the cells from the second classifier are shown in the following table:

| Density Bin | Density Range |
| --- | --- |
| 0 | 0–4,000 |
| 1 | 4,000–8,000 |
| 2 | 8,001–12,000 |
| 3 | 12,001–16,000 |
| 4 | 16,001–20,000 |
| 5 | 20,001–24,000 |
| 6 | 24,001–28,000 |
| 7 | 28,001+ |

Each object in the image identified as an intermediate cell is placed in the size/density histogram according to its area and integrated optical density. The first histogram includes objects classified as intermediate cells by the first classifier. The second histogram includes objects classified as intermediate cells by either the first or second classifier.

The second part of the stain score generator accumulates several stain measurements for the objects classified as intermediate cells by either of the classifiers. The features are:
mean_od
sd_orig2
nc_contrast_orig
mean_outer_od_r3
nuc_blur_ave
edge_contrast_orig For each of these features, two values are returned to the computer system 540:

(1) The cumulative total of the feature values for all of the intermediate cells. This will be used to compute the mean feature value for all cells identified as intermediate cells over the whole slide.

(2) The cumulative total of the squared feature values for all of the intermediate cells. This will be used with the mean value to compute the standard deviation of the feature value for all cells identified as intermediate cells over the whole slide.

$$\text{s.d.} = \sqrt{(\mu^2) - (u)^2}$$

where $(u)^2$ is the mean value of the feature value squared, and $(\mu^2)$ is the mean of the squared feature values.

Now refer again to FIG. 2, the SIL atypicality index 22 is composed of two measures: (1) an atypicality measure and (2) a probability density process (pdf) measure. The atypicality measure indicates the confidence that the object is truly abnormal. The pdf measure represents how similar this object is to others in the training data set. The combination of these two measures is used to gauge the confidence that an object identified as abnormal by the Stage2 94 Box classifier is truly abnormal. The highest weight is given to detected abnormal objects with high atypicality and pdf measures, the lowest to those with low atypicality and pdf measures.

As illustrated in FIG. 4A, the atypicality index 22 takes all objects left after the Stage2 94 box filter and subjects them to a classifier.

The following is a list of the features used by the atypicality index classifier 22:
nonuniform_gray
nuc_edge_2_mag
compactness2
condensed_compactness
texture_correlation3
nuc_bright_big
mean_background
inertia_2_ratio
nc_score_alt_r3
edge_contrast_orig
mod_N_C_ratio
normalized_mean_od_r3
normalized_mean_od
sd_orig
mod_nuc_OD
sm_edge_9_9
big_blur_ave
big_edge_5_mag
cooc_inertia-4_0
min_mod
big_edge_9_9
sm_blur_sd
big_edge_2_dir
sm_bright
area_outer_edge
area
nuc_blur_ave
nuc_blur_sd
perimeter
nuc_blur_sd_sm The following feature array is composed for the object to be classified:
Feature_Array[0]=nonuniform_gray
Feature_Array[1]=nuc_edge_2_mag
Feature_Array[2]=compactness2
Feature_Array[3]=condensed_compactness
Feature_Array[4]=texture_correlation3
Feature_Array[5]=nuc_bright_big
Feature_Array[6]=mean_background
Feature_Array[7]=inertia_2_ratio
Feature_Array[8]=nc_score_alt_r3
Feature_Array[9]=edge_contrast_orig
Feature_Array[10]=mod_N_C_ratio
Feature_Array[11]=normalized_mean_od_r3
Feature_Array[12]=normalized_mean_od
Feature_Array[13]=sd_orig
Feature_Array[14]=mod_nuc_OD
Feature_Array[15]=sm_edge_9_9
Feature_Array[16]=big_blur_ave
Feature_Array[17]=big_edge_5_mag
Feature_Array[18]=cooc_inertia_4_0
Feature_Array[19]=min_od
Feature_Array[20]=big_edge_9_9
Feature_Array[21]=sm_blur_sd
Feature_Array[22]=big_edge_2_dir
Feature_Array[23]=sm_bright
Feature_Array[24]=area_outer_edge
Feature_Array[25]=cc.area
Feature_Array[26]=nuc_blur_ave
Feature_Array[27]=nuc_blur_sd
Feature_Array[28]=perimeter
Feature_Array[29]=nuc_blur_sd_sm The original feature array is used to derive a new feature vector with 14 elements. Each element corresponds to an eigenvector of a linear transformation as determined by discriminant analysis on the training data set.

The new feature vector is passed to two classifiers which compute an atypicality index 23 and a pdf index 25. The atypicality index 23 indicates the confidence that the object is truly abnormal. The pdf index 25 represents how similar this object is to others in the training data set.

Once the two classification results have been calculated, they are used to increment a 2-dimensional array for the two measures. The results returned by each of the classifiers is an integer number between 1 and 8, with 1 being low confidence and 8 high confidence. The array contains the atypicality index on the vertical axis, and the pdf index on the horizontal axis.

One indication of a classifier's quality is its ability to provide the same classification for an object in spite of small changes in the appearance or feature measurements of the object. For example, if the object was re-segmented, and the segmentation mask changed so that feature values computed using the segmentation mask changed slightly, the classification should not change dramatically.

An investigation into the sources of classification non-repeatability was a part of the development of the invention. As a result, it was concluded that there are two major causes of non-repeatable classification comprising object and presentation effects and decision boundary effects. As the object presentation changes, the segmentation changes, affecting all of the feature measurements, and therefore, the classification.

Segmentation robustness indicates the variability of the segmentation mask created for an object for each of multiple images of the same object. An object with robust segmentation is one where the segmentation mask correctly matches the nucleus and does not vary from image to image in the case where multiple images are made of the same object.

The decision boundary effects refer to objects that have feature values close to the decision boundaries of the classifier, so small changes in these features are more likely to cause changes in the classification result.

Classification decisiveness refers to the variability in the classification result of an object as a result of it's feature values in relation to the decision boundaries of the classifier.

The classification decisiveness measure will be high if the object's features are far from the decision boundary, meaning that the classification result will be repeatable even if the feature values change by small amounts. Two classifiers were created to rank the classification robustness of an object. One measures the classification robustness as affected by the segmentation robustness. The other measures the classification robustness as affected by the classification decisiveness.

The segmentation robustness classifier 24 ranks how prone the object is to variable segmentation and the classification decisiveness classifier 26 ranks the objects in terms of its proximity to a decision boundary in feature space.

Figure 6A:
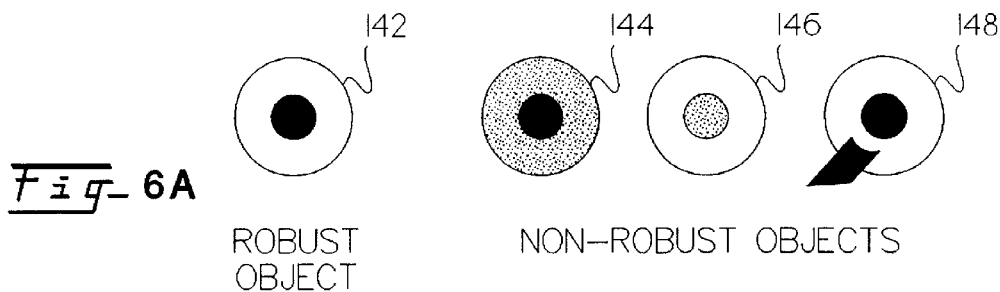
FIG. 6A shows robust and non-robust objects.

FIG. 6A illustrates the effect of object presentation on segmentation. The AutoPap® 300 System uses a strobe to illuminate the FOV. As a result, slight variations in image brightness occur as subsequent images are captured. Objects that have a very high contrast between the nucleus and cytoplasm, such as the robust object 142 shown in FIG. 6A, tend to segment the same even when the image brightness varies. Such objects are considered to have robust segmentation.

Objects that have low contrast, such as the first two non-robust objects 144 and 146, are more likely to segment differently when the image brightness varies; these objects are considered to have non-robust segmentation. Another cause of non-robust segmentation is the close proximity of two objects as is shown in the last non-robust object 148. The segmentation tends to be non-robust because the segmentation process may group the objects.

Robust segmentation and classification accuracy have a direct relationship. Objects with robust segmentation are more likely to have an accurate segmentation mask, and therefore, the classification will be more accurate. Objects with non-robust segmentation are more likely to have inaccurate segmentation masks, and therefore, the classification of the object is unreliable. The segmentation robustness measure is used to identify the objects with possibly unreliable classification results.

Figure 6B:
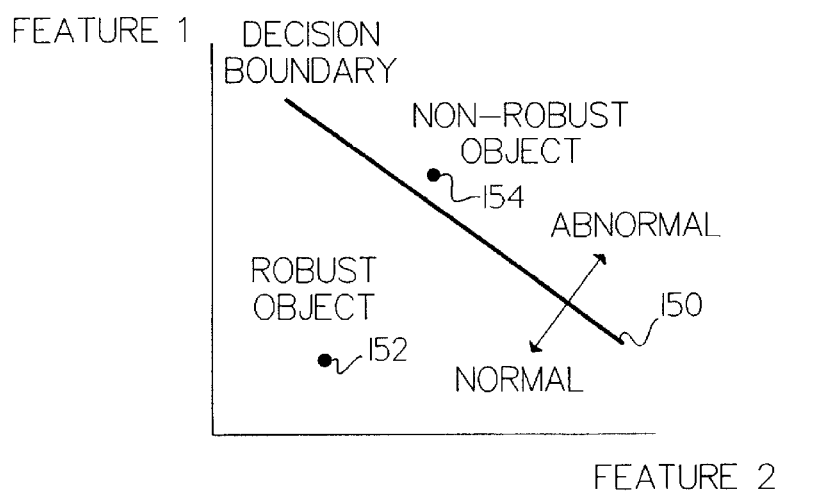
FIG. 6B shows a decision boundary.

FIG. 6B illustrates the decision boundary effect. For objects 154 with features in proximity to decision boundaries 150, a small amount of variation in feature values could push objects to the other side of the decision boundary, and the classification result would change. As a result, these objects tend to have non-robust classification results. On the other hand, objects 152 with features that are far away from the decision boundary 150 are not affected by small changes in feature values and are considered to have more robust classification results.

Figure 6C:
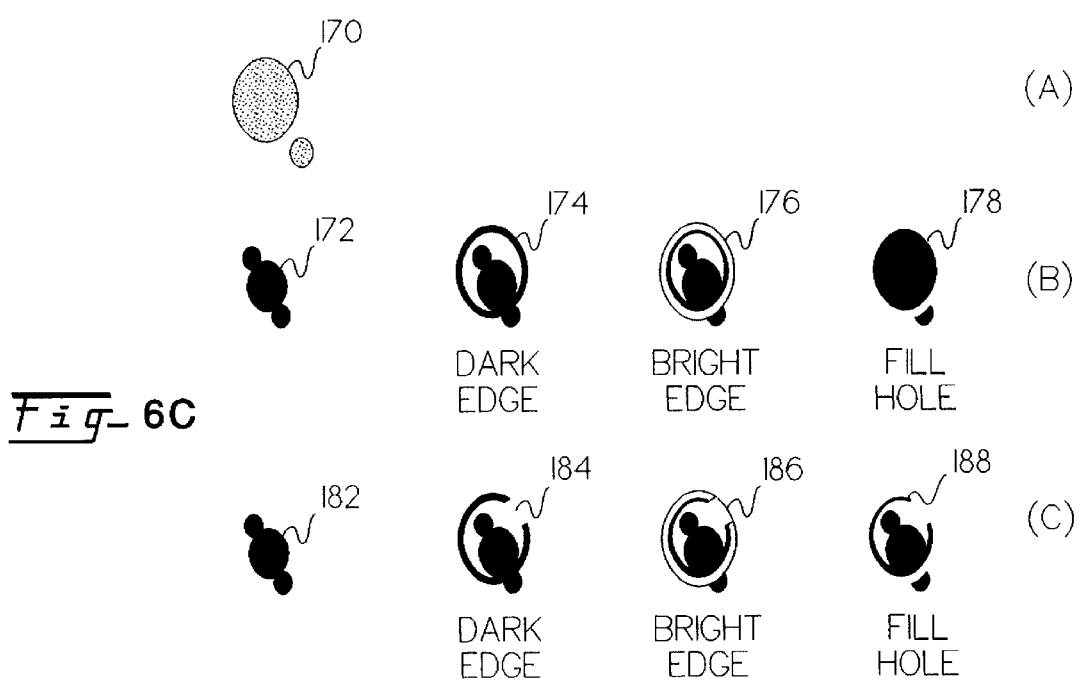
FIG. 6C shows a segmented object.

The segmentation robustness measure is a classifier that ranks how prone an object is to variable segmentation. This section provides an example of variable segmentation and describes the segmentation robustness measure. Variable Segmentation Example:

The invention image segmentation 10 has 11 steps:
1 Pre-processing
2 Histogram statistics
3 Background normalization
4 Enhanced image generation
5 Thresholding image generation
6 Apply thresholding
7 Dark edge incorporation
8 Bright edge exclusion
9 Fill holes
10 Object separation and recovery
11 High threshold inclusion and low value pick up The areas of the segmentation that are most sensitive to small changes in brightness or contrast are steps 7, 8, and 9. FIG. 6C illustrates the operation of these three steps, which in some cases can cause the segmentation to be non-robust. Line (A) shows the object 170 to be segmented, which comprises of two objects close together. Line (B) shows the correct segmentation of the object 172, 174, 176, and 178 through the dark edge incorporation, bright edge exclusion, and fill holes steps of the segmentation process respectively. Line (C) illustrates a different segmentation scenario for the same object 182, 184, 186 and 188 that would result in an incorrect segmentation of the object.

The dark edge incorporation step (7) attempts to enclose the region covered by the nuclear boundary. The bright edge exclusion step (8) attempts to separate nuclear objects and over-segmented artifacts, and the fill hole step (9) completes the object mask. This process is illustrated correctly in line (B) of FIG. 6C. If there is a gap in the dark edge boundary, as illustrated in line (C), the resulting object mask 188 is so different that the object will not be considered as a nucleus. If the object is low contrast or the image brightness changes, the segmentation may shift from the example on line (B) to that on line (C).

The input to the segmentation robustness measure comprises of a set of feature measurements for each object classified as abnormal by the second decision tree classifier of Stage2 94.

The output comprises of a number between 0.0 and 1.0 that indicates the segmentation robustness. Higher values correspond to objects with more robust segmentation.

The features were analyzed to determine those most effective in discriminating between objects with robust and non-robust segmentation. There were only 800 unique objects in the training set. To prevent overtraining the classifier, the number of features that could be used to build a classifier was limited. The features chosen are listed in the following table:

| Feature type | Feature name(s) |
| --- | --- |
| Context Distance Feature | min_distance |
|  | context_3a |
|  | context_1b |
| Context Texture Features | sm_bright |
|  | sm_edge_9_9 |
| Nuclear Density Feature | mean_od |
| Nuclear Texture Features | hole_percent |

This classifier is a binary decision tree that uses a linear feature combination at each node to separate objects with robust segmentation from those with non-robust segmentation. The features described in the following list make up the linear combination:

Feature_Array[0]=mean_od
Feature_Array[1]=sm_bright
Feature_Array[2]=sm_edge_9_9
Feature_Array[3]=context_3a
Feature_Array[4]=hole_percent
Feature_Array[5]=context_1b
Feature_Array[6]=min_distance The features that are sent to each node of the tree are identical, but the importance of each feature at each of the nodes may be different; the importance of each feature was determined during the training process.

The tree that specifies the decision path is called the Segmentation Robustness Measure Classifier. It defines the importance of each feature at each node and the output classification at each terminal node.

The classification result is a number between 0.0 and 1.0 indicating a general confidence in the robustness, where 1.0 corresponds to high confidence.

The classifier was trained using 2373 objects made up of multiple images of approximately 800 unique objects where 1344 objects were robust and 1029 were non-robust.

The performance of the classifier is shown in the following table:

|  | Robust | Non-Robust |
| --- | --- | --- |
| Robust | 1128 | 216 |
| Non-Robust | 336 | 693 |

The vertical axis represents the true robustness of the object, and the horizontal axis represents the classification result. For example, the top row of the table shows the following:

1128 objects with robust segmentation were classified correctly as robust.

216 objects with robust segmentation were classified incorrectly as non-robust.

The classifier correctly identified 77% of the objects as either having robust or non-robust segmentation.

The confidence measure is derived from the classification results of the decision tree. Therefore, using the confidence measures should provide approximately the same classification performance as shown in the preceding table.

The classification decisiveness measure indicates how close the value of the linear combination of features for an object is to the decision boundary of the classifier. The decisiveness measure is calculated from the binary decision trees used in the final classifiers of Stage2 94 and stage3 96 by adding information to the tree to make it a probabilistic tree.

The probabilistic tree assigns probabilities to the left and right classes at each decision node of the binary decision tree based on the proximity of the feature linear combination value to the decision boundary. When the linear combination value is close to the decision boundary, both left and right classes will be assigned a similar low decisiveness value. When the linear combination value is away from the decision boundary, the side of the tree corresponding to the classification decision will have high decisiveness value. The combined probabilities from all the decision nodes are used to predict the repeatability of classification for the object.

A probabilistic Fisher's decision tree (PFDT) is the same as a binary decision tree, with the addition of a probability distribution in each non-terminal node. An object classified by a binary decision tree would follow only one path from the root node to a terminal node. The object classified by the PFDT will have a classification result based on the single path, but the probability of the object ending in each terminal node of the tree is also computed, and the decisiveness is based on those probabilities.

Figure 7A:
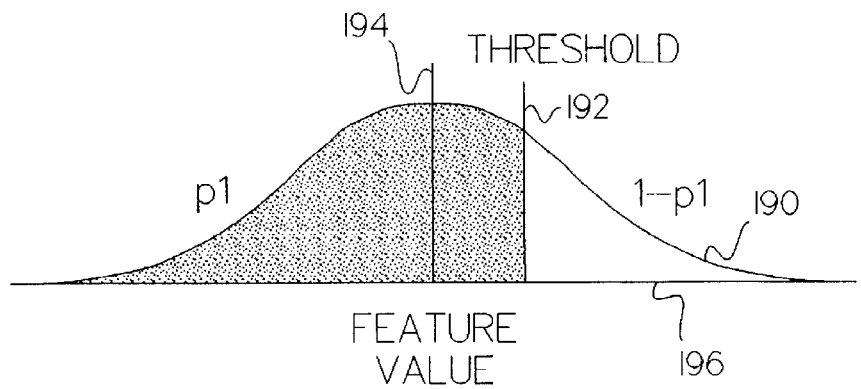
FIG. 7A shows a threshold graph.
Figure 7B:
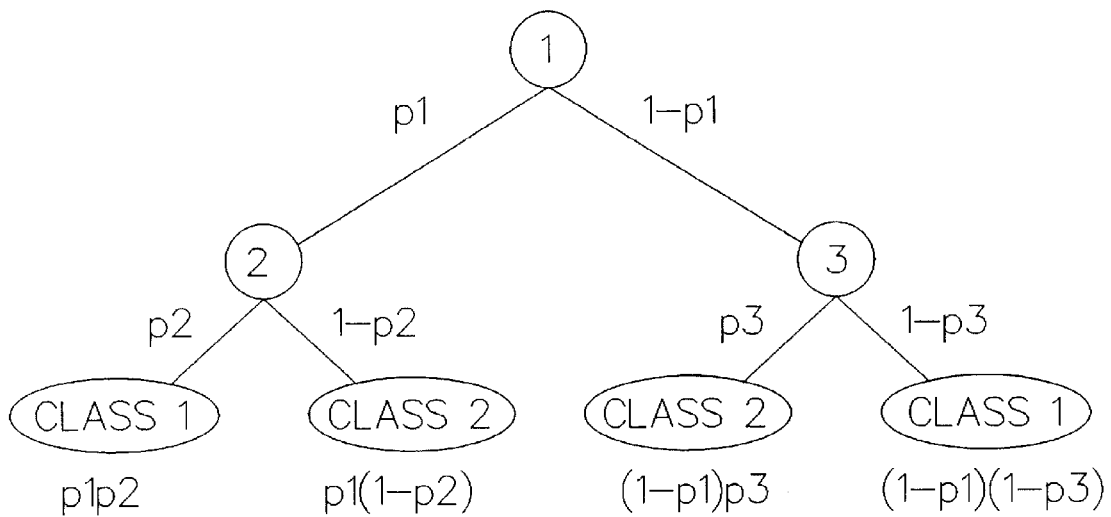
FIG. 7B shows a binary decision tree.

FIGS. 7A and 7B show how the decisiveness measure is computed. The object is classified by the regular binary decision trees used in Stage2 94 and stage3 96. The trees have been modified as follows. At each decision node, a probability is computed based on the distance between the object and the decision boundary.

At the first decision node, these probabilities are shown as $p_1$ and $1-p_1$. The feature values of the objects which would be entering the classification node are assumed to have a normal distribution 190. This normal distribution is centered over the feature value 194, and the value of $p_1$ is the area of the normal distribution to the left of the threshold 192. If the features were close to the decision boundary, the values of $p_1$ and $1-p_1$ indicated by area 196 would be approximately equal. As the feature combination value drifts to the left of the decision boundary, the value of $p_1$ increases. Similar probability values are computed for each decision node of the classification tree as shown in FIG. 7B. The probability associated with each classification path, the path from the root node to the terminal node where the classification result is assigned, is the product of the probabilities at each branch of the tree. The probabilities associated with each terminal node is shown in FIG. 7B. For example, the probability of the object being classified class1 in the left most branch is $p_1 p_2$. The probability that the object belongs to one class is the sum of the probabilities computed for each terminal node of that class. The decisiveness measure is the difference between the probability that the object belongs to class1 and the probability that it belongs to class2.

$$P_{class1} = p_1 p_2 + (1-p_1)(1-p_3)$$
$$P_{class2} = p_1(1-p_2) + (1-p_2)p_3$$
$$\text{Decisiveness} = |P_{class1} - P_{class2}|$$

The invention computes two classification decisiveness measures. The first is for objects classified by the second decision tree classifier of Stage2 94. The second is for objects classified by the decision tree classifier of stage3 96. The classification decisiveness measure is derived as the object is being classified. The output comprises the following:

The classification decisiveness measure for the object at Stage2 94 and stage3 96 if the object progressed to the stage3 96 classifier. The decisive measures range from 0.0 to 1.0.

The product of the classification confidence and the classification decisiveness measure for the object at Stage2 94 and stage3 96.

The features used for the classification decisiveness measure are the same as those used for the second decision tree of Stage2 94 and decision tree of stage3 96 because the classification decisiveness measure is produced by the decision trees.

The decision rules for the classification decisiveness measure are the same as those used for the second decision tree of Stage2 94 and decision tree of stage3 96 because the classification decisiveness measure is produced by the decision trees.

Refer again to FIG. 2, miscellaneous process measurements 26 describes features which are computed during classification stages of the invention. They are described here because they can be grouped together and more easily explained than they would be in the individual classification stage descriptions. The following features are described in this part of the disclosure:

Stage2 Confidence Histogram
Stage3 Confidence Histogram
Stage4 Confidence Histogram
Ploidy Confidence Histogram
Stage2 94 IOD histogram
Stage3 IOD histogram
Contextual Stage1 Alarms
Contextual Stage2 94 Alarms
Addon Feature Information
Estimated Cell Count Confidence Histograms When objects on a slide are classified as alarms, knowing with what confidence the classifications occurred may help to determine whether the slide really is abnormal or not. Therefore, the following alarm confidence histograms are computed:

Stage2 94
Stage3 96
Stage4 98

Stage2 94

The classifier for Stage2 94, classifier 2 is a binary decision tree. The measure of confidence for each terminal node is the purity of the class at that node based on the training data used to construct the tree. For example, if a terminal node was determined to have 100 abnormal objects and 50 normal objects, any object ending in that terminal node would be classified as an abnormal object, and the confidence would be (100+1)/(150+2) or 0.664.

The 10 bin histogram for Stage2 94 confidences is filled according to the following confidence ranges.

| Confidence Bin | Confidence Range |
|---|---|
| 0 | 0.000–0.490 |
| 1 | 0.500–0.690 |
| 2 | 0.700–0.790 |
| 3 | 0.800–0.849 |
| 4 | 0.850–0.874 |
| 5 | 0.875–0.899 |
| 6 | 0.900–0.924 |
| 7 | 0.925–0.949 |
| 8 | 0.950–0.974 |
| 9 | 0.975–1.000 |

Stage3

The confidence of the stage3 96 classifier is determined in the same manner as the Stage2 94 classifier. The confidence histogram bin ranges are also the same as for the Stage2 94 classifier.

Stage4

Figure 8:
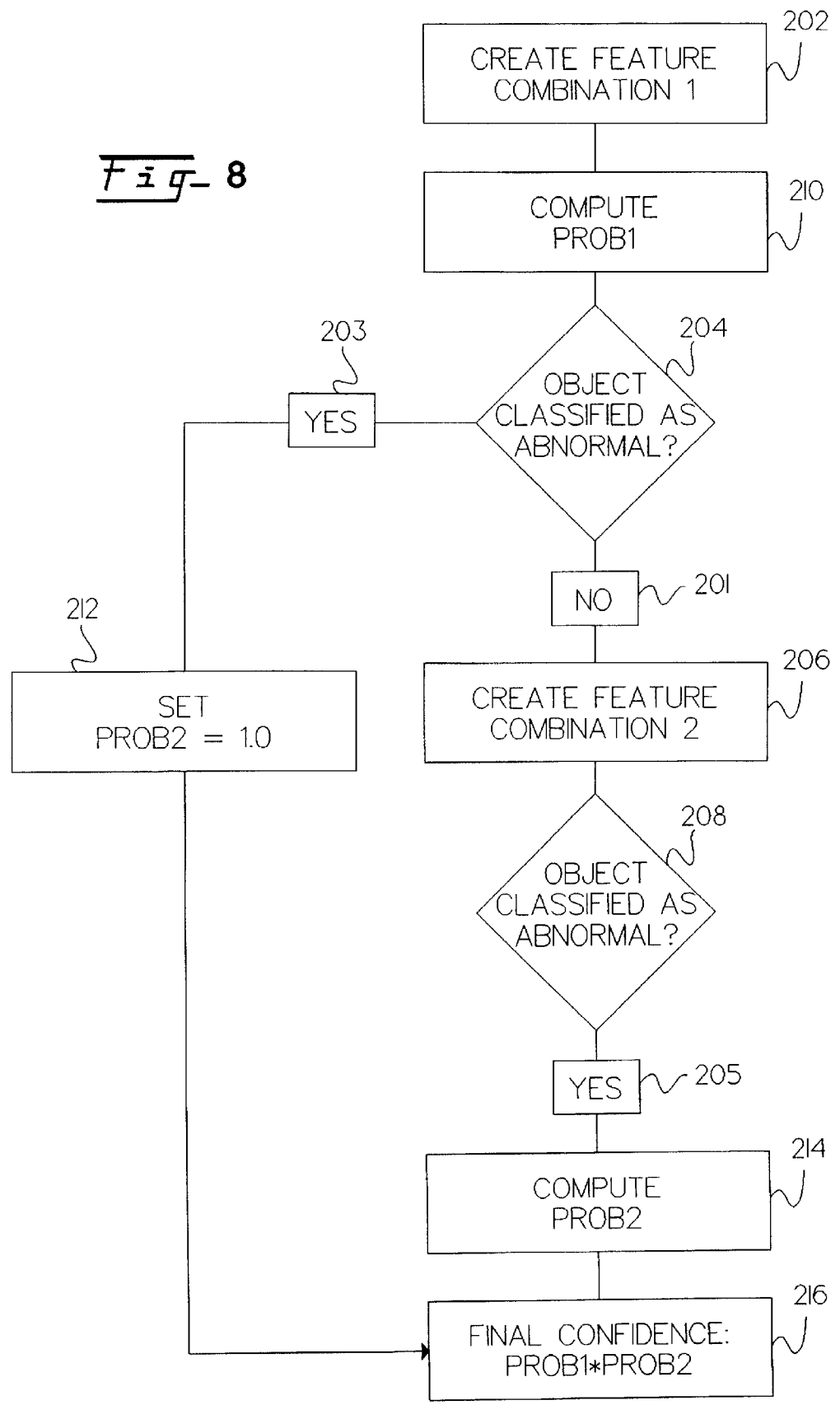
FIG. 8 shows a stage 4 classifier.

FIG. 8 illustrates how the confidence is computed for the stage4 98 classifier. The classification process is described in the object classification 14 Stage4 98 section. If the object is classified as abnormal at steps 203 and 204 by the first classifier that uses the feature combination 1 step 202, the probability is computed in step 210 as described below. The object will not go to the second classifier, so the probability for the second classifier is set to 1.0 in step 212, and the final confidence is computed in step 216 as the product of the first and second probabilities. If the object was classified as normal at step 201 and step 204 by the first classifier, the probability is computed, and the object goes to the second classifier that uses the feature combination 2 step 206. If the object is classified as abnormal by the second classifier at step 205 and step 208, the probability is computed in step 214 for that classifier, and the final confidence is computed as the product of the first and second probabilities in step 216. If the object is classified as normal by the second classifier, no confidence is reported for the object.

To determine the confidence of the classification results in stage4 98, the mean and standard deviations of the linear combinations of the normal/artifact and abnormal populations were calculated from the training data. These calculations were done for the feature combination 1 step 202 and feature combination 2 step 206. The results are shown in the following table:

|  | Feature Combination 1 | Feature Combination 2 |
|---|---|---|
| Normal/Artifact mean | 2.55 | −0.258 |
| Normal/Artifact sd | 0.348 | 0.084 |
| Abnormal mean | 2.80 | −0.207 |
| Abnormal sd | 0.403 | 0.095 |

Using the means and standard deviations calculated, the normal and abnormal likelihoods are computed for feature combination 1:

$$\text{normal\_likelihood} = \frac{(\text{object\_value} - \text{norm\_pop\_mean})^2}{\text{Norm\_pop\_sd}}$$

$$\text{abnormal\_likelihood} = \frac{(\text{object\_value} - \text{abnorm\_pop\_mean})^2}{\text{abnorm\_pop\_sd}}$$

Compute the likelihood ratio as:

$$\text{likelihood\_ratio} = \frac{\text{norm\_pop\_}}{\text{abnorm\_pop\_sd}} (\exp[0.5(\text{abnorm\_likelihood} - \text{norm\_likelihood})])$$

Normalize the ratio:

$$prob1 = \frac{\text{likelihood\_ratio}}{1 + \text{likelihood\_ratio}}$$

If the object is classified as normal by the first classifier and as abnormal by the second classifier, compute the normalized likelihood ratio as described previously using the means and standard deviations from the second feature combination. This value will be prob2. The confidence value of an object classified as abnormal by the stage4 98 classifier is the product of prob1 and prob2, and should range from 0.0 to 1.0 in value. The confidence value is recorded in a histogram.

The confidence histogram has 12 bins. Bin[0] and Bin[11] are reserved for special cases. If the values computed for combination 1 or combination 2 fall near the boundaries of the values existing in the training set, then a confident classification decision cannot be made about the object. If the feature combination value of the object is at the high end of the boundary, increment bin[11] by 1. If the feature combination value is at the low end, increment bin[0] by 1. The decision rules for these cases are stated as follows:

if (combination1>4.3 || combination2>0.08)

stage4 98_prob_hist[11] is incremented.

if (combination1<1.6 || combination2<−0.55)

stage4 98_prob_hist[0] is incremented.

If the feature combination values are within the acceptable ranges, the objects confidence is recorded in a histogram with the following bin ranges:

| Confidence Bin | Confidence Range |
|---|---|
| 1 | 0.000−<0.500 |
| 2 | 0.500−<0.600 |
| 3 | 0.600−<0.700 |
| 4 | 0.700−<0.750 |
| 5 | 0.750−<0.800 |
| 6 | 0.800−<0.850 |
| 7 | 0.850−<0.900 |
| 8 | 0.900−<0.950 |
| 9 | 0.950−<0.975 |
| 10 | 0.975−1.000 |

Figure 9:
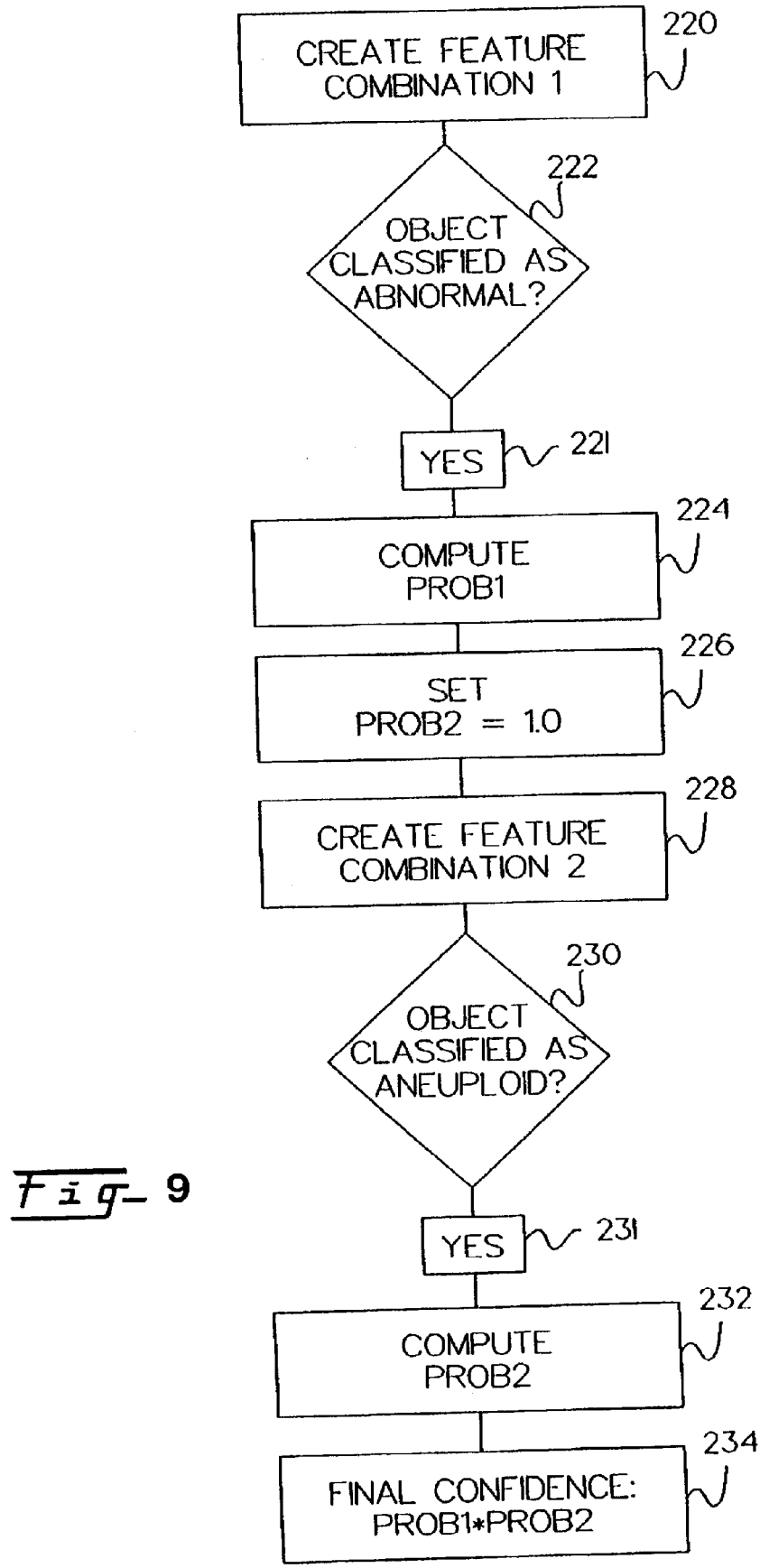
FIG. 9 shows a ploidy classifier.

FIG. 9 illustrates how the confidence is computed for the ploidy classifier 100. The classification process is described in the object classification 14 Ploidy 100 section of this document. The object is classified at step 222. If the object is classified as abnormal, "YES" 221, by the first classifier that uses the feature combination 1 step 220, the probability is computed in step 224 described below and prob2 is set to 1.0 at step 226. The object is then sent to the second classifier. At step 230, if the object was classified as abnormal, "YES" 251, by the second classifier that uses the feature combination 2 step 228, the probability is computed for that classifier at step 232, and the final confidence is computed as the product of the first and second probabilities in step 234. If the object is classified as normal by either the first or the second classifier, no confidence is reported for the object.

To determine the confidence of the classification results in the ploidy classifier 100, the mean and standard deviations of the linear combinations of the normal and abnormal populations were calculated from the training data. These calculations were done for the feature combination 1 step 220 and the feature combination 2 step 228. The results are shown in the following table:

|  | The feature combination 1 step 220 | The feature combination 2 step 228 |
|---|---|---|
| Normal/Artifact mean | 2.55 | −0.258 |
| Normal/Artifact sd | 0.348 | 0.084 |
| Abnormal mean | 2.80 | −0.207 |
| Abnormal sd | 0.403 | 0.095 |

Using the means and standard deviations calculated, the normal and abnormal likelihoods are computed for the feature combination 1 step 220:

$$\text{normal\_likelihood} = \frac{(\text{object\_value} - \text{norm\_pop\_mean})^2}{\text{Norm\_pop\_sd}}$$

-continued $$\text{abnormal\_likelihood} = \frac{(\text{object\_value} - \text{abnorm\_pop\_mean})^2}{\text{abnorm\_pop\_sd}}$$

Compute the likelihood ratio as:

$$\text{likelihood\_ratio} = \frac{\text{norm\_pop}}{\text{abnorm\_pop\_sd}} (\exp[0.5(\text{abnorm\_likelihood} - \text{norm\_likelihood})])$$

Normalize the ratio:

$$prob1 = \frac{\text{likelihood\_ratio}}{1 + \text{likelihood\_ratio}}$$

If it goes to Step2, compute the normalized likelihood ratio as described above using the means and standard deviations from the second feature combination. This value will be prob2. The confidence value of an object classified as abnormal by the ploidy classifier 100 is the product of prob1 and prob2, and should range from 0.0 to 1.0 in value. The confidence value is recorded in a histogram.

The confidence histogram has 12 bins. Bin[0] and Bin[11] are reserved for special cases. If the values computed for combination 1 or combination 2 fall near the boundaries of the values existing in the training set, then a confident classification decision cannot be made about the object. If the feature combination value of the object is at the high end of the boundary, increment bin[11] by 1. If the feature combination value is at the low end, increment bin[0] by 1. The decision rules for these cases are stated as follows:.

if (combination1<−0.60 || combination2<−0.30)

sil_ploidy_prob_hist[0] is incremented.

if (combination1>0.35 || combination2>1.60)

sil_ploidy_prob_hist[11] is incremented.

If the feature combination values are within the acceptable ranges, the objects confidence is recorded in a histogram with the following bin ranges:

| Confidence Bin | Confidence Range |
|---|---|
| 1 | 0.000–<0.500 |
| 2 | 0.500–<0.600 |
| 3 | 0.600–<0.700 |
| 4 | 0.700–<0.750 |
| 5 | 0.750–<0.800 |
| 6 | 0.800–<0.850 |
| 7 | 0.850–<0.900 |
| 8 | 0.900–<0.950 |
| 9 | 0.950–<0.975 |
| 10 | 0.975–1.000 |

IOD Histograms

When objects are classified as alarms, it is useful to know their density. Abnormal cells often have an excess of nuclear materials, causing them to stain more darkly. Comparing the staining of the alarms to the staining of the intermediate cells may help determine the accuracy of the alarms.

Stage2 94

Each object classified as an abnormal cell by the Stage2 94 classifier is counted in the alarm IOD histogram. The ranges of the bins are shown in the following table:

| IOD Bin | Range of Integrated Optical Densities per Bin |
|---|---|
| 0 | 0–11,999 |
| 1 | 12,000–13,000 |
| 2 | 14,000–15,999 |
| 3 | 16,000–17,999 |
| 4 | 18,000–19,999 |
| 5 | 20,000–21,999 |
| 6 | 22,000–23,999 |
| 7 | 24,000–25,999 |
| 8 | 26,000–27,999 |
| 9 | 28,000–29,999 |
| 10 | 30,000–31,999 |
| 11 | 32,000–33,999 |
| 12 | 34,000–35,999 |
| 13 | 36,000–37,999 |
| 14 | 38,000–39,999 |
| 15 | 40,000+ |

Stage3

The stage3 96 alarm IOD histogram is the same format as the Stage2 94 histogram. It represents the IOD of each object classified as an abnormal object by the stage3 96 classifier.

Contextual Alarm Measurements

Abnormal objects tend to form clusters, so it is useful to measure how many alarmed objects are close to other alarmed objects. Specifically, the following contextual measurements are made:

Contextual Stage2 94 alarm: the number of Stage1 94 alarms that are close to a Stage2 94 alarm Contextual Stage3 96 alarm: the number of Stage2 94 alarms that are close to a stage3 96 alarm The distance between alarm objects is the Euclidean distance:

$$\sqrt{\Delta x^2 + \Delta y^2}$$

If a stage3 96 alarm is contained in an image, the distance between it and any Stage2 94 alarms is measured. If any are within a distance of 200, they are considered close and are counted in the cluster2 feature. This features value is the number of Stage2 94 alarms found close to stage3 96 alarms. The same applies to Stage1 alarms found close to Stage2 94 alarms for the cluster1 feature.

Each object that is close to a higher alarm object is counted only once. For example, if a Stage2 94 alarm is close to two stage3 96 alarms, the value of cluster1 will be only 1.

Estimated Cell Count

The results of the Stage1 classification are used to estimate the number of squamous cells on the slide.

If we define the following variables, norm=sil_stage1_normal_count1 abn=sil_stage1_abnormal_count1 art=sil_stage1_artifact_count1 the estimated cell count is then computed according to this formula:

$$\text{Est\_CC} = 0.91 + 1.44(norm) + 0.75(abn) + 0.26(art) -$$
$$0.0021(norm^2) + 0.083(abn^2) - 0.0013(art^2) - 0.015(norm^2) -$$
$$0.043(norm * abn) - 0.016(art * abn) + 0.0016(norm * art * abn)$$

Process performance has been tracked and validated throughout all stages of classification training. A cross validation method was adapted for performance tracking at each stage, in which training data is randomly divided into five equal sets. A classifier is then trained by four of the five sets and tested on the remaining set. Sets are rotated and the process is repeated until every combination of four sets has been used for testing:

| Training data | Test set |
|---|---|
| sets 1, 2, 3 & 4 | 5 |
| sets 2, 3, 4 & 5 | 1 |
| sets 3, 4, 5 & 1 | 2 |
| sets 4, 5, 1 & 2 | 3 |
| sets 5, 1, 2, & 3 | 4 |

The classification merit (CM) gain is used to measure the performance of the apparatus of the inventions at each stage.

$$CM = \frac{Sensitivity}{FPR}$$

where Sensitivity is the percentage of abnormal cells correctly classified as abnormal, FPR is the false positive rate, or the percentage of normal cells and artifacts incorrectly classified as abnormal cells.

The objects that were classified as abnormal in the previous stage continue to a further stage of classification. This stage will refine the classification produced by the previous stage, eliminating objects that were incorrectly classified as abnormal. This increases the CM gain. The goal for the apparatus of the invention is-CM gain=200.

CM Calculation Example

A typical normal slide might contain 1,000 significant objects that are normal cells. The goal for the artifact retention rate is 0.2%

A low prevalence abnormal slide might contain the same number of normal cells, along with ten significant single abnormal cells. Of the abnormal slide's ten significant abnormal objects, it is expected that the 4× process can select five objects for processing by the invention. Object classification 14 that has a 40% abnormal cell sensitivity reduces this number to 2. (5×40%=2).

$$CM = \frac{40\%}{0.20} = 200$$

For process performance, the CM gain is expected to fall within the range of 200±10, and sensitivity is expected to be within the bounds of 40±10. Results of cross validated testing for each stage are illustrated in Table 5.1, which shows overall CM gain of 192.63 and overall sensitivity of 32.4%, each of which fall within the range of our goal.

The invention Feature Descriptions

This section contains names and descriptions of all features that can be used for object classification 14. Not all features are used by the object classification 14 process. Those features that are used by the invention are listed in feature sets.

The feature names are taken from the TwentyXFeatures_s structure in the AutoPap® 300 software implementation.

Items shown in bold face are general descriptions that explain a set of features. Many features are variations of similar measures, so an explanation block may precede a section of similar features.

| Type | Feature | Description |
|---|---|---|
| int | label_cc: | A unique numeric label assigned to each segmented object. The object in the upper-left corner is assigned a value of 1. The remaining object are labeled 2, 3, etc. from left to right and top to bottom. |
| int | x0: | Upper left x coord. of the corner of the box which contains the object region of interest. |
| int | y0: | Upper left y coord. of the corner of the box which contains the object region of interest. |
|  | x1: | Lower right x coord. of the corner of the box which contains the object region of interest. |
| int | y1: | Lower right y coord. of the corner of the box which contains the object region of interest. |
| float | area: | Number of pixels contained in the labeled region. |
| float | sch: | A measure of shape defined as: x = x1 − x0 + 1y = y1 − y0 + 1sch = 100 * abs(x − y)/(x + y) |
| float | sbx: | A measure of shape defined as: x = x1 − x0 + 1 = y1 − y0 + 1 sbx = 10 * x * y/area |
| int | stage1_label: | The classification label assigned to the object by the stage1 classifier. |
| int | stage2 94_label: | The classification label assigned to the object by the stage2 94 classifier. |
| int | stage3 96_label: | The classification label assigned to the object by the stage3 96 classifier. |
| float | area2: | Same feature as area except the area of interest (labeled region) is first eroded by a 3 × 3 element (1-pixel). |
| float | area_inner_edge: | Number of pixels in the erosion residue using a 5 × 5 element on the labeled image (2-pixel inner band). |
| float | area_outer_edge: | Number of pixels in the 5 × 5 dilation residue minus a 5 × 5 closing of the labeled image (approx. 2-pixel outer band). |
| float | auto_mean_diff_orig2: | autothresh_orig2-mean_orig2. |
| float | auto_mean_diff_enh2: | autothresh_enh2-mean_enh2. |
| float | autothresh_enh: | These features are computed in the |

| Type | Feature | Description |
|---|---|---|
| | | same way as autothresh_orig except the enhanced image is used instead of the original image. |
| float | autothresh_enh2: | These features are computed in the same way as autothresh_orig2 except the enhanced image is used instead of the original image. |
| float | autothresh_orig: | This computation is based on the assumption that original image gray scale values within the nuclear mask are bimodally distributed. This feature is the threshold that maximizes the value of "variance-b" given in equation 18 in the paper by N. Otsu titled "A threshold selection method from gray-level histograms", IEEE trans. on systems, man. and cybernetics, vol. smc-9, no. 1 January, 1979. |
| float | autothresh_orig2: | The same measurement except gray scale values are considered within a nuclear mask that has first been eroded by a 3 × 3 element (1-pixel)). |
| float | below_autothresh_enh2: | (count of pixels < autothresh_enh2)/area2 |
| float | below_autothresh_orig2: | (count of pixels < autothresh_orig2)/area2 |
| float | compactness: | perimeter * perimeter/area |
| float | compactness2: | perimeter2 * perimeter2/area |
| float | compactness_alt: | perimeter2/nuclear_max |

| Type | Feature | Description |
|---|---|---|

Condensed
For the condensed features, condensed pixels are those whose optical density value is:
>ftCondensedThreshold *mean_od.
ftCondensedThreshold is a global floating point variable that can be modified (default is 1.2).

float    condensed_percent: Sum of the condensed pixels divided by the total object area.
float    condensed_area_percent: The number of condensed pixels divided by the total object area.
float    condensed_ratio: Average optical density values of the condensed pixels divided by the *mean_od*.
float    condensed_count: The number of components generated from a 4-point connected components routine on the condensed pixels.
float    condensed_avg_area: The average area (pixel count) of all the of condensed components.
float    condensed_compactness: The total number of condensed component boundary pixels squared, divided by the total area of all the condensed components.
float    condensed_distance: The sum of the squared euclidean distance of each condensed pixel to the center of mass, divided by the area.
float    cytoplasm max: The greatest distance transform value of the cytoplasm image within each area of interest. This value is found by doing an 8-connect distance transform of the cytoplasm image, and then finding the largest value within the nuclear mask.
float    cytoplasm_max_alt: The greatest distance transform value of the cytoplasm image within each area of interest. The area of interest for *cytoplasm_max* is the labeled image while the area of interest of *cytoplasm_max_alt* is the labeled regions generated from doing a skiz of the labeled image.
float    density_0_1: perimeter_out - perimeter
float    density_1_2: Difference between the '1' bin and '2' bin of the histogram described in perimeter.
float    density_2_3: Difference between the '2' bin and '3' bin of the histogram described in perimeter
float    density_3_4: Difference between the '3' bin and '4' bin of the histogram described in perimeter.
float    edge_contrast_orig: First a gray scale dilation is calculated on the original image using a 5 × 5 structure element. The gray-scale residue is then computed by subtracting the original image from the dilation .edge_contrast_orig is the mean of the residue in a 2-pixel outer ring minus the mean of the residue in a 2-pixel inner ring (the ring refers to the area of interest -- see *area_outer_edge*)

float    integrated_density_enh: Summation of all gray-scale valued pixels within an area of interest (values taken from enhanced image). Value is summed from the conditional histogram of image.
float    integrated_density_enh2: The same measurement as the last one except the area of interest is first eroded by a 3 × 3 element (1-pixel)).
float    integrated_density_od: Summation of all gray-scaled valued pixels within an area of interest (values taken from the od image). The od (optical density) image is generated in this routine using the feature processor to do a look-up table operation. The table of values used can be found in the file *fov_features.c* initialized in the static int array *OdLut*.
float    integrated_density_od2: The same measurement as the last one except the area of interest is first eroded by a 3 × 3 element (1-pixel).
float    integrated_density_orig: Summation of all gray-scale valued pixels within an area of interest (values taken from original image). Value is summed from the conditional histogram of image.
float    integrated_density_orig2: The same measurement as the last one except the area of interest is first eroded by a 3 × 3 element (1-pixel).
float    mean_background: Calculates the average gray-scale value for pixels not on the cytoplasm mask.
float    mean_enh: Mean of the gray-scale valued pixels within an area of interest. Calculated simultaneously with *integrated_density_enh* from the enhanced image.
float    mean_enh2: The same measurement as the last one except the area of interest is first eroded by a 3 × 3 element (1-pixel).
float    mean_od: The mean of gray-scale values in the od image within the nuclear mask.
float    mean_od2: The same measurement as the last one except the area of interest is first eroded by a 3 × 3 element (1-pixel).
float    mean_orig: Mean of gray-scale valued pixels within an area of interest. Calculated simultaneously with *integrated_density_orig* from the original image.
float    mean_orig2: The same measurement as *mean_orig* except the area of interest is first eroded by a 3 × 3 element (1-pixel).
float    mean_outer_od: The mean of the optical density image is found in an area produced by finding a 5 × 5 dilation

| Type | Feature | Description |
|---|---|---|
| | | residue minus a 5 × 5 closing of the nuclear mask (2-pixel border). |
| float | normalized_integrated_od: | First subtract *mean_outer_od* from each gray-scale value in the od image. This produces the "reduced values". Next find the sum of these reduced values in the area of the nuclear mask. |
| float | normalized_integrated_od2: | The same summation described with the last feature computed in the area of the nuclear mask eroded by a 3 × 3 element (1-pixel). |
| float | normalized_mean_od: | computed With the reduced values formed during the calculation of *normalized_integrated_od* : find the mean of the reduced values in the nuclear mask. |
| float | normalized_mean_od2: | Same calculation as *normalized_mean_od*, except the nuclear mask is first eroded by a 3 × 3 structure element (1-pixel). |
| float | nc_contrast_orig: | Mean of gray-values in outer ring minus *mean_orig2*. |
| float | nc_score: | Nuclear-cytoplasm ratio.*nc_score* = *nuclear_max / cytoplasm_max*. |
| float | nc_score_alt: | Nuclear-cytoplasm ratio.*nc_score_alt* = *nuclear_max / cytoplasm_max_alt* |
| float | nuclear_max: | The greatest 4-connect distance transform value within each labeled region. This is calculated simultaneously with perimeter and compactness using the distance transform image. |
| float | perimeter: | A very close approximation to the perimeter of a labeled region. It is calculated by doing a 4-connect distance transform, and then a conditional histogram. The '1' bin of each histogram is used as the perimeter value. |
| float | perimeter_out: | The "outside" perimeter of a labeled region. It is calculated by doing a dilation residue of the labeled frame using a 3 × 3 (1-pixel) element followed by a histogram. |
| float | perimeter2: | The average of perimeter and *perimeter_out*. |
| float | region_dy_range_enh: | The bounding box or the region of interest is divided into a 3 × 3 grid (9 elements). If either side of the bounding box is not evenly divisible by 3, then either the dimension of the center grid or the 2 outer grids are increased by one so that there are an integral number of pixels in each grid space. A mean is computed for the enhanced image in the area in common between the nuclear mask and each grid space. The region's dynamic range is the maximum of the means for each region minus the minimum of the means for each region. |
| float | sd_difference: | Difference of the two standard deviations.*sd_difference = sd_orig − sd_enh*. |
| float | sd_enh: | Standard deviation of pixels in an area of interest. Calculated simultaneously with *integrated_density_enh* from the enhanced image. |
| float | sd_enh2: | The same measurement *sd_enh* except the area of interest is first eroded by a 3 × 3 element (1-pixel)). |
| float | sd_orig: | Standard deviation of pixels in an area of interest. Calculated simultaneously with *integrated_density_orig* from the original image. |
| float | sd_orig2: | The same measurement as *sd_orig* one except the area of interest is first eroded by a 3 × 3 element (1-pixel)). |
| float | shape_score: | Using the 3 × 3 gridded regions described in the calculation of *region_dy_range_enh*, the mean grayscale value of pixels in the object mask in each grid is found. Four quantities are computed from those mean values: H, V, Lr, and Rl.<br>For H: Three values are computed as the sum of the means for each row. H is then the maximum row value − minimum row value.<br>For V: Same as for H, computed on the vertical columns of the grid.<br>For Lr: One value is the sum of the means for the diagonal running from the top left to the bottom right. The other two values are computed as the sum of the three means on either side of this diagonal. The value of Lr is the maximum − minimum value for the three regions.<br>For Rl: *Same as Lr, except that the diagonal runs from bottom-left to top-right. |

$$Shape\_Score = \sqrt{V^2 + h^2 + Lr^2 + Rl^2}$$

| Type | Feature | Description |
|---|---|---|
| float | perim_out_r3: | The "outside" perimeter of a labeled region determined by doing a 4-connect distance transform of the labeled image. The number of '1's in each mask are counted to become this value. |
| float | nc_score_r3: | The average value of the 8-connect distance transform of the cytoplasm mask is found inside the 3 × 3 dilation residue of the nuclear mask. Call this value X. The feature is then: *nuclear_max/(X + nuclear_max)*. |
| float | nc_score_alt_r3: | Using "X" as defined in *nc_score_r3*, the feature is: area/(3.14*X*X) |
| float | nc_score_r4: | The median value of the 8-connect distance transform of the cytoplasm mask is found inside the 3 × 3 dilation residue of the nuclear mask. This value is always an integer since the discrete probability density process always crosses 0.5 at the integer values. Call this value Y. The feature is then: *nuclear_max/(Y + nuclear_max)*. |
| float | nc_score_alt_r4: | Using "Y" as defined in *nc_score_r4* , the feature is: area/(3.14*Y*Y) |
| float | mean_outer_od_r3: | The mean value of the optical density image in a 9 × 9 (4 pixel) dilation residue minus a 9 × 9 closing of the nuclear mask. The top and bottom 20% of the histogram are not used in the calculation. |
| float | normalized_mean_od_r3: | As in *normalized_mean_od* except that the values are reduced by *mean_outer_od_r3*. |
| float | normalized_integrated od r3: | As in *normalized_integrated_od* except that the values are reduced by *mean_outer_od_r3*. |
| float | edge_density_r3: | A gray-scale dilation residue is performed on the original image using a 3 × 3 element. The feature is the number of pixels > 10 that lie in the 5 × 5 erosion of the nuclear mask. |

Texture

In the following texture features, two global variables can be modified to adjust their calculation. ftOccurranceDelta is an integer specifying the distance between the middle threshold (mean) and the low threshold, and the middle (mean) and the high threshold. ftOccurranceOffset is an integer specifying the number of pixels to "look ahead" or "look down".

To do texture analysis on adjacent pixels, this number must be 1. To compute the texture features the "S" or "cooccurrence matrix" is first defined. To compute this matrix, the original image is first thresholded into 4 sets. Currently the thresholds to determine these four sets are as follows, where M is the mean_orig: x=1 if x<M−20, x=2 if M−20<=x<M, x=3 if M<=x<M+20, x=4 if x>=M+20. The cooccurrence matrix is computed by finding the number of transitions between values in the four sets in a certain direction. Since there are four sets the cooccurrence matrix is 4×4. As an example consider a pixel of value 1 and its nearest neighbor to the right which also has the same value. For this pixel, the cooccurrence matrix for transitions to the right would therefore increment in the first row-column. Since pixels outside the nuclear mask are not analyzed transitions are not recorded for the pixels on the edge. Finally, after finding the number of transitions for each type in the cooccurrence matrix each entry is normalized by the total number of transitions. texture_correlation and texture_inertia are computed for four directions: east, southeast, south, and southwest.

| | | |
|---|---|---|
| float | texture_correlation: | The correlation process calculation is described on page 187 of Computer Vision, written by Ballard & Brown, Prentice-Hall, 1982. Options 2, 3, 4 indicate the same analysis, except that instead of occurring in the East direction it occurs in the Southeast, South or Southwest direction. |
| float | texture_inertia: | Also described in Computer Vision, id.. |
| float | texture_range: | The difference between the maximum and minimum gray-scale value in the original image. |
| float | texture_correlation2: | As above, direction southeast |
| float | texture_inertia2: | As above, direction southeast. |
| float | texture_range2: | As above, direction southeast. |
| float | texture_correlation3: | As above, direction south. |
| float | texture_inertia3: | As above, direction south. |
| float | texture_range3: | As above, direction south. |
| float | texture_correlation4: | As above, direction southwest. |
| float | texture_inertia4: | As above, direction southwest. |
| float | texture_range4: | As above, direction southwest. |

COOC

In the following features utilizing the "cooccurrence" or "S" matrix, the matrix is derived from the optical density image. To compute this matrix, the optical density image is first thresholded into six sets evenly divided between the maximum and minimum OD value of the cell's nucleus in question. The S or "coocurrence matrix" is computed by finding the number of transitions between values in the six sets in a certain direction. Since we have six sets, the coocurrence matrix is 6×6. As an example, consider a pixel of value 1 and its nearest neighbor to the right, which also has the same value. For this pixel, the cooccurrence matrix for transitions to the right would increment in the first row-column. Since pixels outside the nuclear mask are not analyzed, transitions are not recorded for the pixels on the edge. Finally, after finding the number of transitions for each type in the coocurrence matrix, each entry is normalized by the total number of transitions. The suffixes on these features indicate the position the neighbor is compared against. They are as follows: _1_0: one pixel to the east. _2_0: two pixels to the east. _4_0: four pixels to the east. _1_45: one pixel to the southeast. _1_90: one pixel to the south. _1_135: one pixel to the southwest.

| | | |
|---|---|---|
| float | cooc_energy_1_0: | The square root of the energy process described in Computer Vision, id . . . Refer to the COOC description above for an explanation of the 1_0 suffix. |
| float | cooc_energy_2_0: | Refer to the COOC description above for an explanation of the 2_0 suffix. |
| float | cooc_energy_4_0: | Refer to the COOC description above for an explanation of the 4_0 suffix. |
| float | cooc_energy_1_45: | Refer to the COOC description above for an explanation of the 1_45 suffix. |
| float | cooc_energy_1_90: | Refer to the COOC description above for an explanation of the 1_90 suffix. |
| float | cooc_energy_1_135: | Refer to the COOC description above for an explanation of the 1_135 suffix. |
| float | cooc_entropy_1_0: | The entropy process defined in Computer Vision, id. Refer to the COOC description above for an explanation of the 1_0 suffix. |
| float | cooc_entropy_2_0: | Refer to the COOC description above for an explanation of the 2_0 suffix. |
| float | cooc_entropy_4_0: | Refer to the COOC description above for an explanation of the 4_0 suffix. |
| float | cooc_entropy_1_45: | Refer to the COOC description above for an explanation of the 1_45 suffix. |
| float | cooc_entropy_1_90: | Refer to the COOC description above for an explanation of the 1_90 suffix. |
| float | cooc_entropy_1_135: | Refer to the COOC description above for an explanation of the 1_135 suffix. |
| float | cooc_inertia_1_0: | The inertia process defined in Computer Vision, id.. |
| float | cooc inertia 2_0: | Refer to the COOC description above for an explanation of the 2_0 suffix. |
| float | cooc_inertia_4_0: | Refer to the COOC description above for an explanation of the 4_0 suffix. |
| float | cooc_inertia_1_45: | Refer to the COOC description above for an explanation of the 1_45 suffix. |
| float | cooc_inertia_1_90: | Refer to the COOC description above for an explanation of the 1_90 suffix. |
| float | cooc_inertia_1_135: | Refer to the COOC description |

| | | |
|---|---|---|
| | | above for an explanation of the 1_135 suffix. |
| float | cooc_homo_1_0: | The homogeneity process described in Computer Vision, id.. Refer to the COOC description above for an explanation of the 1_0 suffix. |
| float | cooc_homo_2_0: | Refer to the COOC description above for an explanation of the 2_0 suffix. |
| float | cooc_homo_4_0: | Refer to the COOC description above for an explanation of the 4_0 suffix. |
| float | cooc_homo_1_45: | Refer to the COOC description above for an explanation of the 1_45 suffix. |
| float | cooc_homo_1_90: | Refer to the COOC description above for an explanation of the 1_90 suffix. |
| float | cooc_homo_1_135: | Refer to the COOC description above for an explanation of the 1_135 suffix. |
| float | cooc corr_1_0: | The correlation process described in Computer Vision, id.. Refer to the COOC description above for an explanation of the 1_0 suffix. |
| float | cooc_corr_2_0: | Refer to the COOC description above for an explanation of the 2_0 suffix. |
| float | cooc_corr_4_0: | Refer to the COOC description above for an explanation of the 4_0 suffix. |
| float | cooc_corr_1_45: | Refer to the COOC description above for an explanation of the 1_45 suffix. |
| float | cooc_corr_1_90: | Refer to the COOC description above for an explanation of the 1_90 suffix. |
| float | cooc_corr_1_135: | Refer to the COOC description above for an explanation of the 1_135 suffix. |

Run Length

The next five features are computed using run length features. Similar to the cooccurrence features, the optical density image is first thresholded into six sets evenly divided between the maximum and minimum OD value of the cell's nucleus in question. The run length matrix is then computed from the lengths and orientations of linearly connected pixels of identical gray levels. For example, the upper left corner of the matrix would count the number of pixels of gray level 0 with no horizontally adjacent pixels of the same gray value. The entry to the right of the upper left corner counts the number of pixels of gray level 0 with one horizontally adjacent pixel of the same gray level.

float  emphasis_short: The number of runs divided by the length of the run squared:

$$\sum_{i=1}^{\#\,gray} \sum_{j=1}^{\#\,runs} \frac{P(i,j)}{j^2}$$

p(i,j) is the number of runs with gray level i and length j. This feature emphasizes short runs, or high texture.

float  emphasis_long: The product of the number of runs and the run length squared:

p(i,j) is the number of runs with gray level i and length j. This feature emphasizes long runs, or low $$\sum_{i=1}^{\#\,gray} \sum_{j=1}^{\#\,runs} j^2 \cdot p(i,j)$$

texture.

float  nonuniform_gray: The square of the number of runs for each gray level:

$$\sum_{i=1}^{\#\,gray} \left[ \sum_{j=1}^{\#\,runs} p(i,j) \right]^2$$

The process is at a minimum when the runs are equally distributed among gray levels.

float  nonuniform_run: The square of the number of runs for each run length:

$$\sum_{j=1}^{\#\,runs} \left[ \sum_{i=1}^{\#\,gray} p(i,j) \right]^2$$

This process is at its minimum when the runs are equally distributed in length.

float  percentage_run: The ratio of the total number of runs to the number of pixels in the nuclear mask:

$$\frac{\sum_{i=1}^{\#\,gray} \sum_{j=1}^{\#\,runs} p(i,j)}{\#\,pixels}$$

This feature has a low value when the structure of the object is highly linear.

| | | |
|---|---|---|
| float | inertia_2_min_axis: | Minimum axis of the 2nd moment of inertia of the nuclear region normalized by the area in pixels. |
| float | inertia_2_max_axis: | Maximum axis of the 2nd moment of inertia of the nuclear region normalized by the area in pixels. |
| float | inertia_2 ratio: | inertia_2_min_axis/ inertia_2_max_axis. |
| float | max od: | Maximum optical density value contained in the nuclear region. |
| float | min_od: | Minimum optical density value contained in the nuclear region. |
| float | sd_od: | Standard deviation of the optical density values in the nuclear region. |
| float | cell_free_lying: | This feature can take on two values: 0.0 and 1.0 (1.0 indicates the nucleus is free lying). To determine if a cell is free lying, a connected components is done on the cytoplasm image, filtering out any components smaller than 400 pixels and larger in size than the integer variable AlgFreeLyingCytoMax(default is 20000). If only one nucleus bounding box falls inside the bounding box of a labeled cytoplasm, the nucleus (cell) will be labeled free lying (1.0), else the nucleus will be labeled 0.0. |
| float | cell_semi_isolated: | This feature can take on two values:0.0 and 1.0 (1.0 indicates the nucleus is semi-isolated). A nucleus is determined to be semi-isolated when the center of its bounding box is a minimum euclidean pixel distance from all other nuclei (center of their bounding boxes). The minimum distance that is used as a threshold is stored in the global floating-point variable AlgSemiIsolatedDistanceMin on the FOV card (default is 50.0). Only nuclei with the cc.active field non-zero will be used in distance comparisons; non-active cells will be ignored entirely. |
| float | cell_cyto_area: | If the cell has been determined to be free-lying (cell_free_lying= 1.0), this number represents the number of pixels in the cytoplasm (value is approximated due to earlier downsampling). If the cell is not free-lying, this number is 0.0. |
| float | cell_nc_ratio: | If the cell has been determined to be free-lying (cell_free_lying= 1.0), this number is cc.area/cell_cyto_area. If the cell is not free-lying, this number is 0.0. |
| float | cell_centroid_diff: | This feature is used on free-lying cells. The centroid of the cytoplasm is calculated, and the centroid of the nucleus. The feature value is the difference between these two centroids. |

Local Area Context Normalization Features

The original image nucleus is assumed to contain information not only about the nucleus, but also about background matter. The gray level recorded at each pixel of the nucleus will be a summation of the optical density of all matter in the vertical column that contains the particular nucleus pixel. In other words, if the nucleus is located in a cytoplasm which itself is located in a mucus stream, the gray level values of the nucleus will reflect not only the nuclear matter, but also the cytoplasm and mucus in which the nucleus lies. To try to measure features of the nucleus without influence of the surroundings and to measure the nucleus surroundings, two regions have been defined around the nucleus. Two regions have been defined because of a lack of information about how much area around the nucleus is enough to identify what is happening in proximity to the nucleus.

The two regions are rings around each nucleus. The first ring expands 5 pixels out from the nucleus (box 7×7 and diamond 4) and is designated as the "small" ring. The second region expands 15 pixels out from the nucleus (box 15×15 and diamond 9) and is called the "big" ring.

| | | |
|---|---|---|
| float | sm_bright: | Average intensity of the pixels in the small ring as measured in the original image. |
| float | big_bright: | Average intensity of the pixels in the big ring as measured in the original image. |
| float | nuc_bright_sm: | Average intensity of the nuclear pixels divided by the average intensity of the pixels in the big ring. |
| float | nuc_bright_big: | Average intensity of the nuclear pixels divided by the average intensity of the pixels in the small ring. |

3×3

The original image is subtracted from a 3×3 closed version of the original. The resultant image is the 3×3 closing residue of the original. This residue gives some indication as to how many dark objects smaller than a 3×3 area exist in the given region.

| | | |
|---|---|---|
| float | sm_edge_3_3: | Average intensity of the 3 × 3 closing residue in the small ring region. |
| float | big_edge_3_3: | Average intensity of the 3 × 3 closing residue in the big ring region. |
| float | nuc_edge_3_3_sm: | Average intensity of the 3 × 3 closing residue in the nuclear region divided by the average intensity of the 3 × 3 closing residue in the small ring. |
| float | nuc_edge_3_3_big: | Average intensity of the 3 × 3 closing residue in the nuclear region divided by the average intensity of the 3 × 3 closing residue in the big ring. |

5×5

The residue of a 5×5 closing of the original image is done similarly to the 3×3 closing residue except that the 3×3 closed image is subtracted from the 5×5 closed image instead of the original. This isolates those objects between 3×3 and 5×5 in size.

| | | |
|---|---|---|
| float | sm_edge_5_5: | Average intensity of the 5 × 5 closing residue in the small ring region. |
| float | big_edge_5_5: | Average intensity of the 5 × 5 closing residue in the big ring region. |
| float | nuc_edge_5_5_sm: | Average intensity of the 5 × 5 closing residue in the nuclear region divided by the average intensity of the 5 × 5 closing residue in the small ring. |
| float | nuc_edge_5_5_big: | Average intensity of the 5 × 5 closing residue in the nuclear region divided by the average intensity of the 5 × 5 closing residue in the big ring. |

9×9

The residue of a 9×9 closing of the original image is done in the same way as the 5×5 closing residue described above except the 5×5 closing residue is subtracted from the 9×9 residue rather than the 3×3 closing residue.

| | | |
|---|---|---|
| float | sm_edge_9_9: | Average intensity of the 9 × 9 closing residus in the small ring region. |
| float | big_edge_9_9: | Average intensity of the 9 × 9 closing residue in the big ring region. |
| float | nuc_edge_9_9_sm: | Average intensity of the 9 × 9 closing residue in the nuclear region divided by the average intensity of the 9 × 9 closing residue in the small ring. |
| float | nuc_edge_9_9_big: | Average intensity of the 9 × 9 closing residue in the nuclear region divided by the average intensity of the 9 × 9 closing residue in the big ring. |

2 Mag

To find if an angular component exists as part of the object texture, closing residues are done in the area of interest using horizontal and vertical structuring elements. The information is combined as a magnitude and an angular disparity measure. The first structuring elements used are a 2×1 and 1×2.

```
float   nuc_edge_2_mag: Magnitude of 2×1 and 1×2 closing
residues within the nuclei. Square root of ( (average
horizontal residue)2 + (average vertical residue)2 ).
float   sm_edge_2_mag: Magnitude of 2×1 and 1×2 closing
residues within the small ring. Square root of ( (average
horizontal residue)2 + (average vertical residue)2 ).
float   big_edge_2_mag: Magnitude of 2×1 and 1×2 closing
residues within the big ring. Square root of ( (average
horizontal residue)2 + (average vertical residue)2 ).
float   nuc_edge_2_mag_sm: nuc_edge_2_mag /
sm_edge_2_mag.
float   nuc_edge_2_mag_big: nuc_edge_2_mag /
big_edge_2_mag.
float   nuc_edge_2_dir: Directional disparity of 2×1 and
1×2 closing residues within the nuclei. (average vertical
residue) / ( (average horizontal residue) + (average
vertical residue) ).
float   sm_edge_2_dir: Directional disparity of 2×1 and
1×2 closing residues in the small ring. (average vertical
residue) / ( (average horizontal residue) + (average
vertical residue) ).
float   big_edge_2_dir: Directional disparity of 2×1 and
1×2 closing residues in the big ring. (average vertical
residue) / ( (average horizontal residue) + (average
vertical residue) ).
float   nuc_edge_2_dir_sm: nuc_edge_2_dir /
sm_edge_2_dir.
float   nuc_edge_2_dir_big: nuc_edge_2_dir /
big_edge_2_dir.
```

5 Mag

The structuring elements used are a 5×1 and a 1×5. In this case, the residue is calculated with the 2×1 or 1×2 closed images rather than the original as for the 2×1 and 1×2 structuring elements described previously.

```
float   nuc_edge_5_mag: Magnitude of 5×1 and 1×5 closing
residues within the nuclei. Square root of ( (average
horizontal residue)2 + (average vertical residue)2 ).
float   sm_edge_5_mag: Magnitude of 5×1 and 1×5 closing
residues within the small ring. Square root of ( (average
horizontal residue)2 + (average vertical residue)2 ).
float   big_edge_5_mag: Magnitude of 5×1 and 1×5 closing
residues within the big ring. Square root of ( (average
horizontal residue)2 + (average vertical residue)2 ).
float   nuc_edge_5_mag_sm: nuc_edge_5_mag /
sm_edge_5_mag
float   nuc_edge_5_mag_big: nuc_edge_5_mag /
big_edge_5_mag
float   nuc_edge_5_dir: Directional disparity of 5×1 and
1×5 closing residues within the nuclei. (average vertical
residue) / ( (average horizontal residue) + (average
vertical residue) ).
float   sm_edge_5_dir: Directional disparity of 5×1 and
1×5 closing residues in the small ring. (average vertical
residue) / ( (average horizontal residue) + (average
vertical residue) ).
float   big_edge_5_dir: Directional disparity of 5×1 and
1×5 closing residues in the big ring. (average vertical
residue) / ( (average horizontal residue) + (average
vertical residue) ).
float   nuc_edge_5_dir_sm: nuc_edge_5_dir /
sm_edge_5_dir
float   nuc_edge_5_dir_big: nuc_edge_5_dir /
big_edge_5_dir
```

9 Mag

The last of the angular structuring elements used are a 9×1 and 1×9. In this case, the residue is calculated with the 5×1 or 1×5 closed images rather than the 2×1 and 1×2 structuring elements described for the 5×1 and 1×5 elements.

```
float   nuc_edge_9_mag: Magnitude of 9×1 and 1×9 closing
residues within the nuclei. Square root of ( (average
horizontal residue)2 + (average vertical residue)2 ).
float   sm_edge_9_mag: Magnitude of 9×1 and 1×9 closing
residues within the small ring. Square root of ( (average
horizontal residue)2 + (average vertical residue)2 ).
float   big_edge_9_mag: Magnitude of 9×1 and 1×9 closing
residues within the big ring. Square root of ( (average
horizontal residue)2 + (average vertical residue)2 ).
float   nuc_edge_9_mag_sm: nuc_edge_9_mag /
sm_edge_9_mag
float   nuc_edge_9_mag_big: nuc_edge_9_mag /
big_edge_9_mag
float   nuc_edge_9_dir: Directional disparity of 9×1 and
1×9 closing residues within the nuclei. (average vertical
residue) / ( (average horizontal residue) + (average
vertical residue) ).
float   sm_edge_9_dir: Directional disparity of 9×1 and
1×9 closing residues in the small ring. (average vertical
residue) / ( (average horizontal residue) + (average
vertical residue) ).
float   big_edge_9_dir: Directional disparity of 9×1 and
1×9 closing residues in the big ring. (average vertical
residue) / ( (average horizontal residue) + (average
vertical residue) ).
float   nuc_edge_9_dir_sm: nuc_edge_9_dir /
sm_edge_9_dir
float   nuc_edge_9_dir_big: nuc_edge_9_dir /
big_edge_9_dir
```

Blur

As another measure of texture, the original is blurred using a 5×5 binomial filter. A residue is created with the absolute magnitude differences between the original and the blurred image.

```
float   nuc_blur_ave: Average of blur image over label
mask.
float   nuc_blur_sd: Standard deviation of blur image over
label mask.
float   nuc_blur_sk: skewness of blur image over label
mask.
float   nuc_blur_ku: kurtosis of blur image over label
mask.
float   sm_blur_ave: Average of blur image over small
ring.
float   sm_blur_sd: Standard deviation of blur image over
small ring.
float   sm_blur_sk: Skewness of blur image over small
ring.
float   sm_blur_ku: Kurtosis of blur image over small
ring.
float   big_blur_ave: Average of blur image over big ring.
float   big_blur_sd: Standard deviation of blur image over
big ring.
float   big_blur_sk: Skewness of blur image over big ring.
float   big_blur_ku: Kurtosis of blur image over big ring.
float   nuc_blur_ave_sm: Average of blur residue for the
nuclei divided by the small ring.
float   nuc_blur_sd_sm: Standard deviation of blur residue
for the nuclei divided by the small ring.
float   nuc_blur_sk_sm: Skew of blur residue for the
nuclei divided by the small ring.
float   nuc_blur_ave_big: Average of blur residue for the
nuclei divided by the big ring.
float   nuc_blur_sd_big: Standard deviation of blur
residue for the nuclei divided by the big ring.
float   nuc_blur_sk_big: Skew of blur residue for the
nuclei divided by the big ring.
float   mod_N_C_ratio: A ratio between the nuclear area
and the cytoplasm area is calculated. The cytoplasm for
each nuclei is determined by taking only the cytoplasm area
that falls inside of a skiz boundary between all nuclei
objects. The area of the cytoplasm is the number of
``` cytoplasm pixels that are in the skiz area corresponding to the nuclei of interest. The edge of the image is treated as an object and therefore creates a skiz boundary.

float  mod_nuc_OD: The average optical density of the nuclei is calculated using floating point representations for each pixel optical density rather than the integer values as implemented in the first version. The optical density values are scaled so that a value of 1.2 is given for pixels of 5 or fewer counts and a value of 0.05 for pixel values of 245 or greater. The pixel values between 5 and 245 span the range logarithmically to meet each boundary condition.

float  mod_nuc_IOD: The summation of the optical density values for each pixel within the nuclei.

float  mod_nuc_OD_sm: The average optical density of the nuclei minus the average optical density of the small ring.

float  mod_nuc_OD_big: The average optical density of the nuclei minus the average optical density of the big ring.

float  mod_nuc_IOD_sm: *mod_nuc_OD_sm* * number of pixels in the nuclei. Essentially, this is the integrated optical density of the nuclei normalized by the average optical density of the pixels within the small ring around the nuclei.

float  mod_nuc_IOD_big: *mod_nuc_OD_big* * number of pixels in the nuclei. Same as above, except the average optical density in the big ring around the nuclei is used to normalized the data.

OD_bin_*_*

These features are the result of placing each pixel in the nuclear mask area in a histogram where each bin represents a range of optical densities. The numbers should be read as 1_2=1.2, 0_825=0.825.

The original image is represented as transmission values. These values are converted during the binning process to show equal size bins in terms of optical density which is a log transformation of the transmission. The Histogram bins refer to the histogram of pixels of transmission values within the nuclear mask.

float  OD_bin_1_2: Sum Histogram bins #0 - 22 / Area of label mask.
float  OD_bin_1_125: Sum Histogram bins #13 / Area of label mask.
float  OD_bin_1_05: Sum Histogram bins #23 - 26 / Area of label mask.
float  OD_bin_0_975: Sum Histogram bins #27 - 29 / Area of label mask.
float  OD_bin_0_9: Sum Histogram bins #30 - 34 / Area of label mask.
float  OD_bin_0_825: Sum Histogram bins #35 - 39 / Area of label mask.
float  OD_bin_0_75: Sum Histogram bins #40 - 45 / Area of label mask.
float  OD_bin_0_6 75: Sum Histogram bins #46 - 53 / Area of label mask.
float  OD_bin_0_6: Sum Histogram bins #54 - 62 / Area of label mask.
float  OD_bin_0_525: Sum Histogram bins #63 - 73 / Area of label mask.
float  OD_bin_0_45: Sum Histogram bins #74 - 86 / Area of label mask.
float  OD_bin_0_375: Sum Histogram bins #87 - 101 / Area of label mask.
float  OD_bin_0_3: Sum Histogram bins #102 - 119 / Area of label mask.
float  OD_bin_0_225: Sum Histogram bins #120 - 142 / Area of label mask.
float  OD_bin_0_15: Sum Histogram bins #143 - 187 / Area of label mask.
float  OD_bin_0_075: Sum Histogram bins #188 - 255 / Area of label mask.
float  context_3a: systemFor this feature, the bounding box of the nucleus is expanded by 15 pixels on each side. The feature is the ratio of the area of other segmented objects which intersect the enlarged box to compactness of the box, where the compactness is defined as the perimeter of the box squared divided by the area of the box.

float  hole_percent: The segmentation is done in several steps. At an intermediate step, the nuclear mask contains holes which are later filled in to make the mask solid. This feature is the ratio of the area of the holes to the total area of the final, solid, mask.

float  context_1b: For this feature, the bounding box of the nucleus is expanded by 5 pixels on each side. The feature is the ratio of the area of other segmented objects which intersect the enlarged box to the total area of the enlarged box.

float  min_distance: The distance to the centroid of the nearest object from the centroid of the current object.

The Invention Results Descriptions

This section shows all of the results of the invention that are written to the results structure TwentyXResult, which is contained in alh_twentyx.h..

int  high_count: Measures dark edge gradient content of the whole original image. This is a measure of how much cellular material may be in the image.
int  high_mean: The average value of all pixels in an image that have values between 199 and 250. This feature provides some information about an image's background.
int  medium_threshold: *lower_limit_0* - *lower_limit_1* where *lower_limit_0* is the value of the *low_threshold*+30, or 70, whichever is greater. *lower_limit_1* is the value of *high_mean* - 40, or 150, whichever is greater.
int  low_threshold: The low threshold value is the result of an adaptive threshold calculation for a certain range of pixel intensities in an image during the segmentation process. It gives a measure for how much dark matter there is in an image. If the threshold is low, there is a fair amount of dark matter in the image. If the threshold is high, there are probably few high density objects in the image.
float  time1: Time variables which may be set during the invention processing.
float  time2: Same as time1
float  time3: Same as time1
float  time4: Same as time1
float  stain_mean_od: The cumulative value of *mean_od* for all objects identified as intermediate cells.
float  stainsq_mean_od: The cumulative squared value of mean_od for all objects identified as intermediate cells.
float  stain_sd_orig2: The cumulative value of *sd_orig2* for all objects identified as intermediate cells.
float  stainsq_sd_orig2: The cumulative squared value of *sd_orig2* for all objects identified as intermediate cells.
float  stain_nc_contrast_orig: The cumulative value of *nc_contrast_orig* for all objects identified as intermediate cells.
float  stainsq_nc_contrast_orig: The cumulative squared value of *nc_contrast_orig* for all objects identified as intermediate cells.
float  stain_mean_outer_od_r3: The cumulative value of *mean_outer_od_r3* for all objects identified as intermediate cells.
float  stainsq_mean_outer_od_r3: The cumulative squared value of *mean_outer_od_r3* for all objects identified as intermediate cells.
float  stain_nuc_blur_ave: The cumulative value of *nuc_blur_ave* for all objects identified as intermediate cells.
float  stainsq_nuc_blur_ave: The cumulative squared value of *nuc_blur_ave* for all objects identified as intermediate cells.
float  stain_edge_contrast_orig: The cumulative value of *edge_contrast_orig* for all objects identified as intermediate cells.
float  stainsq_edge_contrast_orig: The cumulative squared value of *edge_contrast_orig* for all objects identified as intermediate cells.
int     intermediate_hist1 [10] [6]: Histogram representing
the features of all intermediate cells identified by the
first classifier. 10 bins for IOD, and 6 for nuclear area.
int     intermediate_hist2 [8] [6]: Histogram representing
the features of all intermediate cells identified by the
second classifier. 8 bins for IOD, and 6 for nuclear area.
int     sil_box1_artifact_count: Total number of objects
in the image classified as artifacts by the Box1 classifier.
int     sil_box2_artifact_count: Total number of objects
in the image classified as artifacts by the Box2 classifier.
int     sil_box3_artifact_count: Total number of objects
in the image classified as artifacts by the first classifier
of the Artifact Filter.
int     sil_box4_artifact_count: Total number of objects
in the image classified as artifacts by the second
classifier of the Artifact Filter.
int     sil_box5_artifact_count: Total number of objects
in the image classified as artifacts by the third classifier
of the Artifact Filter.
int     conCompCount: The number of objects segmented in
the image.
int     sil_stage1_normal_count1: Total number of objects
classified as normal at the end of the Stage1 classifier.
int     sil_stage1_artifact_count1: Total number of
objects classified as artifact at the end of the Stage1
classifier.
int     sil_stage1_abnormal_count1: Total number of
objects classified as abnormal at the end of the Stage1
classifier.
int     sil_stage2_normal_count1: Total number of objects
classified as normal at the end of the Stage2 94 classifier.
int     sil_stage2_artifact_count1: Total number of
objects classified as artifact at the end of the Stage2 94
classifier.
int     sil_stage2_abnormal_count1: Total number of
objects classified as abnormal at the end of the Stage2 94
classifier.
int     sil_stage3_normal_count1: Total number of objects
classified as normal at the end of the stage3 96 classifier.
int     sil_stage3_artifact_count1: Total number of
objects classified as artifact at the end of the stage3 96
classifier.
int     sil_stage3_abnormal_count1: Total number of
objects classified as abnormal at the end of the stage3 96
classifier.
int     sil_cluster_stage2_count: The number of objects
classified as abnormal by the Stage2 94 classifier which are
close to abnormal objects from the stage3 96 classifier.
int     sil_cluster_stage1_count: The number of objects
classified as abnormal by the Stage1 classifier which are
close to abnormal objects from the Stage2 94 classifier.
float   sil_est_cellcount: An estimate of the number of
squamous cells in the image.
int     sil_stage2_alarm_IOD_histo [16]: Histogram
representing the IOD of all objects classified as abnormal
by the Stage2 94 classifier.
int     sil_stage2_alarm_conf hist [10]: Histogram
representing the confidence of classification for all
objects classified as abnormal by the Stage2 94 classifier.
int     sil_stage3_alarm_IOD_histo [16]: Histogram
representing the IOD of all objects classified as abnormal
by the stage3 96 classifier.
int     sil_stage3_alarm_conf_hist [10]: Histogram
representing the confidence of classification for all
objects classified as abnormal by the stage3 96 classifier.
int     sil_stage1_normal_count2: Total number of objects
classified as normal by the Stage1 Box classifier.
int     sil_stage1_abnormal_count2: Total number of
objects classified as abnormal by the Stage1 Box classifier.
int     sil_stage1_artifact_count2: Total number of
objects classified as artifact by the Stage1 Box classifier.
int     sil_p1_stage2_normal_count2: Total number of
objects classified as normal by the Stage2 94 Box
classifier.
int     sil_p1_stage2_abnormal_count2: Total number of
objects classified as abnormal by the Stage2 94 Box
classifier.
int     sil_p1_stage2_artifact_count2: Total number of
objects classified as artifact by the Stage2 94 Box
classifier.
int     sil_p1_stage3_normal_count2: Total number of
objects classified as normal by the stage3 96 Box
classifier.
int     sil_p1_stage3_abnormal_count2: Total number of
objects classified as abnormal by the stage3 96 Box
classifier.
int     sil_p1_stage3_artifact_count2: Total number of
objects classified as artifact by the stage3 96 Box
classifier.
int     sil_stage4_alarm_count: Total number of objects
classified as abnormal by the stage4 98 classifier.
int     sil_stage4_prob_hist [12]: Histogram representing
the confidence of classification for all objects classified
as abnormal by the stage4 98 classifier.
int     sil_ploidy_alarm_count1: Total number of objects
classified as abnormal by the first ploidy classifier 100.
int     sil_ploidy_alarm_count2: Total number of objects
classified as abnormal by the second ploidy classifier 100.
int     sil_ploidy_prob_hist [12]: Histogram representing
the confidence of classification for all objects classified
as abnormal by the ploidy classifier 100.
int     sil_S4_and_P1_count: Total number of objects
classified as abnormal by both the stage4 98 and the first
ploidy classifier 100.
int     sil_S4_and_P2_count: Total number of objects
classified as abnormal by both the stage4 98 and the second
ploidy classifier 100.
int     atypical_pdf_index [8] [8]: A 2D histogram
representing two confidence measures of the objects
classified as abnormal by the stage2 94 Box classifier.
Refer to the description of the atypicality classifier in
this document.
int     sil_seg_x_s2_decisive [4]: A 4 bin histogram of the
product of the segmentation robustness value and the Stage2
94 decisiveness value.
int     sil_seg_x_s3_decisive [4]: A 4 bin histogram of the
product of the segmentation robustness value and the stage3
96 decisiveness value.
int     sil_s2_x_s3_decisive [4]: A 4 bin histogram of the
product of the Stage2 94 decisiveness value and the stage3
96 decisiveness value.
int     sil_seg_x_s2_x_s3_decisive [4]: A 4 bin histogram
of the product of the segmentation robustness value, the
Stage2 94 decisiveness value, the stage3 96 decisiveness
value.
int     sil_stage2_dec_x_seg [4] [4]: A 4×4 array of Stage2
94 decisiveness (vertical axis) vs. segmentation robustness
(horizontal axis).
int     sil_stage3_dec_x_seg [4] [4]: A 4×4 array of stage3
96 decisiveness (vertical axis) vs. segmentation robustness
(horizontal axis).
int     sil_s3_x_s2_dec_x_seg [4] [4]: A 4×4 array of the
product of Stage2 94 and stage3 96 decisiveness (vertical
axis) vs. segmentation robustness (horizontal axis).
int     sil_s3_x_segrobust_x_s2pc [4] [4]: A 4×4 array of
the product of segmentation robustness and stage3 96
decisiveness (vertical axis) vs. the product of Stage2 94
confidence and Stage2 94 decisiveness (horizontal axis).
int     sil_s3_x_segrobust_x_s3pc [4] [4]: A 4×4 array of
the product of segmentation robustness and stage3 96
decisiveness (vertical axis) vs. the product of stage3 96
confidence and stage3 96 decisiveness (horizontal axis).
float   sil_stage3_ftr, [NUM_FOV_ALM], [LEN_FOV_FTR]:
A set of 8 features for an object which was classified
as abnormal by the stage3 96 classifier. NUM_FOV_ALM
refers to the number of the alarm as it was detected in
the 20x scan (up to 50 will have features recorded).
LEN_FOV_FTR refers to the feature number: 0 - 7

Cell Types Recognized by the Invention

The invention has been trained to recognize single or free lying cell types: normal, potentially abnormal, and artifacts that typically appear in Papanicolaou-stained cervical smears. This section lists the cell types that were used to train the invention.

Normal Single Cells single superficial squamous
single intermediate squamous
single squamous metaplastic
single parabasal squamous
single endocervical
single endometrial
red blood cells

Abnormal Single Cells single atypical squamous
single atypical metaplastic
single atypical endocervical columnar
single atypical endometrial
single low grade SIL
single high grade SIL
single endocervical columnar dysplasia, well segmented
single carcinoma in situ, endocervical columnar, well segmented
single adenocarcinoma, endocervical columnar
single adenocarcinoma, endometrial
single adenocarcinoma, metaplastic
single invasive carcinoma, small cell squamous
single invasive carcinoma, large cell squamous
single invasive carcinoma, keratinizing squamous
single marked repair/reactive squamous
single marked repair/reactive, endocervical
single marked repair/reactive, metaplastic
single herpes
single histiocyte
single lymphocyte
single slightly enlarged superficial squamous
single slightly enlarged intermediate squamous
single slightly enlarged metaplastic squamous
single slightly enlarged parabasal squamous
slightly enlarged endocervical

Artifacts single air dried intermediate cell nucleus
single air dried metaplastic/parabasal cell nucleus
single air dried endocervical cell nucleus
single questionable abnormal cell nucleus
single over segmented intermediate cell nucleus
single over segmented metaplastic/parabasal cell nucleus
single artifact, 1 nucleus over segmented
artifact, 2 nuclei
artifact, 3+ nuclei
single folded cytoplasm
cytoplasm only
bare nucleus
unfocused
polymorphs (white blood cells)
graphites
corn flaking
mucous
junk from cover slip
other junk The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An apparatus for measuring reliability for object segmentation of a biological specimen comprising:

(a) means for acquiring at least one image of the biological specimen having an image output;

(b) means for image segmentation connected to the image output to detect objects of interest, wherein the means for image segmentation has a segmented object output;

(c) means for feature extraction connected to the segmented object output, wherein the means for feature extraction has a segmentation reliability feature output; and (d) means for classification of objects connected to the segmentation reliability feature output having a classified output, where the classified output comprises a measure of reliability of the segmented object output.

2. The apparatus of claim 1 wherein the means for feature extraction comprises an object feature extractor.

3. The apparatus of claim 1 wherein the means for feature extraction comprises a contextual feature extractor.

4. The apparatus of claim 1 wherein the means for feature extraction comprises a whole image feature extractor.

5. The apparatus of claim 1 wherein the objects of interest comprise free-lying cells.

6. The apparatus of claim 1 wherein the objects of interest comprise non-nuclear overlapped cells.

7. The apparatus of claim 1 wherein the objects of interest comprise normal cells.

8. The apparatus of claim 7 wherein the normal cells comprise reference intermediate cells.

9. The apparatus of claim 1 wherein the biological specimen is a specimen prepared by the Papanicolaou method.

10. The apparatus of claim 1 wherein the biological specimen is a gynecological specimen.

11. The apparatus of claim 1 further comprising a means for accumulating the classified output.

12. The apparatus of claim 1 further comprising a means for measuring a stain of at least one type of object.

13. The apparatus of claim 12 wherein the at least one type of object comprises reference intermediate cells.

14. The apparatus of claim 1 further comprising a means for measuring a classification confidence for a set of objects classified as being object types of interest.

15. The apparatus of claim 1 wherein the objects of interest comprise abnormal cells.

16. The apparatus of claim 15 wherein the abnormal cells comprise cancerous and precancerous cells.

17. The apparatus of claim 1 wherein the objects of interest comprise artifacts.

* * * * *